(12) United States Patent
Martin et al.

(10) Patent No.: US 7,141,405 B2
(45) Date of Patent: Nov. 28, 2006

(54) CHIMERIC GB VIRUS B (GBV-B)

(75) Inventors: Annette Martin, Paris (FR); David V. Sangar, Burbage (GB); Stanley M. Lemon, Galveston, TX (US); René Rijnbrand, Galveston, TX (US)

(73) Assignees: Board of Regents, The University of Texas System, Austin, TX (US); Institut Pasteu, Paris (FR)

( * ) Notice: Subject to any disclaimer, the term of this patent is extended or adjusted under 35 U.S.C. 154(b) by 435 days.

(21) Appl. No.: 10/189,359

(22) Filed: Jul. 3, 2002

(65) Prior Publication Data

US 2004/0039187 A1 Feb. 26, 2004

Related U.S. Application Data

(63) Continuation-in-part of application No. 09/587,653, filed on Jun. 5, 2000.

(60) Provisional application No. 60/137,665, filed on Jun. 4, 1999.

(51) Int. Cl.
*C12N 7/01* (2006.01)
*C07H 21/04* (2006.01)

(52) U.S. Cl. .............. 435/236.1; 536/23.72; 536/24.1

(58) Field of Classification Search .......... 435/235.1, 435/69.1; 424/204.1, 225.1; 536/23.72, 536/23.1, 24.1
See application file for complete search history.

(56) References Cited

U.S. PATENT DOCUMENTS

| 5,807,670 A | 9/1998 | Muerhoff et al. ............ 435/5 |
| 6,627,437 B1 * | 9/2003 | Traboni .................. 435/320.1 |
| 2001/0034019 A1 | 10/2001 | Hong et al. .................. 435/5 |

FOREIGN PATENT DOCUMENTS

WO    WO 00/75337    12/2000

OTHER PUBLICATIONS

Yanagi et al., Virology, 262, 250-263 (1999).*
Al et al., "Expression of recombinant hepatitis C virus non-structural protein 5B in *Escherichia coli,*" *Virus Res.*, 53:141-149, 1998.
Beames et al., "Development of a primary tamarin hepatocyte culture system for GB virus-B: a surrogate model for hepatitis C. virus," *J. Virol.*, 74:11764-11772, 2000.
Beard et al., "An infectious molecular clone of a Japanese genotype 1b hepatitis C virus," *Hepatology*, 30:316-324, 1999.
Behrens et al., "Identification and properties of the RNA dependent RNA polymerase of hepatitis C virus," *EMBO J*, 15:12-22, 1996.
Chambers et al., "Yellow fever/Japanese encephalitis chimeric viruses. construction and biological properties," *J Virol*, 73:3095-3101, 1999.
Choo et al., "Vaccination of chimpanzees against infection by the hepatitis C virus," *Proc Natl Acad Sci USA*, 91:1294-1298, 1994.
Farci et al., "Lack of protective immunity against reinfection with hepatitis c virus," *Science*, 258:135-140. 1992.
Farci et al., "The natural history of infection with hepatitis C virus (HCV) in chimpanzees: Comparison of serologic responses measured with first- and second-generation assays and relationship to HCV viremia," *The Journal of Infectious Diseases*, 165:1006-1011, 1992.
Filocamo et al., "Chimeric Sindbis viruses dependent on the NS3 protease of hepatitis C virus," *J. Virol*, 71 1417-1427, 1997.
Frolov et al., "Cis-acting RNA elements required for replication of bovine viral diarrhea virus-hepatitis C virus 5' nontranslated region chimeras," *RNA* 4:1418-1435, 1998.
Hijikata et al., "Two distinct protease activities required for the processing of a putative nonstructural precursor protein of hepatitis C virus," *J Virol*, 67:4665-4675, 1993.
Honda et al., "Stability of a stem-loop involving the initiator AUG controls the efficiency of internal initiation of translation on hepatitis C virus RNA," *RNA*, 2:955-968, 1996.
Karayiannis et al., "Studies of GB hepatitis agent in tamarins," *Hepatology*, 9:186-192, 1989.
Kim et al., "Crystal structure of the hepatitis C virus NS3 protease domain complexed with a synthetic NS4A cofactor peptide," *Cell*, 87:343-355, 1996.
Kolykhalov et al., "Identification of a highly conserved element at the 3' terminus of hepatitis C virus genome RNA," *J Virol*, 70:3363-3371, 1996.
Kolykhalov et al., "Transmission of hepatitis C by intrahepatic inoculation of transcribed RNA," *Science*, 277:570-574, 1997.
Lemon and Honda, "Internal ribosome entry sites within the RNA genomes of hepatitis C virus and other flaviviruses," *Seminars in Virology*, 8:274-288, 1997.

(Continued)

*Primary Examiner*—Shanon Foley
(74) *Attorney, Agent, or Firm*—Fulbright & Jaworski, L.L.P.

(57) ABSTRACT

The present invention relates generally to the fields of biochemistry, molecular biology, and virology. More particularly, it relates to the identification of GB virus B (GBV-B)/HCV chimeras. The invention involves nucleic acid constructs and compositions encoding GBV-B/HCV chimera, including at least part of a 5' NTR derived from a HCV 5' NTR. This construct, and chimeric versions of it, may be employed to study GBV-B and related hepatitis family members, such as hepatitis C virus. The invention thus includes methods of preparing GBV-B/HCV chimeric sequences, constructs, and viruses, as well as methods of employing these compositions.

27 Claims, 7 Drawing Sheets

OTHER PUBLICATIONS

Lu and Wimmer, "Poliovirus chimeras replicating under the translational control of genetic elements of hepatitis C virus reveal unusual properties of the internal ribosomal entry site of hepatitis C virus," *Proc Natl Acad Sci USA*, 93:1412-1417, 1996.

Muerhoff et al., "Genomic organisation of GB viruses A and B: Two new members of the flaviviridae associated with GB agent hepatitis," *J Virol*, 69:5621-5630, 1995.

Pletnev et al., "Construction and characterization of chimeric tick-borne encephalitis/dengue type 4 viruses," *Proc. Natl Acad Sci USA*, 89:10532-10536, 1992.

Reynolds et al., "Unique features of internal initiation of hepatitis C virus RNA translation," *EMBO J*, 14:6010-6020, 1995.

Rijnbrand et al., "Mutational analysis of the GB virus B internal ribosome entry site," *J Virol*, 74:773-783, 2000.

Scarselli et al., "GB virus B and hepatitis C virus share substrate specificity," *J Virol*, 71:4985-4989, 1997.

Schlauder et al., "Molecular and serological analysis in the transmission of the GB hepatitis agent," *J Med Virol*, 46:81-90, 1995.

Shaffer et al., "A hepatitis A virus deletion mutant which lacks the first pyrimidine-rich tract of the 5' nontranslated RNA remains virulent in primates after direct intrahepatic nucleic acid transfection," *J Virol*, 69:6600-6604, 1995.

Simons et al., "Identification of two flavivirus like genomes in the GB hepatitis agent," *Proc Natl Acad Sci*, 92:3401-3405, 1995.

Tanaka et al., "A novel sequence found at the 3' terminus of hepatitis C virus genome," *Biochem Biophys Res Comm*, 215:744-749, 1995.

Todd et al., "Replication competent picornaviruses with complete genomic RNA 3' non-coding deletions," *J Virol*, 71:8868-8874, 1997.

Yanagi et al., "Transcripts from a single full length cdna clone of hepatitus c virus are infectious when directly transfected into a liver of a chimpanzee," *Proc Natl Acad Sci USA*, 94:8738-8743, 1998.

Yao et al., "Structure of the hepatitis C virus RNA helicase domain," *Nature Structural Biology*, 4:463-467, 1997.

Zhao et al., "Poliovirus/hepatitis C virus (internal ribosome entry site-core) chimeric viruses: improved growth properties through modification of a proteolytic cleavage site and requirement for core RNA sequence but not for core related polypeptides," *J Virol*, 73:1546-1554, 1999.

* cited by examiner

Sequence differences between chimeric viral RNAs recovered from animals T16444 and T16451, and the parental synthetic III$^{HC}$ RNA.

| nt position | parent | T 16444 | T 16451 | protein / region | aa position | parent | T 16444 | T 16451 |
|---|---|---|---|---|---|---|---|---|
| | | wk 14 | wk 4 | | | | wk 14 | wk 4 |
| 238 ** | C | - | Deleted | 5'NTR | NA | | | |
| 1012 | G | A | A | E1 | 189 | Glu | - | - |
| 2376 | T | C | C | E2 | 644 | Ile | Thr | Thr |
| 5225 | G | - | A | NS4A | 1594 | Ala | - | Thr |
| 6590 | A | G / - | - | NS5A | 2049 | Lys | Glu / - | - |
| 7152 | T | C | C | NS5A | 2236 | Val | Ala | Ala |
| 7945 | A | G | G | NS5B | 2500 | Thr | - | - |
| 8350 | A | - | G | NS5B | 2635 | Thr | - | - |
| 9052 | C | T | T | 3'NTR | NA | | | |
| 9065 | C | T | T | 3'NTR | NA | | | |

Note 1: Numbering according to GBV-B parent genome, except for ** change occuring at the 5' end of domain III of the HCV IRES Note 2: (-) identical to parent residue

FIG. 7

SEQUENCE LISTING

```
<160> NUMBER OF SEQ ID NOS: 16

<210> SEQ ID NO 1
<211> LENGTH: 260
<212> TYPE: RNA
<213> ORGANISM: Unknown
<220> FEATURE:
<223> OTHER INFORMATION: Description of Unknown Organism:  GB VIRUS B

<400> SEQUENCE: 1
gaguuugcga ccauggugga ucagaaccgu uucgggugaa gccauggucu gaaggggaug      60
acgucccuuc uggcucaucc acaaaaaccg ucucgggugg gugaggaguc cuggcugugu     120
gggaagcagu caguauaauu cccgucgugu guggugacgc cucacgacgu auuuguccgc     180
ugugcagagc guaguaccaa gggcugcacc ccgguuuuug uuccaagcgg agggcaaccc     240
ccgcuuggaa uuaaaaacug                                                260

<210> SEQ ID NO 2
<211> LENGTH: 9399
<212> TYPE: DNA
<213> ORGANISM: GBV-A-like virus

<400> SEQUENCE: 2
accacaaaca ctccagtttg ttacactccg ctaggaatgc tcctggagca cccccccctag     60 cagggcgtgg gggatttccc ctgcccgtct gcagaagggt ggagccaacc accttagtat    120
gtaggcggcg ggactcatga cgctcgcgtg atgacaagcg ccaagcttga cttggatggc    180
cctgatgggc gttcatggt tcggtggtgg tggcgcttta ggcagcctcc acgcccacca    240
cctcccagat agagcggcgg cactgtaggg aagaccgggg accggtcact accaaggacg    300
cagacctctt tttgagtatc acgcctccgg aagtagttgg gcaagcccac ctatatgtgt    360
tgggatggtt ggggttagcc atccataccg tactgcctga tagggtcctt gcgagggggat    420 ctgggagtct cgtagaccgt agcacatgcc tgttatttct actcaaacaa gtcctgtacc    480
tgcgcccaga acgcgcaaga acaagcagac gcaggcttca tatcctgtgt ccattaaaac    540
atctgttgaa aggggacaac gagcaaagcg caaagtccag cgcgatgctc ggcctcgtaa    600
ttacaaaatt gctggtatcc atgatggctt gcagacattg gctcaggctg ctttgccagc    660
tcatggttgg ggacgccaag accctcgcca taagtctcgc aatcttggaa tccttctgga    720 ttacccttttg gggtggattg gtgatgttac aactcacaca cctctagtag gcccgctggt    780
ggcaggagcg gtcgttcgac cagtctgcca gatagtacgc ttgctggagg atggagtcaa    840
ctgggctact ggttggttcg gtgtccacct ttttgtggta tgtctgctat ctttggcctg    900
tccctgtagt ggggcgcggg tcactgaccc agacacaaat accacaatcc tgaccaattg    960
```

-continued

```
ctgccagcgt aatcaggtta tctattgttc tccttccact tgcctacacg agcctggttg    1020
tgtgatctgt gcggacgagt gctgggttcc cgccaatccg tacatctcac acccttccaa    1080
ttggactggc acggactcct tcttggctga ccacattgat tttgttatgg gcgctcttgt    1140
gacctgtgac gcccttgaca ttggtgagtt gtgtggtgcg tgtgtattag tcggtgactg    1200
gcttgtcagg cactggctta ttcacataga cctcaatgaa actggtactt gttacctgga    1260
agtgcccact ggaatagatc ctgggttcct agggtttatc gggtggatgg ccggcaaggt    1320
cgaggctgtc atcttcttga ccaaactggc ttcacaagta ccatacgcta ttgcgactat    1380
gtttagcagt gtacactacc tggcggttgg cgctctgatc tactatgcct ctcggggcaa    1440
gtggtatcag ttgctcctag cgcttatgct ttacatagaa gcgacctctg aaaccctat    1500 cagggtgccc actggatgct caatagctga gttttgctcg cctttgatga taccatgtcc    1560
ttgccactct tatttgagtg agaatgtgtc agaagtcatt tgttacagtc caaagtggac    1620
caggcctatc actctagagt ataacaactc catatcttgg taccctata caatccctgg    1680 tgcgagggga tgtatggtta aattcaaaaa taacacatgg ggttgctgcc gtattcgcaa    1740
tgtgccatcg tactgcacta tgggcactga tgcagtgtgg aacgacactc gcaacactta    1800
cgaagtatgc ggtgtaacac catggctaac aaccgcatgg cacaacggct cagccctgaa    1860
attggctata ttacaatacc ctgggtctaa agaaatgttt aaacctcata ttggatgtc    1920 aggccatttg tattttgagg gatcagatac ccctatagtt tacttttatg accctgtgaa    1980
ttccactctc ctaccaccgg agaggtgggc taggttgccc ggtaccccac tgtggtacg    2040 tggttcttgg ttacaggttc cgcaagggtt ttacagtgat gtgaaagacc tagccacagg    2100
attgatcacc aaagacaaag cctggaaaaa ttatcaggtc ttatattccg ccacgggtgc    2160
tttgtctctt acgggagtta ccaccaaggc cgtggtgcta attctgttgg ggttgtgtgg    2220
cagcaagtat cttatttag cctacctctg ttacttgtcc ctttgttttg ggcgcgcttc    2280
tggttaccct ttgcgtcctg tgctcccatc ccagtcgtat ctccaagctg ctgggatgt    2340 tttgtctaaa gctcaagtag ctcctttgc tttgattttc ttcatctgtt gctatctccg    2400
ctgcaggcta cgttatgctg ccctttagg gtttgtgccc atggctgcgg gcttgcccct    2460
aactttcttt gttgcagcag ctgctgccca accagattat gactggtggg tgcgactgct    2520
agtggcaggg ttagttttgt gggccggccg taaccgtggt caccgcatag ctctgcttgt    2580
aggtccttgg cctctggtag cgcttttaac cctcttgcat ttggttacgc ctgcttcagc    2640
ttttgatacc gagataattg gagggctgac aataccacct gtagtagcat tagttgtcat    2700
gtctcgtttt ggcttctttg ctcacttgtt acctcgctgt gctttagtta actcctatct    2760
ttggcaacgt tgggagaatt ggtttttgaa cgttacacta agaccggaga ggttttttct    2820
tgtgctggtt tgttttcccg gtgcgacata tgacgcgctg gtgactttct gtgtgtgtca    2880
cgtagctctt ctatgtttaa catccagtgc agcatcgttc tttgggactg actctagggt    2940
tagggcccat agaatgttgg tgcgtctcgg aaagtgtcat gcttggtatt ctcattatgt    3000
tcttaagttt ttcctcttag tgtttggtga aatggtgtg ttttctata agcacttgca    3060 tggtgatgtc ttgcctaatg attttgcctc gaaactacca ttgcaagagc cattttttccc    3120 ttttgaaggc aagcaaggg tctataggaa tgaaggaaga cgcttggcgt gtggggacac    3180
ggttgatggt ttgcccgttg ttgcgcgtct cggcgacctt gttttcgcag ggttggctat    3240
gccgccagat gggtgggcca ttaccgcacc ttttacgctg cagtgtctct ctgaacgtgg    3300
cacgctgtca gcgatggcag tggtcatgac tggtatagac ccccgaactt ggactggaac    3360
```

```
tatcttcaga ttaggatctc tggccactag ctacatggga tttgtttgtg acaacgtgtt    3420
gtatactgct caccatggca gcaaggggcg ccggttggct catcccacag gctctataca    3480
cccaataacc gttgacgcgg ctaatgacca ggacatctat caaccaccat gtggagctgg    3540
gtcccttact cggtgctctt gcggggagac caagggtat ctggtaacac gactggggtc     3600
attggttgag gtcaacaaat ccgatgaccc ttattggtgt gtgtgcgggg cccttcccat    3660
ggctgttgcc aagggttctt caggtgcccc gattctgtgc tcctccgggc atgttattgg    3720
gatgttcacc gctgctagaa attctggcgg ttcagtcagt cagattaggg ttaggccgtt    3780
ggtgtgtgct ggataccatc cccagtacac agcacatgcc actcttgata caaaacctac    3840
tgtgcctaac gagtattcag tgcaaatttt aattgccccc actggcagcg gcaagtcaac    3900
caaattacca ctttcttaca tgcaggagaa gtatgaggtc ttggtcctaa atcccagtgt    3960
ggctacaaca gcatcaatgc caaagtacat gcacgcgacg tacggcgtga atccaaattg    4020
ctattttaat ggcaaatgta ccaacacagg ggcttcactt acgtacagca catatggcat    4080
gtacctgacc ggagcatgtt cccggaacta tgatgtaatc atttgtgacg aatgccatgc    4140
taccgatgca accaccgtgt tgggcattgg aaaggtccta accgaagctc catccaaaaa    4200
tgttaggcta gtggttcttg ccacggctac ccccctgga gtaatcccta caccacatgc     4260
caacataact gagattcaat taaccgatga aggcactatc ccctttcatg aaaaaagat     4320
taaggaggaa aatctgaaga aagggagaca cctatctttt gaggctacca aaaaacactg    4380
tgatgagctt gctaacgagt tagctcgaaa gggaataaca gctgtctctt actataggg    4440
atgtgacatc tcaaaaatcc ctgagggcga ctgtgtagta gttgccactg atgccttgtg    4500
tacagggtac actggtgact ttgattccgt gtatgactgc agcctcatgg tagaaggcac    4560
atgccatgtt gaccttgacc ctactttcac catgggtgtt cgtgtgtgcg gggtttcagc    4620
aatagttaaa ggccagcgta ggggccgcac aggccgtggg agagctggca tatactacta    4680
tgtagacggg agttgtaccc cttcgggtat ggttcctgaa tgcaacattg ttgaagcctt    4740
cgacgcagcc aaggcatggt atggtttgtc atcaacagaa gctcaaacta ttctggacac    4800
ctatcgcacc caacctgggt tacctgcgat aggagcaaat ttggacgagt gggctgatct    4860
cttttctatg gtcaacccg aaccttcatt tgtcaatact gcaaaaagaa ctgctgacaa     4920
ttatgttttg ttgactgcag cccaactaca actgtgtcat cagtatggct atgctgctcc    4980
caatgacgca ccacggtggc agggagcccg gcttgggaaa aaaccttgtg gggttctgtg    5040
gcgcttggac ggcgctgacg cctgtcctgg cccagagccc agcgaggtga ccagatacca    5100
aatgtgcttc actgaagtca atacttctgg gacagccgca ctcgctgttg gcgttggagt    5160
ggctatggct tatctagcca ttgacacttt tggcgccact tgtgtgcggc gttgctggtc    5220
tattgcatca gtccctaccg gtgctactgt cgccccagtg gttgacgaag aagaaatcgt    5280
ggaggagtgt gcatcattca ttccccttgga ggccatggtt gctgcaatcg ataagctgaa    5340
gagtacaatc accacaacta gtcctttcac attggaaacc gccttgaaa acttaacac      5400
cttcttggg cctcatgcag ctacaatcct tgctatcata gagtattgct gtggtttagt      5460
cactttacct gacaatccct ttgcatcatg cgtgtttgct ttcattgcgg gtattactac    5520
cccactacct cacaagatca aaatgttcct gtcattattt ggaggcgcaa ttgcgtccaa    5580
gcttacagac gctagaggcg cactggcgtt catgatggcc gggctgcgg gaacagctct     5640
tggtacatgg acatcggtgg gttttgtctt tgacatgcta ggcggctatg ctgccgcctc    5700
```

```
atccactgct tgcttgacat ttaaatgctt gatgggtgag tggcccacta tggatcagct    5760
tgctggttta gtctactccg cgttcaatcc ggccgcagga gttgtgggcg tcttgtcagc    5820
ttgtgcaatg tttgctttga caacagcagg gccagatcac tggcccaaca gacttcttac    5880
tatgcttgct aggagcaaca ctgtatgtaa tgagtacttt attgccactc gtgacatccg    5940
caggaagata ctgggcattc tggaggcatc tacccctgg agtgtcatat cagcttgcat     6000
ccgttggctc cacacccga cggaggatga ttgcggcctc attgcttggg gtctagagat     6060
ttggcagtat gtgtgcaatt tctttgtgat ttgctttaat gtccttaaag ctggagttca    6120
gagcatggtt aacattcctg gttgtccttt ctacagctgc cagaagggt acaagggccc     6180 ctggattgga tcaggtatgc tccaagcacg ctgtccatgc ggtgctgaac tcatcttttc    6240
tgttgagaat ggttttgcaa aactttacaa aggacccaga acttgttcaa attactggag    6300
aggggctgtt ccagtcaacg ctaggctgtg tgggtcggct agaccggacc caactgattg    6360
gactagtctt gtcgtcaatt atggcgttag ggactactgt aaatatgaga aatgggaga    6420 tcacattttt gttacagcag tatcctctcc aaatgtctgt ttcacccagg tgccccaac    6480 cttgagagct gcagtggccg tggacggcgt acaggttcag tgttatctag gtgagcccaa    6540
aactccttgg acgacatctg cttgctgtta cggtcctgac ggtaagggta aaactgttaa    6600
gcttcccttc cgcgttgacg tcacacacc tggtgtgcgc atgcaactta atttgcgtga    6660
tgcacttgag acaaatgact gtaattccac aaacaacact cctagtgatg aagccgcagt    6720
gtccgctctt gttttcaaac aggagttgcg gcgtacaaac caattgcttg aggcaatttc    6780
agctggcgtt gacaccacca aactgccagc cccctccatc gaagaggtag tggtaagaaa    6840
gcgccagttc cgggcaagaa ctggttcgct taccttgcct ccccctccga gatccgtccc    6900
aggagtgtca tgtcctgaaa gcctgcaacg aagtgaccg ttagaaggtc cttcaaaccct    6960 ccctccttca ccacctgttc tacagttggc catgccgatg cccctgttgg gagcgggtga    7020
gtgtaaccct ttcactgcaa ttggatgtgc aatgaccgaa acaggcggag ccctgatga    7080 tttacccagt taccctccca aaaggaggt ctctgaatgg tcagacgaaa gttggtcgac    7140
ggctacaacc gtttccagct acgttactgg cccccgtac cctaagatac gggaaagga    7200 ttccactcag tcagcccccg ccaaacggcc tacaaaaaag aagttgggaa agagtgagtt    7260
ttcgtgcagc atgagctaca cctggaccga cgtgattagc ttcaaaactg cttctaaagt    7320
tctgtctgca actcgggcca tcactagtgg tttcctcaaa caaagatcat tggtgtatgt    7380
gactgagccg cgggatgcgg agcttagaaa acaaaaagtc actattaata gacaacctct    7440
gttcccccca tcataccaca agcaagtgag attggctaag gaaaaagctt caaaagttgt    7500
cggtgtcatg tgggactatg atgaagtagc agctcacacg ccctctaagt ctgctaagtc    7560
ccacatcact ggccttcggg gcactgatgt tcgttctgga gcagcccgca aggctgttct    7620
ggacttgcag aagtgtgtcg aggcaggtga gataccgagt cattatcggc aaactgtgat    7680
agttccaaag gaggaggtct tcgtgaagac cccccagaaa ccaacaaaga aaccccccaag   7740 gcttatctcg taccccccacc ttgaaatgag atgtgttgag aagatgtact acggtcaggt    7800
tgctcctgac gtagttaaag ctgtcatggg agatgcgtac gggtttgtag atccacgtac    7860
ccgtgtcaag cgtctgttgt cgatgtggtc acccgatgca gtcggagcca catgcgatac    7920
agtgtgtttt gacagtacca tcacacccga ggatatcatg gtggagacag acatctactc    7980
agcagctaaa ctcagtgacc aacaccgagc tggcattcac accattgcga ggcagttata    8040
cgctggagga ccgatgatcg cttatgatgg ccgagagatc ggatatcgta ggtgtaggtc    8100
```

-continued

```
ttccggcgtc tatactacct caagttccaa cagtttgacc tgctggctga aggtaaatgc    8160
tgcagccgaa caggctggca tgaagaaccc tcgcttcctt atttgcggcg atgattgcac    8220
cgtaatttgg aagagcgccg gagcagatgc agacaaacaa gcaatgcgtg tctttgctag    8280
ctggatgaag gtgatgggtg caccacaaga ttgtgtgcct caacccaaat acagtttgga    8340
agaattaaca tcatgctcat caaatgttac ctctggaatt accaaaagtg caagccttta    8400
ctactttctt acaagagatc ctcgtatccc ccttggcagg tgctctgccg agggtctggg    8460
atacaacccc agtgctgcgt ggattgggta tctaatacat cactacccat gtttgtgggt    8520
tagccgtgtg ttggctgtcc atttcatgga gcagatgctc tttgaggaca aacttcccga    8580
gacggtgacc tttgactggt atgggaaaaa ttatacggtg cctgtagaag atctgcccag    8640
catcattgct ggtgtgcacg gtattgaggc tttctcggtg gtgcgctaca ccaacgctga    8700
gatcctcaga gtttcccaat cactaacaga catgaccatg ccccccctgc gagcctggcg    8760
aaagaaagcc agggcggtcc tcgccagcgc caagaggcgt ggcggagcac acgcaaaatt    8820
ggctcgcttc cttctctggc atgctacatc tagacctcta ccagatttgg ataagacgag    8880
cgtggctcgg tacaccactt tcaattattg tgatgtttac tccccggagg gggatgtgtt    8940
tattacacca cagagaagat tgcagaagtt tcttgtgaag tatttggctg tcattgtttt    9000
tgccctaggg ctcattgctg ttggattagc catcagctga acccccaaat tcaaaattaa    9060
ctaacagttt tttttttttt ttttttttttt agggcagcgg caacagggga gaccccgggc    9120
ttaacgaccc cgccgatgtg agtttggcga ccatggtgga tcagaaccgt ttcgggtgaa    9180
gccatggtct gaaggggatg acgtcccttc tggctcatcc acaaaaaccg tctcgggtgg    9240
gtgaggagtc ctggctgtgt gggaagcagt cagtataatt cccgtcgtgt gtggtgacgc    9300
ctcacgacgt atttgtccgc tgtgcagagc gtagtaccaa gggctgcacc ccggtttttg    9360
ttccaagcgg agggcaaccc ccgcttggaa ttaaaaact                           9399
```

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 3

```
cgggatcccg taatacgact cactatagac cacaaacact ccagtttg              48
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4

```
gtggaattca cagcgtcata                                             20
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
tgtgaattcc actctcctac c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ttatcgattg cagcaaccat g                                              21

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 7
catggttgct gcaatcgata agctgaagag tacaataac                           39

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
gacaacagac gcttgacacg                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
ctgtcatggg agatgcgtac                                                20

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 10
cgagctcgag cacatcgcgg ggtcgttaag cccggggtct cc                       42

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
gacaacagac gcttgacacg                                                20

<210> SEQ ID NO 12
<211> LENGTH: 108
<212> TYPE: DNA
<213> ORGANISM: Artificial Sequence -continued

```
<220> FEATURE:
<223> OTHER INFORMATION: Description of Artificial Sequence:  Primer

<400> SEQUENCE: 12
ccgactcgag aattcggccc tgcaggccac aacagtctcg cgagttttta attccaagcg     60
ggggttgccc tccgcttgga acaaaaaccg gggtgcagcc cttggtac                 108

<210> SEQ ID NO 13
<211> LENGTH: 9599
<212> TYPE: DNA
<213> ORGANISM: Hepatitis C virus
<220> FEATURE:
<221> NAME/KEY: CDS
<222> LOCATION: (342)..(9377)

<400> SEQUENCE: 13
gccagccccc tgatggggc gacactccac catgaatcac tccctgtga ggaactactg      60 tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tcctttcttg gataaacccg ctcaatgcct ggagatttgg gcgtgccccc   240
gcaagactgc tagccgagta gtgttgggtc gcgaaaggcc ttgtggtact gcctgatagg   300
gtgcttgcga gtgccccggg aggtctcgta gaccgtgcac c atg agc acg aat cct   356
                                              Met Ser Thr Asn Pro
                                                1               5 aaa cct caa aga aaa acc aaa cgt aac acc aac cgt cgc cca cag gac     404
Lys Pro Gln Arg Lys Thr Lys Arg Asn Thr Asn Arg Arg Pro Gln Asp
                 10                  15                  20 gtc aag ttc ccg ggt ggc ggt cag atc gtt ggt gga gtt tac ttg ttg     452
Val Lys Phe Pro Gly Gly Gly Gln Ile Val Gly Gly Val Tyr Leu Leu
             25                  30                  35 ccg cgc agg ggc cct aga ttg ggt gtg cgc gcg acg agg aag act tcc     500
Pro Arg Arg Gly Pro Arg Leu Gly Val Arg Ala Thr Arg Lys Thr Ser
         40                  45                  50 gag cgg tcg caa cct cga ggt aga cgt cag cct atc ccc aag gca cgt     548
Glu Arg Ser Gln Pro Arg Gly Arg Arg Gln Pro Ile Pro Lys Ala Arg
     55                  60                  65 cgg ccc gag ggc agg acc tgg gct cag ccc ggg tac cct tgg ccc ctc     596
Arg Pro Glu Gly Arg Thr Trp Ala Gln Pro Gly Tyr Pro Trp Pro Leu
 70                  75                  80                  85 tat ggc aat gag ggt tgc ggg tgg gcg gga tgg ctc ctg tct ccc cgt     644
Tyr Gly Asn Glu Gly Cys Gly Trp Ala Gly Trp Leu Leu Ser Pro Arg
                 90                  95                 100 ggc tct cgg cct agc tgg ggc ccc aca gac ccc cgg cgt agg tcg cgc     692
Gly Ser Arg Pro Ser Trp Gly Pro Thr Asp Pro Arg Arg Arg Ser Arg
            105                 110                 115 aat ttg ggt aag gtc atc gat acc ctt acg tgc ggc ttc gcc gac ctc     740
Asn Leu Gly Lys Val Ile Asp Thr Leu Thr Cys Gly Phe Ala Asp Leu
        120                 125                 130 atg ggg tac ata ccg ctc gtc ggc gcc cct ctt gga ggc gct gcc agg     788
Met Gly Tyr Ile Pro Leu Val Gly Ala Pro Leu Gly Gly Ala Ala Arg
    135                 140                 145 gcc ctg gcg cat ggc gtc cgg gtt ctg gaa gac ggc gtg aac tat gca     836
Ala Leu Ala His Gly Val Arg Val Leu Glu Asp Gly Val Asn Tyr Ala
150                 155                 160                 165 aca ggg aac ctt cct ggt tgc tct ttc tct atc ttc ctt ctg gcc ctg     884
Thr Gly Asn Leu Pro Gly Cys Ser Phe Ser Ile Phe Leu Leu Ala Leu
                170                 175                 180 ctc tct tgc ctg act gtg ccc gct tca gcc tac caa gtg cgc aat tcc     932
```

```
                                                                -continued

Leu Ser Cys Leu Thr Val Pro Ala Ser Ala Tyr Gln Val Arg Asn Ser
            185                 190                 195 tcg ggg ctt tac cat gtc acc aat gat tgc cct aac tcg agt att gtg       980
Ser Gly Leu Tyr His Val Thr Asn Asp Cys Pro Asn Ser Ser Ile Val
        200                 205                 210 tac gag gcg gcc gat gcc atc ctg cac act ccg ggg tgt gtc cct tgc      1028
Tyr Glu Ala Ala Asp Ala Ile Leu His Thr Pro Gly Cys Val Pro Cys
    215                 220                 225 gtt cgc gag ggt aac gcc tcg agg tgt tgg gtg gcg gtg acc ccc acg      1076
Val Arg Glu Gly Asn Ala Ser Arg Cys Trp Val Ala Val Thr Pro Thr
230                 235                 240                 245 gtg gcc acc agg gac ggc aaa ctc ccc aca acg cag ctt cga cgt cat      1124
Val Ala Thr Arg Asp Gly Lys Leu Pro Thr Thr Gln Leu Arg Arg His
                250                 255                 260 atc gat ctg ctt gtc ggg agc gcc acc ctc tgc tcg gcc ctc tac gtg      1172
Ile Asp Leu Leu Val Gly Ser Ala Thr Leu Cys Ser Ala Leu Tyr Val
            265                 270                 275 ggg gac ctg tgc ggg tct gtc ttt ctt gtt ggt caa ctg ttt acc ttc      1220
Gly Asp Leu Cys Gly Ser Val Phe Leu Val Gly Gln Leu Phe Thr Phe
        280                 285                 290 tct ccc agg cgc cac tgg acg acg caa gac tgc aat tgt tct atc tat      1268
Ser Pro Arg Arg His Trp Thr Thr Gln Asp Cys Asn Cys Ser Ile Tyr
    295                 300                 305 ccc ggc cat ata acg ggt cat cgc atg gca tgg gat atg atg atg aac      1316
Pro Gly His Ile Thr Gly His Arg Met Ala Trp Asp Met Met Met Asn
310                 315                 320                 325 tgg tcc cct acg gca gcg ttg gtg gta gct cag ctg ctc cgg atc cca      1364
Trp Ser Pro Thr Ala Ala Leu Val Val Ala Gln Leu Leu Arg Ile Pro
                330                 335                 340 caa gcc atc atg gac atg atc gct ggt gct cac tgg gga gtc ctg gcg      1412
Gln Ala Ile Met Asp Met Ile Ala Gly Ala His Trp Gly Val Leu Ala
            345                 350                 355 ggc ata gcg tat ttc tcc atg gtg ggg aac tgg gcg aag gtc ctg gta      1460
Gly Ile Ala Tyr Phe Ser Met Val Gly Asn Trp Ala Lys Val Leu Val
        360                 365                 370 gtg ctg ctg cta ttt gcc ggc gtc gac gcg gaa acc cac gtc acc ggg      1508
Val Leu Leu Leu Phe Ala Gly Val Asp Ala Glu Thr His Val Thr Gly
    375                 380                 385 gga aat gcc ggc cgc acc acg gct ggg ctt gtt ggt ctc ctt aca cca      1556
Gly Asn Ala Gly Arg Thr Thr Ala Gly Leu Val Gly Leu Leu Thr Pro
390                 395                 400                 405 ggc gcc aag cag aac atc caa ctg atc aac acc aac ggc agt tgg cac      1604
Gly Ala Lys Gln Asn Ile Gln Leu Ile Asn Thr Asn Gly Ser Trp His
                410                 415                 420 atc aat agc acg gcc ttg aat tgc aat gaa agc ctt aac acc ggc tgg      1652
Ile Asn Ser Thr Ala Leu Asn Cys Asn Glu Ser Leu Asn Thr Gly Trp
            425                 430                 435 tta gca ggg ctc ttc tat caa cac aaa ttc aac tct tca ggc tgt cct      1700
Leu Ala Gly Leu Phe Tyr Gln His Lys Phe Asn Ser Ser Gly Cys Pro
        440                 445                 450 gag agg ttg gcc agc tgc cga cgc ctt acc gat ttt gcc cag ggc tgg      1748
Glu Arg Leu Ala Ser Cys Arg Arg Leu Thr Asp Phe Ala Gln Gly Trp
    455                 460                 465 ggt cct atc agt tat gcc aac gga agc ggc ctc gac gaa cgc ccc tac      1796
Gly Pro Ile Ser Tyr Ala Asn Gly Ser Gly Leu Asp Glu Arg Pro Tyr
470                 475                 480                 485 tgc tgg cac tac cct cca aga cct tgt ggc att gtg ccc gca aag agc      1844
Cys Trp His Tyr Pro Pro Arg Pro Cys Gly Ile Val Pro Ala Lys Ser
                490                 495                 500
```

-continued

| | | |
|---|---|---|
| gtg tgt ggc ccg gta tat tgc ttc act ccc agc ccc gtg gtg gtg gga<br>Val Cys Gly Pro Val Tyr Cys Phe Thr Pro Ser Pro Val Val Val Gly<br>505                    510                    515 | 1892 |
| acg acc gac agg tcg ggc gcg cct acc tac agc tgg ggt gca aat gat<br>Thr Thr Asp Arg Ser Gly Ala Pro Thr Tyr Ser Trp Gly Ala Asn Asp<br>520                    525                    530 | 1940 |
| acg gat gtc ttc gtc ctt aac aac acc agg cca ccg ctg ggc aat tgg<br>Thr Asp Val Phe Val Leu Asn Asn Thr Arg Pro Pro Leu Gly Asn Trp<br>535                    540                    545 | 1988 |
| ttc ggt tgt acc tgg atg aac tca act gga ttc acc aaa gtg tgc gga<br>Phe Gly Cys Thr Trp Met Asn Ser Thr Gly Phe Thr Lys Val Cys Gly<br>550                    555                    560                    565 | 2036 |
| gcg ccc cct tgt gtc atc gga ggg gtg ggc aac aac acc ttg ctc tgc<br>Ala Pro Pro Cys Val Ile Gly Gly Val Gly Asn Asn Thr Leu Leu Cys<br>570                    575                    580 | 2084 |
| ccc act gat tgc ttc cgc aaa cat ccg gaa gcc aca tac tct cgg tgc<br>Pro Thr Asp Cys Phe Arg Lys His Pro Glu Ala Thr Tyr Ser Arg Cys<br>585                    590                    595 | 2132 |
| ggc tcc ggt ccc tgg att aca ccc agg tgc atg gtc gac tac ccg tat<br>Gly Ser Gly Pro Trp Ile Thr Pro Arg Cys Met Val Asp Tyr Pro Tyr<br>600                    605                    610 | 2180 |
| agg ctt tgg cac tat cct tgt acc atc aat tac acc ata ttc aaa gtc<br>Arg Leu Trp His Tyr Pro Cys Thr Ile Asn Tyr Thr Ile Phe Lys Val<br>615                    620                    625 | 2228 |
| agg atg tac gtg gga ggg gtc gag cac agg ctg gaa gcg gcc tgc aac<br>Arg Met Tyr Val Gly Gly Val Glu His Arg Leu Glu Ala Ala Cys Asn<br>630                    635                    640                    645 | 2276 |
| tgg acg cgg ggc gaa cgc tgt gat ctg gaa gac agg gac agg tcc gag<br>Trp Thr Arg Gly Glu Arg Cys Asp Leu Glu Asp Arg Asp Arg Ser Glu<br>650                    655                    660 | 2324 |
| ctc agc ccg ttg ctg ctg tcc acc aca cag tgg cag gtc ctt ccg tgt<br>Leu Ser Pro Leu Leu Leu Ser Thr Thr Gln Trp Gln Val Leu Pro Cys<br>665                    670                    675 | 2372 |
| tct ttc acg acc ctg cca gcc ttg tcc acc ggc ctc atc cac ctc cac<br>Ser Phe Thr Thr Leu Pro Ala Leu Ser Thr Gly Leu Ile His Leu His<br>680                    685                    690 | 2420 |
| cag aac att gtg gac gtg cag tac ttg tac ggg gta ggg tca agc atc<br>Gln Asn Ile Val Asp Val Gln Tyr Leu Tyr Gly Val Gly Ser Ser Ile<br>695                    700                    705 | 2468 |
| gcg tcc tgg gcc att aag tgg gag tac gtc gtt ctc ctg ttc ctt ctg<br>Ala Ser Trp Ala Ile Lys Trp Glu Tyr Val Val Leu Leu Phe Leu Leu<br>710                    715                    720                    725 | 2516 |
| ctt gca gac gcg cgc gtc tgc tcc tgc ttg tgg atg atg tta ctc ata<br>Leu Ala Asp Ala Arg Val Cys Ser Cys Leu Trp Met Met Leu Leu Ile<br>730                    735                    740 | 2564 |
| tcc caa gcg gag gcg gct ttg gag aac ctc gta ata ctc aat gca gca<br>Ser Gln Ala Glu Ala Ala Leu Glu Asn Leu Val Ile Leu Asn Ala Ala<br>745                    750                    755 | 2612 |
| tcc ctg gcc ggg acg cac ggt ctt gtg tcc ttc ctc gtg ttc ttc tgc<br>Ser Leu Ala Gly Thr His Gly Leu Val Ser Phe Leu Val Phe Phe Cys<br>760                    765                    770 | 2660 |
| ttt gcg tgg tat ctg aag ggt agg tgg gtg ccc gga gcg gtc tac gcc<br>Phe Ala Trp Tyr Leu Lys Gly Arg Trp Val Pro Gly Ala Val Tyr Ala<br>775                    780                    785 | 2708 |
| ctc tac ggg atg tgg cct ctc ctg ctc ctg ctg gcg ttg cct cag<br>Leu Tyr Gly Met Trp Pro Leu Leu Leu Leu Leu Ala Leu Pro Gln<br>790                    795                    800                    805 | 2756 |
| cgg gca tac gca ctg gac acg gag gtg gcc gcg tcg tgt ggc ggc gtt<br>Arg Ala Tyr Ala Leu Asp Thr Glu Val Ala Ala Ser Cys Gly Gly Val<br>810                    815                    820 | 2804 |

-continued

| | |
|---|---|
| gtt ctt gtc ggg tta atg gcg ctg act ctg tcg cca tat tac aag cgc<br>Val Leu Val Gly Leu Met Ala Leu Thr Leu Ser Pro Tyr Tyr Lys Arg<br>825      830      835 | 2852 |
| tat atc agc tgg tgc atg tgg tgg ctt cag tat ttt ctg acc aga gta<br>Tyr Ile Ser Trp Cys Met Trp Trp Leu Gln Tyr Phe Leu Thr Arg Val<br>   840      845      850 | 2900 |
| gaa gcg caa ctg cac gtg tgg gtt ccc ccc ctc aac gtc cgg ggg ggg<br>Glu Ala Gln Leu His Val Trp Val Pro Pro Leu Asn Val Arg Gly Gly<br>855      860      865 | 2948 |
| cgc gat gcc gtc atc tta ctc atg tgt gta gta cac ccg acc ctg gta<br>Arg Asp Ala Val Ile Leu Leu Met Cys Val Val His Pro Thr Leu Val<br>870      875      880      885 | 2996 |
| ttt gac atc acc aaa cta ctc ctg gcc atc ttc gga ccc ctt tgg att<br>Phe Asp Ile Thr Lys Leu Leu Leu Ala Ile Phe Gly Pro Leu Trp Ile<br>   890      895      900 | 3044 |
| ctt caa gcc agt ttg ctt aaa gtc ccc tac ttc gtg cgc gtt caa ggc<br>Leu Gln Ala Ser Leu Leu Lys Val Pro Tyr Phe Val Arg Val Gln Gly<br>905      910      915 | 3092 |
| ctt ctc cgg atc tgc gcg cta gcg cgg aag ata gcc gga ggt cat tac<br>Leu Leu Arg Ile Cys Ala Leu Ala Arg Lys Ile Ala Gly Gly His Tyr<br>920      925      930 | 3140 |
| gtg caa atg gcc atc atc aag tta ggg gcg ctt act ggc acc tat gtg<br>Val Gln Met Ala Ile Ile Lys Leu Gly Ala Leu Thr Gly Thr Tyr Val<br>935      940      945 | 3188 |
| tat aac cat ctc acc cct ctt cga gac tgg gcg cac aac ggc ctg cga<br>Tyr Asn His Leu Thr Pro Leu Arg Asp Trp Ala His Asn Gly Leu Arg<br>950      955      960      965 | 3236 |
| gat ctg gcc gtg gct gtg gaa cca gtc gtc ttc tcc cga atg gag acc<br>Asp Leu Ala Val Ala Val Glu Pro Val Val Phe Ser Arg Met Glu Thr<br>   970      975      980 | 3284 |
| aag ctc atc acg tgg ggg gca gat acc gcc gcg tgc ggt gac atc atc<br>Lys Leu Ile Thr Trp Gly Ala Asp Thr Ala Ala Cys Gly Asp Ile Ile<br>985      990      995 | 3332 |
| aac ggc ttg ccc gtc tct gcc cgt agg ggc cag gag ata ctg ctt ggg<br>Asn Gly Leu Pro Val Ser Ala Arg Arg Gly Gln Glu Ile Leu Leu Gly<br>1000      1005      1010 | 3380 |
| cca gcc gac gga atg gtc tcc aag ggg tgg agg ttg ctg gcg ccc atc<br>Pro Ala Asp Gly Met Val Ser Lys Gly Trp Arg Leu Leu Ala Pro Ile<br>1015      1020      1025 | 3428 |
| acg gcg tac gcc cag cag acg aga ggc ctc cta ggg tgt ata atc acc<br>Thr Ala Tyr Ala Gln Gln Thr Arg Gly Leu Leu Gly Cys Ile Ile Thr<br>1030      1035      1040      1045 | 3476 |
| agc ctg act ggc cgg gac aaa aac caa gtg gag ggt gag gtc cag atc<br>Ser Leu Thr Gly Arg Asp Lys Asn Gln Val Glu Gly Glu Val Gln Ile<br>1050      1055      1060 | 3524 |
| gtg tca act gct acc caa acc ttc ctg gca acg tgc atc aat ggg gta<br>Val Ser Thr Ala Thr Gln Thr Phe Leu Ala Thr Cys Ile Asn Gly Val<br>1065      1070      1075 | 3572 |
| tgc tgg act gtc tac cac ggg gcc gga acg agg acc atc gca tca ccc<br>Cys Trp Thr Val Tyr His Gly Ala Gly Thr Arg Thr Ile Ala Ser Pro<br>1080      1085      1090 | 3620 |
| aag ggt cct gtc atc cag atg tat acc aat gtg gac caa gac ctt gtg<br>Lys Gly Pro Val Ile Gln Met Tyr Thr Asn Val Asp Gln Asp Leu Val<br>1095      1100      1105 | 3668 |
| ggc tgg ccc gct cct caa ggt tcc cgc tca ttg aca ccc tgt acc tgc<br>Gly Trp Pro Ala Pro Gln Gly Ser Arg Ser Leu Thr Pro Cys Thr Cys<br>1110      1115      1120      1125 | 3716 |
| ggc tcc tcg gac ctt tac ctg gtc acg agg cac gcc gat gtc att ccc<br>Gly Ser Ser Asp Leu Tyr Leu Val Thr Arg His Ala Asp Val Ile Pro | 3764 |

-continued

|  |  |  |  |  |
|---|---|---|---|---|
| | 1130 | 1135 | 1140 | |
| gtg cgc cgg cga ggt gat agc agg ggt agc ctg ctt tcg ccc cgg ccc<br>Val Arg Arg Arg Gly Asp Ser Arg Gly Ser Leu Leu Ser Pro Arg Pro<br>1145 1150 1155 | | | | 3812 |
| att tcc tac ttg aaa ggc tcc tcg ggg ggt ccg ctg ttg tgc ccc gcg<br>Ile Ser Tyr Leu Lys Gly Ser Ser Gly Gly Pro Leu Leu Cys Pro Ala<br>1160 1165 1170 | | | | 3860 |
| gga cac gcc gtg ggc cta ttc agg gcc gcg gtg tgc acc cgt gga gtg<br>Gly His Ala Val Gly Leu Phe Arg Ala Ala Val Cys Thr Arg Gly Val<br>1175 1180 1185 | | | | 3908 |
| gct aaa gcg gtg gac ttt atc cct gtg gag aac cta ggg aca acc atg<br>Ala Lys Ala Val Asp Phe Ile Pro Val Glu Asn Leu Gly Thr Thr Met<br>1190 1195 1200 1205 | | | | 3956 |
| aga tcc ccg gtg ttc acg gac aac tcc tct cca cca gca gtg ccc cag<br>Arg Ser Pro Val Phe Thr Asp Asn Ser Ser Pro Pro Ala Val Pro Gln<br>1210 1215 1220 | | | | 4004 |
| agc ttc cag gtg gcc cac ctg cat gct ccc acc ggc agc ggt aag agc<br>Ser Phe Gln Val Ala His Leu His Ala Pro Thr Gly Ser Gly Lys Ser<br>1225 1230 1235 | | | | 4052 |
| acc aag gtc ccg gct gcg tac gca gcc cag ggc tac aag gtg ttg gtg<br>Thr Lys Val Pro Ala Ala Tyr Ala Ala Gln Gly Tyr Lys Val Leu Val<br>1240 1245 1250 | | | | 4100 |
| ctc aac ccc tct gtt gct gca acg ctg ggc ttt ggt gct tac atg tcc<br>Leu Asn Pro Ser Val Ala Ala Thr Leu Gly Phe Gly Ala Tyr Met Ser<br>1255 1260 1265 | | | | 4148 |
| aag gcc cat ggg gtt gat cct aat atc agg acc ggg gtg aga aca att<br>Lys Ala His Gly Val Asp Pro Asn Ile Arg Thr Gly Val Arg Thr Ile<br>1270 1275 1280 1285 | | | | 4196 |
| acc act ggc agc ccc atc acg tac tcc acc tac ggc aag ttc ctt gcc<br>Thr Thr Gly Ser Pro Ile Thr Tyr Ser Thr Tyr Gly Lys Phe Leu Ala<br>1290 1295 1300 | | | | 4244 |
| gac ggc ggg tgc tca gga ggt gct tat gac ata ata att tgt gac gag<br>Asp Gly Gly Cys Ser Gly Gly Ala Tyr Asp Ile Ile Ile Cys Asp Glu<br>1305 1310 1315 | | | | 4292 |
| tgc cac tcc acg gat gcc aca tcc atc ttg ggc atc ggc act gtc ctt<br>Cys His Ser Thr Asp Ala Thr Ser Ile Leu Gly Ile Gly Thr Val Leu<br>1320 1325 1330 | | | | 4340 |
| gac caa gca gag act gcg ggg gcg aga ctg gtt gtg ctc gcc act gct<br>Asp Gln Ala Glu Thr Ala Gly Ala Arg Leu Val Val Leu Ala Thr Ala<br>1335 1340 1345 | | | | 4388 |
| acc cct ccg ggc tcc gtc act gtg tcc cat cct aac atc gag gag gtt<br>Thr Pro Pro Gly Ser Val Thr Val Ser His Pro Asn Ile Glu Glu Val<br>1350 1355 1360 1365 | | | | 4436 |
| gct ctg tcc acc acc gga gag atc ccc ttt tac ggc aag gct atc ccc<br>Ala Leu Ser Thr Thr Gly Glu Ile Pro Phe Tyr Gly Lys Ala Ile Pro<br>1370 1375 1380 | | | | 4484 |
| ctc gag gtg atc aag ggg gga aga cat ctc atc ttc tgc cac tca aag<br>Leu Glu Val Ile Lys Gly Gly Arg His Leu Ile Phe Cys His Ser Lys<br>1385 1390 1395 | | | | 4532 |
| aag aag tgc gac gag ctc gcc gcg aag ctg tcc gca ttg ggc atc aat<br>Lys Lys Cys Asp Glu Leu Ala Ala Lys Leu Val Ala Leu Gly Ile Asn<br>1400 1405 1410 | | | | 4580 |
| gcc gtg gcc tac tac cgc ggt ctt gac gtg tct gtc atc ccg acc agc<br>Ala Val Ala Tyr Tyr Arg Gly Leu Asp Val Ser Val Ile Pro Thr Ser<br>1415 1420 1425 | | | | 4628 |
| ggc gat gtt gtc gtc gtg tcg acc gat gct ctc atg act ggc ttt acc<br>Gly Asp Val Val Val Val Ser Thr Asp Ala Leu Met Thr Gly Phe Thr<br>1430 1435 1440 1445 | | | | 4676 |
| ggc gac ttc gac tct gtg ata gac tgc aac acg tgt gtc act cag aca<br>| | | | 4724 |

```
                                                                -continued

Gly Asp Phe Asp Ser Val Ile Asp Cys Asn Thr Cys Val Thr Gln Thr
            1450                1455                1460 gtc gat ttc agc ctt gac cct acc ttt acc att gag aca acc acg ctc    4772
Val Asp Phe Ser Leu Asp Pro Thr Phe Thr Ile Glu Thr Thr Thr Leu
1465                1470                1475 ccc cag gat gct gtc tcc agg act caa cgc cgg ggc agg act ggc agg    4820
Pro Gln Asp Ala Val Ser Arg Thr Gln Arg Arg Gly Arg Thr Gly Arg
        1480                1485                1490 ggg aag cca ggc atc tat aga ttt gtg gca ccg ggg gag cgc ccc tcc    4868
Gly Lys Pro Gly Ile Tyr Arg Phe Val Ala Pro Gly Glu Arg Pro Ser
    1495                1500                1505 ggc atg ttc gac tcg tcc gtc ctc tgt gag tgc tat gac gcg ggc tgt    4916
Gly Met Phe Asp Ser Ser Val Leu Cys Glu Cys Tyr Asp Ala Gly Cys
1510                1515                1520                1525 gct tgg tat gag ctc acg ccc gcc gag act aca gtt agg cta cga gcg    4964
Ala Trp Tyr Glu Leu Thr Pro Ala Glu Thr Thr Val Arg Leu Arg Ala
            1530                1535                1540 tac atg aac acc ccg ggg ctt ccc gtg tgc cag gac cat ctt gaa ttt    5012
Tyr Met Asn Thr Pro Gly Leu Pro Val Cys Gln Asp His Leu Glu Phe
        1545                1550                1555 tgg gag ggc gtc ttt acg ggc ctc act cat ata gat gcc cac ttt tta    5060
Trp Glu Gly Val Phe Thr Gly Leu Thr His Ile Asp Ala His Phe Leu
    1560                1565                1570 tcc cag aca aag cag agt ggg gag aac ttt cct tac ctg gta gcg tac    5108
Ser Gln Thr Lys Gln Ser Gly Glu Asn Phe Pro Tyr Leu Val Ala Tyr
1575                1580                1585 caa gcc acc gtg tgc gct agg gct caa gcc cct ccc cca tcg tgg gac    5156
Gln Ala Thr Val Cys Ala Arg Ala Gln Ala Pro Pro Pro Ser Trp Asp
1590                1595                1600                1605 cag atg tgg aag tgt ttg atc cgc ctt aaa ccc acc ctc cat ggg cca    5204
Gln Met Trp Lys Cys Leu Ile Arg Leu Lys Pro Thr Leu His Gly Pro
            1610                1615                1620 aca ccc ctg cta tac aga ctg ggc gct gtt cag aat gaa gtc acc ctg    5252
Thr Pro Leu Leu Tyr Arg Leu Gly Ala Val Gln Asn Glu Val Thr Leu
        1625                1630                1635 acg cac cca atc acc aaa tac atc atg aca tgc atg tcg gcc gac ctg    5300
Thr His Pro Ile Thr Lys Tyr Ile Met Thr Cys Met Ser Ala Asp Leu
    1640                1645                1650 gag gtc gtc acg agc acc tgg gtg ctc gtt ggc ggc gtc ctg gct gct    5348
Glu Val Val Thr Ser Thr Trp Val Leu Val Gly Gly Val Leu Ala Ala
1655                1660                1665 ctg gcc gcg tat tgc ctg tca aca ggc tgc gtg gtc ata gtg ggc agg    5396
Leu Ala Ala Tyr Cys Leu Ser Thr Gly Cys Val Val Ile Val Gly Arg
1670                1675                1680                1685 atc gtc ttg tcc ggg aag ccg gca att ata cct gac agg gag gtt ctc    5444
Ile Val Leu Ser Gly Lys Pro Ala Ile Ile Pro Asp Arg Glu Val Leu
            1690                1695                1700 tac cag gag ttc gat gag atg gaa gag tgc tct cag cac tta ccg tac    5492
Tyr Gln Glu Phe Asp Glu Met Glu Glu Cys Ser Gln His Leu Pro Tyr
        1705                1710                1715 atc gag caa ggg atg atg ctc gct gag cag ttc aag cag aag gcc ctc    5540
Ile Glu Gln Gly Met Met Leu Ala Glu Gln Phe Lys Gln Lys Ala Leu
    1720                1725                1730 ggc ctc ctg cag acc gcg tcc cgc cat gca gag gtt atc acc cct gct    5588
Gly Leu Leu Gln Thr Ala Ser Arg His Ala Glu Val Ile Thr Pro Ala
1735                1740                1745 gtc cag acc aac tgg cag aaa ctc gag gtc ttt tgg gcg aag cac atg    5636
Val Gln Thr Asn Trp Gln Lys Leu Glu Val Phe Trp Ala Lys His Met
1750                1755                1760                1765
```

-continued

| | |
|---|---|
| tgg aat ttc atc agt ggg ata caa tac ttg gcg ggc ctg tca acg ctg<br>Trp Asn Phe Ile Ser Gly Ile Gln Tyr Leu Ala Gly Leu Ser Thr Leu<br>                   1770                         1775                     1780 | 5684 |
| cct ggt aac ccc gcc att gct tca ttg atg gct ttt aca gct gcc gtc<br>Pro Gly Asn Pro Ala Ile Ala Ser Leu Met Ala Phe Thr Ala Ala Val<br>   1785                       1790                       1795 | 5732 |
| acc agc cca cta acc act ggc caa acc ctc ctc ttc aac ata ttg ggg<br>Thr Ser Pro Leu Thr Thr Gly Gln Thr Leu Leu Phe Asn Ile Leu Gly<br>              1800                       1805                   1810 | 5780 |
| ggg tgg gtg gct gcc cag ctc gcc gcc ccc ggt gcc gct act gcc ttt<br>Gly Trp Val Ala Ala Gln Leu Ala Ala Pro Gly Ala Ala Thr Ala Phe<br>   1815                       1820                       1825 | 5828 |
| gtg ggt gct ggc cta gct ggc gcc gcc atc ggc agc gtt gga ctg ggg<br>Val Gly Ala Gly Leu Ala Gly Ala Ala Ile Gly Ser Val Gly Leu Gly<br>1830                   1835                     1840                   1845 | 5876 |
| aag gtc ctc gtg gac att ctt gca ggg tat ggc gcg ggc gtg gcg gga<br>Lys Val Leu Val Asp Ile Leu Ala Gly Tyr Gly Ala Gly Val Ala Gly<br>              1850                       1855                   1860 | 5924 |
| gct ctt gta gca ttc aag atc atg agc ggt gag gtc ccc tcc acg gag<br>Ala Leu Val Ala Phe Lys Ile Met Ser Gly Glu Val Pro Ser Thr Glu<br>   1865                       1870                       1875 | 5972 |
| gac ctg gtc aat ctg ctg ccc gcc atc ctc tcg cct gga gcc ctt gta<br>Asp Leu Val Asn Leu Leu Pro Ala Ile Leu Ser Pro Gly Ala Leu Val<br>              1880                       1885                   1890 | 6020 |
| gtc ggt gtg gtc tgc gca gca ata ctg cgc cgg cac gtt ggc ccg ggc<br>Val Gly Val Val Cys Ala Ala Ile Leu Arg Arg His Val Gly Pro Gly<br>   1895                       1900                       1905 | 6068 |
| gag ggg gca gtg caa tgg atg aac cgg cta ata gcc ttc gcc tcc cgg<br>Glu Gly Ala Val Gln Trp Met Asn Arg Leu Ile Ala Phe Ala Ser Arg<br>1910                   1915                     1920                   1925 | 6116 |
| ggg aac cat gtt tcc ccc acg cac tac gtg ccg gag agc gat gca gcc<br>Gly Asn His Val Ser Pro Thr His Tyr Val Pro Glu Ser Asp Ala Ala<br>              1930                       1935                   1940 | 6164 |
| gcc cgc gtc act gcc ata ctc agc agc ctc act gta acc cag ctc ctg<br>Ala Arg Val Thr Ala Ile Leu Ser Ser Leu Thr Val Thr Gln Leu Leu<br>   1945                       1950                       1955 | 6212 |
| agg cga ctg cat cag tgg ata agc tcg gag tgt acc act cca tgc tcc<br>Arg Arg Leu His Gln Trp Ile Ser Ser Glu Cys Thr Thr Pro Cys Ser<br>              1960                       1965                   1970 | 6260 |
| ggt tcc tgg cta agg gac atc tgg gac tgg ata tgc gag gtg ctg agc<br>Gly Ser Trp Leu Arg Asp Ile Trp Asp Trp Ile Cys Glu Val Leu Ser<br>   1975                       1980                       1985 | 6308 |
| gac ttt aag acc tgg ctg aaa gcc aag ctc atg cca caa ctg cct ggg<br>Asp Phe Lys Thr Trp Leu Lys Ala Lys Leu Met Pro Gln Leu Pro Gly<br>1990                   1995                     2000                   2005 | 6356 |
| att ccc ttt gtg tcc tgc cag cgc ggg tat agg ggg gtc tgg cga gga<br>Ile Pro Phe Val Ser Cys Gln Arg Gly Tyr Arg Gly Val Trp Arg Gly<br>              2010                       2015                   2020 | 6404 |
| gac ggc att atg cac act cgc tgc cac tgt gga gct gag atc act gga<br>Asp Gly Ile Met His Thr Arg Cys His Cys Gly Ala Glu Ile Thr Gly<br>   2025                       2030                       2035 | 6452 |
| cat gtc aaa aac ggg acg atg agg atc gtc ggt cct agg acc tgc agg<br>His Val Lys Asn Gly Thr Met Arg Ile Val Gly Pro Arg Thr Cys Arg<br>              2040                       2045                   2050 | 6500 |
| aac atg tgg agt ggg acg ttc ccc att aac gcc tac acc acg ggc ccc<br>Asn Met Trp Ser Gly Thr Phe Pro Ile Asn Ala Tyr Thr Thr Gly Pro<br>   2055                       2060                       2065 | 6548 |
| tgt act ccc ctt cct gcg ccg aac tat aag ttc gcg ctg tgg agg gtg<br>Cys Thr Pro Leu Pro Ala Pro Asn Tyr Lys Phe Ala Leu Trp Arg Val<br>2070                   2075                     2080                   2085 | 6596 |

-continued

```
tct gca gag gaa tac gtg gag ata agg cgg gtg ggg gac ttc cac tac    6644
Ser Ala Glu Glu Tyr Val Glu Ile Arg Arg Val Gly Asp Phe His Tyr
            2090                2095                2100 gta tcg ggt atg act act gac aat ctt aaa tgc ccg tgc cag atc cca    6692
Val Ser Gly Met Thr Thr Asp Asn Leu Lys Cys Pro Cys Gln Ile Pro
        2105                2110                2115 tcg ccc gaa ttt ttc aca gaa ttg gac ggg gtg cgc cta cac agg ttt    6740
Ser Pro Glu Phe Phe Thr Glu Leu Asp Gly Val Arg Leu His Arg Phe
        2120                2125                2130 gcg ccc cct tgc aag ccc ttg ctg cgg gag gag gta tca ttc aga gta    6788
Ala Pro Pro Cys Lys Pro Leu Leu Arg Glu Glu Val Ser Phe Arg Val
        2135                2140                2145 gga ctc cac gag tac ccg gtg ggg tcg caa tta cct tgc gag ccc gaa    6836
Gly Leu His Glu Tyr Pro Val Gly Ser Gln Leu Pro Cys Glu Pro Glu
2150                2155                2160                2165 ccg gac gta gcc gtg ttg acg tcc atg ctc act gat ccc tcc cat ata    6884
Pro Asp Val Ala Val Leu Thr Ser Met Leu Thr Asp Pro Ser His Ile
        2170                2175                2180 aca gca gag gcg gcc ggg aga agg ttg gcg aga ggg tca ccc cct tct    6932
Thr Ala Glu Ala Ala Gly Arg Arg Leu Ala Arg Gly Ser Pro Pro Ser
        2185                2190                2195 atg gcc agc tcc tcg gct agc cag ctg tcc gct cca tct ctc aag gca    6980
Met Ala Ser Ser Ser Ala Ser Gln Leu Ser Ala Pro Ser Leu Lys Ala
        2200                2205                2210 act tgc acc gcc aac cat gac tcc cct gac gcc gag ctc ata gag gct    7028
Thr Cys Thr Ala Asn His Asp Ser Pro Asp Ala Glu Leu Ile Glu Ala
        2215                2220                2225 aac ctc ctg tgg agg cag gag atg ggc ggc aac atc acc agg gtt gag    7076
Asn Leu Leu Trp Arg Gln Glu Met Gly Gly Asn Ile Thr Arg Val Glu
2230                2235                2240                2245 tca gag aac aaa gtg gtg att ctg gac tcc ttc gat ccg ctt gtg gca    7124
Ser Glu Asn Lys Val Val Ile Leu Asp Ser Phe Asp Pro Leu Val Ala
        2250                2255                2260 gag gag gat gag cgg gag gtc tcc gta cct gca gaa att ctg cgg aag    7172
Glu Glu Asp Glu Arg Glu Val Ser Val Pro Ala Glu Ile Leu Arg Lys
        2265                2270                2275 tct cgg aga ttc gcc cgg gcc ctg ccc gtc tgg gcg cgg ccg gac tac    7220
Ser Arg Arg Phe Ala Arg Ala Leu Pro Val Trp Ala Arg Pro Asp Tyr
        2280                2285                2290 aac ccc ccg cta gta gag acg tgg aaa aag cct gac tac gaa cca cct    7268
Asn Pro Pro Leu Val Glu Thr Trp Lys Lys Pro Asp Tyr Glu Pro Pro
        2295                2300                2305 gtg gtc cat ggc tgc ccg cta cca cct cca cgg tcc cct cct gtg cct    7316
Val Val His Gly Cys Pro Leu Pro Pro Pro Arg Ser Pro Pro Val Pro
2310                2315                2320                2325 ccg cct cgg aaa aag cgt acg gtg gtc ctc acc gaa tca acc cta tct    7364
Pro Pro Arg Lys Lys Arg Thr Val Val Leu Thr Glu Ser Thr Leu Ser
        2330                2335                2340 act gcc ttg gcc gag ctt gcc acc aaa agt ttt ggc agc tcc tca act    7412
Thr Ala Leu Ala Glu Leu Ala Thr Lys Ser Phe Gly Ser Ser Ser Thr
        2345                2350                2355 tcc ggc att acg ggc gac aat acg aca aca tcc tct gag ccc gcc cct    7460
Ser Gly Ile Thr Gly Asp Asn Thr Thr Thr Ser Ser Glu Pro Ala Pro
        2360                2365                2370 tct ggc tgc ccc ccc gac tcc gac gtt gag tcc tat tct tcc atg ccc    7508
Ser Gly Cys Pro Pro Asp Ser Asp Val Glu Ser Tyr Ser Ser Met Pro
        2375                2380                2385 ccc ctg gag ggg gag cct ggg gat ccg gat ctc agc gac ggg tca tgg    7556
Pro Leu Glu Gly Glu Pro Gly Asp Pro Asp Leu Ser Asp Gly Ser Trp
```

-continued

```
       2390                2395                2400                2405
tcg acg gtc agt agt ggg gcc gac acg gaa gat gtc gtg tgc tgc tca      7604
Ser Thr Val Ser Ser Gly Ala Asp Thr Glu Asp Val Val Cys Cys Ser
                     2410                2415                2420 atg tct tat tcc tgg aca ggc gca ctc gtc acc ccg tgc gct gcg aa      7652
Met Ser Tyr Ser Trp Thr Gly Ala Leu Val Thr Pro Cys Ala Ala Glu
             2425                2430                2435 gaa caa aaa ctg ccc atc aac gca ctg agc aac tcg ttg cta cgc cat      7700
Glu Gln Lys Leu Pro Ile Asn Ala Leu Ser Asn Ser Leu Leu Arg His
         2440                2445                2450 cac aat ctg gtg tat tcc acc act tca cgc agt gct tgc caa agg cag      7748
His Asn Leu Val Tyr Ser Thr Thr Ser Arg Ser Ala Cys Gln Arg Gln
     2455                2460                2465 aag aaa gtc aca ttt gac aga ctg caa gtt ctg gac agc cat tac cag      7796
Lys Lys Val Thr Phe Asp Arg Leu Gln Val Leu Asp Ser His Tyr Gln
2470                2475                2480                2485 gac gtg ctc aag gag gtc aaa gca gcg gcg tca aaa gtg aag gct aac      7844
Asp Val Leu Lys Glu Val Lys Ala Ala Ala Ser Lys Val Lys Ala Asn
                 2490                2495                2500 ttg cta tcc gta gag gaa gct tgc agc ctg acg ccc cat tca gcc          7892
Leu Leu Ser Val Glu Glu Ala Cys Ser Leu Thr Pro Pro His Ser Ala
             2505                2510                2515 aaa tcc aag ttt ggc tat ggg gca aaa gac gtc cgt tgc cat gcc aga      7940
Lys Ser Lys Phe Gly Tyr Gly Ala Lys Asp Val Arg Cys His Ala Arg
         2520                2525                2530 aag gcc gta gcc cac atc aac tcc gtg tgg aaa gac ctt ctg gaa gac      7988
Lys Ala Val Ala His Ile Asn Ser Val Trp Lys Asp Leu Leu Glu Asp
     2535                2540                2545 agt gta aca cca ata gac act acc atc atg gcc aag aac gag gtt ttc      8036
Ser Val Thr Pro Ile Asp Thr Thr Ile Met Ala Lys Asn Glu Val Phe
2550                2555                2560                2565 tgc gtt cag cct gag aag ggg ggt cgt aag cca gct cgt ctc atc gtg      8084
Cys Val Gln Pro Glu Lys Gly Gly Arg Lys Pro Ala Arg Leu Ile Val
                 2570                2575                2580 ttc ccc gac ctg ggc gtg cgc gtg tgc gag aag atg gcc ctg tac gac      8132
Phe Pro Asp Leu Gly Val Arg Val Cys Glu Lys Met Ala Leu Tyr Asp
             2585                2590                2595 gtg gtt agc aag ctc ccc ctg gcc gtg atg gga agc tcc tac gga ttc      8180
Val Val Ser Lys Leu Pro Leu Ala Val Met Gly Ser Ser Tyr Gly Phe
         2600                2605                2610 caa tac tca cca gga cag cgg gtt gaa ttc ctc gtg caa gcg tgg aag      8228
Gln Tyr Ser Pro Gly Gln Arg Val Glu Phe Leu Val Gln Ala Trp Lys
     2615                2620                2625 tcc aag aag acc ccg atg ggg ttc tcg tat gat acc cgc tgt ttt gac      8276
Ser Lys Lys Thr Pro Met Gly Phe Ser Tyr Asp Thr Arg Cys Phe Asp
2630                2635                2640                2645 tcc aca gtc act gag agc gac atc cgt acg gag gag gca att tac caa      8324
Ser Thr Val Thr Glu Ser Asp Ile Arg Thr Glu Glu Ala Ile Tyr Gln
                 2650                2655                2660 tgt tgt gac ctg gac ccc caa gcc cgc gtg gcc atc aag tcc ctc act      8372
Cys Cys Asp Leu Asp Pro Gln Ala Arg Val Ala Ile Lys Ser Leu Thr
             2665                2670                2675 gag agg ctt tat gtt ggg ggc cct ctt acc aat tca ggg gga aac          8420
Glu Arg Leu Tyr Val Gly Gly Pro Leu Thr Asn Ser Arg Gly Glu Asn
         2680                2685                2690 tgc ggc tac cgc agg tgc cgc gcg agc ggc gta ctg aca act agc tgt      8468
Cys Gly Tyr Arg Arg Cys Arg Ala Ser Gly Val Leu Thr Thr Ser Cys
     2695                2700                2705 ggt aac acc ctc act tgc tac atc aag gcc cgg gca gcc tgt cga gcc      8516
```

```
                                                               -continued
Gly Asn Thr Leu Thr Cys Tyr Ile Lys Ala Arg Ala Ala Cys Arg Ala
2710                2715                2720                2725 gca ggg ctc cag gac tgc acc atg ctc gtg tgt ggc gac gac tta gtc      8564
Ala Gly Leu Gln Asp Cys Thr Met Leu Val Cys Gly Asp Asp Leu Val
                    2730                2735                2740 gtt atc tgt gaa agt gcg ggg gtc cag gag gac gcg gcg agc ctg aga      8612
Val Ile Cys Glu Ser Ala Gly Val Gln Glu Asp Ala Ala Ser Leu Arg
                2745                2750                2755 gcc ttc acg gag gct atg acc agg tac tcc gcc ccc ccc ggg gac ccc      8660
Ala Phe Thr Glu Ala Met Thr Arg Tyr Ser Ala Pro Pro Gly Asp Pro
            2760                2765                2770 cca caa cca gaa tac gac ttg gag ctt ata aca tca tgc tcc tcc aac      8708
Pro Gln Pro Glu Tyr Asp Leu Glu Leu Ile Thr Ser Cys Ser Ser Asn
        2775                2780                2785 gtg tca gtc gcc cac gac ggc gct gga aag agg gtc tac tac ctt acc      8756
Val Ser Val Ala His Asp Gly Ala Gly Lys Arg Val Tyr Tyr Leu Thr
2790                2795                2800                2805 cgt gac cct aca acc ccc ctc gcg aga gcc gcg tgg gag aca gca aga      8804
Arg Asp Pro Thr Thr Pro Leu Ala Arg Ala Ala Trp Glu Thr Ala Arg
                2810                2815                2820 cac act cca gtc aat tcc tgg cta ggc aac ata atc atg ttt gcc ccc      8852
His Thr Pro Val Asn Ser Trp Leu Gly Asn Ile Ile Met Phe Ala Pro
            2825                2830                2835 aca ctg tgg gcg agg atg ata ctg atg acc cat ttc ttt agc gtc ctc      8900
Thr Leu Trp Ala Arg Met Ile Leu Met Thr His Phe Phe Ser Val Leu
        2840                2845                2850 ata gcc agg gat cag ctt gaa cag gct ctt aac tgt gag atc tac gga      8948
Ile Ala Arg Asp Gln Leu Glu Gln Ala Leu Asn Cys Glu Ile Tyr Gly
    2855                2860                2865 gcc tgc tac tcc ata gaa cca ctg gat cta cct cca atc att caa aga      8996
Ala Cys Tyr Ser Ile Glu Pro Leu Asp Leu Pro Pro Ile Ile Gln Arg
2870                2875                2880                2885 ctc cat ggc ctc agc gca ttt tca ctc cac agt tac tct cca ggt gaa      9044
Leu His Gly Leu Ser Ala Phe Ser Leu His Ser Tyr Ser Pro Gly Glu
                2890                2895                2900 atc aat agg gtg gcc gca tgc ctc aga aaa ctt ggg gtc ccg ccc ttg      9092
Ile Asn Arg Val Ala Ala Cys Leu Arg Lys Leu Gly Val Pro Pro Leu
            2905                2910                2915 cga gct tgg aga cac cgg gcc cgg agc gtc cgc gct agg ctt ctg tcc      9140
Arg Ala Trp Arg His Arg Ala Arg Ser Val Arg Ala Arg Leu Leu Ser
        2920                2925                2930 aga gga ggc agg gct gcc ata tgt ggc aag tac ctc ttc aac tgg gca      9188
Arg Gly Gly Arg Ala Ala Ile Cys Gly Lys Tyr Leu Phe Asn Trp Ala
    2935                2940                2945 gta aga aca aag ctc aaa ctc act cca ata gcg gcc gct ggc cgg ctg      9236
Val Arg Thr Lys Leu Lys Leu Thr Pro Ile Ala Ala Ala Gly Arg Leu
2950                2955                2960                2965 gac ttg tcc ggt tgg ttc acg gct ggc tac agc ggg gga gac att tat      9284
Asp Leu Ser Gly Trp Phe Thr Ala Gly Tyr Ser Gly Gly Asp Ile Tyr
                2970                2975                2980 cac agc gtg tct cat gcc cgg ccc cgc tgg ttc tgg ttt tgc cta ctc      9332
His Ser Val Ser His Ala Arg Pro Arg Trp Phe Trp Phe Cys Leu Leu
            2985                2990                2995 ctg ctc gct gca ggg gta ggc atc tac ctc ctc ccc aac cga tga          9377
Leu Leu Ala Ala Gly Val Gly Ile Tyr Leu Leu Pro Asn Arg
        3000                3005                3010 aggttggggt aaacactccg gcctcttaag ccatttcctg tttttttttt tttttttttt      9437 tttttttct  tttttttttt  ctttccttc  cttcttttt  tcctttcttt  ttcccttctt    9497
```

-continued

```
taatggtggc tccatcttag ccctagtcac ggctagctgt gaaaggtccg tgagccgcat      9557
gactgcagag agtgctgata ctggcctctc tgcagatcat gt                         9599
```

<210> SEQ ID NO 14
<211> LENGTH: 3011
<212> TYPE: PRT
<213> ORGANISM: Hepatitis C virus

<400> SEQUENCE: 14

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
```

-continued

```
                 355                 360                 365
Ala Lys Val Leu Val Leu Leu Leu Phe Ala Gly Val Asp Ala Glu
        370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
        450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
                515                 520                 525

Trp Gly Ala Asn Asp Thr Asp Val Phe Val Leu Asn Asn Thr Arg Pro
        530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
770                 775                 780
```

```
Gly Ala Val Tyr Ala Leu Tyr Gly Met Trp Pro Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
        995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Thr Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Leu Phe Arg Ala Ala Val
    1170                1175                1180

Cys Thr Arg Gly Val Ala Lys Ala Val Asp Phe Ile Pro Val Glu Asn
1185                1190                1195                1200
```

-continued

```
Leu Gly Thr Thr Met Arg Ser Pro Val Phe Thr Asp Asn Ser Ser Pro
            1205                1210                1215
Pro Ala Val Pro Gln Ser Phe Gln Val Ala His Leu His Ala Pro Thr
        1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly Phe
    1250                1255                1260
Gly Ala Tyr Met Ser Lys Ala His Gly Val Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
            1300                1305                1310
Ile Ile Cys Asp Glu Cys His Ser Thr Asp Ala Thr Ser Ile Leu Gly
            1315                1320                1325
Ile Gly Thr Val Leu Asp Gln Ala Glu Thr Ala Gly Ala Arg Leu Val
        1330                1335                1340
Val Leu Ala Thr Ala Thr Pro Pro Gly Ser Val Thr Val Ser His Pro
1345                1350                1355                1360
Asn Ile Glu Glu Val Ala Leu Ser Thr Thr Gly Glu Ile Pro Phe Tyr
                1365                1370                1375
Gly Lys Ala Ile Pro Leu Glu Val Ile Lys Gly Gly Arg His Leu Ile
            1380                1385                1390
Phe Cys His Ser Lys Lys Lys Cys Asp Glu Leu Ala Ala Lys Leu Val
            1395                1400                1405
Ala Leu Gly Ile Asn Ala Val Ala Tyr Tyr Arg Gly Leu Asp Val Ser
        1410                1415                1420
Val Ile Pro Thr Ser Gly Asp Val Val Val Ser Thr Asp Ala Leu
1425                1430                1435                1440
Met Thr Gly Phe Thr Gly Asp Phe Asp Ser Val Ile Asp Cys Asn Thr
                1445                1450                1455
Cys Val Thr Gln Thr Val Asp Phe Ser Leu Asp Pro Thr Phe Thr Ile
            1460                1465                1470
Glu Thr Thr Thr Leu Pro Gln Asp Ala Val Ser Arg Thr Gln Arg Arg
        1475                1480                1485
Gly Arg Thr Gly Arg Gly Lys Pro Gly Ile Tyr Arg Phe Val Ala Pro
    1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Thr
                1525                1530                1535
Val Arg Leu Arg Ala Tyr Met Asn Thr Pro Gly Leu Pro Val Cys Gln
            1540                1545                1550
Asp His Leu Glu Phe Trp Glu Gly Val Phe Thr Gly Leu Thr His Ile
        1555                1560                1565
Asp Ala His Phe Leu Ser Gln Thr Lys Gln Ser Gly Glu Asn Phe Pro
    1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
                1605                1610                1615
Thr Leu His Gly Pro Thr Pro Leu Leu Tyr Arg Leu Gly Ala Val Gln
```

-continued

```
                1620                1625                1630
Asn Glu Val Thr Leu Thr His Pro Ile Thr Lys Tyr Ile Met Thr Cys
        1635                1640                1645
Met Ser Ala Asp Leu Glu Val Val Thr Ser Thr Trp Val Leu Val Gly
    1650                1655                1660
Gly Val Leu Ala Ala Leu Ala Ala Tyr Cys Leu Ser Thr Gly Cys Val
1665                1670                1675                1680
Val Ile Val Gly Arg Ile Val Leu Ser Gly Lys Pro Ala Ile Ile Pro
                1685                1690                1695
Asp Arg Glu Val Leu Tyr Gln Glu Phe Asp Glu Met Glu Glu Cys Ser
            1700                1705                1710
Gln His Leu Pro Tyr Ile Glu Gln Gly Met Met Leu Ala Glu Gln Phe
        1715                1720                1725
Lys Gln Lys Ala Leu Gly Leu Leu Gln Thr Ala Ser Arg His Ala Glu
    1730                1735                1740
Val Ile Thr Pro Ala Val Gln Thr Asn Trp Gln Lys Leu Glu Val Phe
1745                1750                1755                1760
Trp Ala Lys His Met Trp Asn Phe Ile Ser Gly Ile Gln Tyr Leu Ala
                1765                1770                1775
Gly Leu Ser Thr Leu Pro Gly Asn Pro Ala Ile Ala Ser Leu Met Ala
            1780                1785                1790
Phe Thr Ala Ala Val Thr Ser Pro Leu Thr Thr Gly Gln Thr Leu Leu
        1795                1800                1805
Phe Asn Ile Leu Gly Gly Trp Val Ala Gln Leu Ala Ala Pro Gly
    1810                1815                1820
Ala Ala Thr Ala Phe Val Gly Ala Gly Leu Ala Gly Ala Ala Ile Gly
1825                1830                1835                1840
Ser Val Gly Leu Gly Lys Val Leu Val Asp Ile Leu Ala Gly Tyr Gly
                1845                1850                1855
Ala Gly Val Ala Gly Ala Leu Val Ala Phe Lys Ile Met Ser Gly Glu
            1860                1865                1870
Val Pro Ser Thr Glu Asp Leu Val Asn Leu Leu Pro Ala Ile Leu Ser
        1875                1880                1885
Pro Gly Ala Leu Val Val Gly Val Val Cys Ala Ala Ile Leu Arg Arg
    1890                1895                1900
His Val Gly Pro Gly Glu Gly Ala Val Gln Trp Met Asn Arg Leu Ile
1905                1910                1915                1920
Ala Phe Ala Ser Arg Gly Asn His Val Ser Pro Thr His Tyr Val Pro
                1925                1930                1935
Glu Ser Asp Ala Ala Ala Arg Val Thr Ala Ile Leu Ser Ser Leu Thr
            1940                1945                1950
Val Thr Gln Leu Leu Arg Arg Leu His Gln Trp Ile Ser Ser Glu Cys
        1955                1960                1965
Thr Thr Pro Cys Ser Gly Ser Trp Leu Arg Asp Ile Trp Asp Trp Ile
    1970                1975                1980
Cys Glu Val Leu Ser Asp Phe Lys Thr Trp Leu Lys Ala Lys Leu Met
1985                1990                1995                2000
Pro Gln Leu Pro Gly Ile Pro Phe Val Ser Cys Gln Arg Gly Tyr Arg
                2005                2010                2015
Gly Val Trp Arg Gly Asp Gly Ile Met His Thr Arg Cys His Cys Gly
            2020                2025                2030
Ala Glu Ile Thr Gly His Val Lys Asn Gly Thr Met Arg Ile Val Gly
        2035                2040                2045
```

-continued

```
Pro Arg Thr Cys Arg Asn Met Trp Ser Gly Thr Phe Pro Ile Asn Ala
    2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
            2100                2105                2110

Pro Cys Gln Ile Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
            2180                2185                2190

Gly Ser Pro Pro Ser Met Ala Ser Ser Ser Ala Ser Gln Leu Ser Ala
        2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
                2245                2250                2255

Asp Pro Leu Val Ala Glu Glu Asp Glu Arg Glu Val Ser Val Pro Ala
            2260                2265                2270

Glu Ile Leu Arg Lys Ser Arg Arg Phe Ala Arg Ala Leu Pro Val Trp
        2275                2280                2285

Ala Arg Pro Asp Tyr Asn Pro Pro Leu Val Glu Thr Trp Lys Lys Pro
    2290                2295                2300

Asp Tyr Glu Pro Pro Val Val His Gly Cys Pro Leu Pro Pro Pro Arg
2305                2310                2315                2320

Ser Pro Pro Val Pro Pro Pro Arg Lys Lys Arg Thr Val Val Leu Thr
                2325                2330                2335

Glu Ser Thr Leu Ser Thr Ala Leu Ala Glu Leu Ala Thr Lys Ser Phe
            2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Val Glu Ser
    2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Gly Ala Asp Thr Glu Asp
                2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
    2450                2455                2460
```

-continued

```
Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Leu Leu Ser Val Glu Glu Ala Cys Ser Leu Thr
        2500                2505                2510

Pro Pro His Ser Ala Lys Ser Lys Phe Gly Tyr Gly Ala Lys Asp Val
    2515                2520                2525

Arg Cys His Ala Arg Lys Ala Val Ala His Ile Asn Ser Val Trp Lys
2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
            2565                2570                2575

Ala Arg Leu Ile Val Phe Pro Asp Leu Gly Val Arg Val Cys Glu Lys
        2580                2585                2590

Met Ala Leu Tyr Asp Val Val Ser Lys Leu Pro Leu Ala Val Met Gly
    2595                2600                2605

Ser Ser Tyr Gly Phe Gln Tyr Ser Pro Gly Gln Arg Val Glu Phe Leu
2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
        2660                2665                2670

Ile Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly Val
2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
        2740                2745                2750

Ala Ala Ser Leu Arg Ala Phe Thr Glu Ala Met Thr Arg Tyr Ser Ala
    2755                2760                2765

Pro Pro Gly Asp Pro Pro Gln Pro Glu Tyr Asp Leu Glu Leu Ile Thr
2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
        2820                2825                2830

Ile Met Phe Ala Pro Thr Leu Trp Ala Arg Met Ile Leu Met Thr His
    2835                2840                2845

Phe Phe Ser Val Leu Ile Ala Arg Asp Gln Leu Glu Gln Ala Leu Asn
2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
```

```
                      2885                2890                2895
Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
        2980                2985                2990

Trp Phe Cys Leu Leu Leu Ala Ala Gly Val Gly Ile Tyr Leu Leu
        2995                3000                3005

Pro Asn Arg
    3010

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
gaaggaggga ggtttgaagg a                                             21

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
ccagttccgg gcaagaact                                                19
```

CHIMERIC GB VIRUS B (GBV-B)

The present application is a CIP of U.S. patent application Ser. No. 09/587,653 filed on Jun. 5, 2000 and U.S. Provisional Application Ser. No. 60/137,665 filed on Jun. 4, 1999. The entire text of the above-referenced disclosures is herein incorporated by reference.

BACKGROUND OF THE INVENTION

A. Field of the Invention

The present invention relates generally to the fields of biochemistry, molecular biology, and virology. More particularly, it relates to the identification of 259 nucleotides of previously unrecognized sequence located at the 3' end of the GB virus B (GBV-B) genome.

B. Description of Related Art

Chronic hepatitis C is a major threat to the public health. Serologic surveys suggest that as many as 3.9 million Americans are chronically infected with the responsible virus, hepatitis C virus (HCV) (Alter, 1997). These individuals are at increased risk of developing progressive hepatic fibrosis leading to cirrhosis and loss of hepatocellular function, as well as hepatocellular carcinoma. The course of chronic hepatitis C is typically lengthy, often extending over decades, with insidious clinical progression usually occurring in the absence of symptoms. Nonetheless, liver disease due to HCV results in the death of 8,000–10,000 Americans annually, and chronic hepatitis C is the most common cause of liver transplantation within the U.S.

Therefore, HCV is a major public health problem. However, therapy for chronic hepatitis C is problematic. Recombinant interferon-α is approved for treatment of chronic hepatitis C (Consensus Development Panel, 1997). The benefit of interferon-α results primarily from its antiviral properties and its ability to inhibit production of virus by infected hepatocytes (Neumann et al., 1998). Nonetheless, even under optimal therapeutic regimen, the majority of patients with chronic, hepatitis C fail to eliminate the virus or resolve their liver disease. Treatment failures are especially common in persons infected with genotype 1 HCV, unfortunately the most prevalent genotype in the U.S. Thus, there is an urgent need to better understand the virus and develop better treatment. Unfortunately, technical difficulties in working with HCV have made it necessary to use infectious surrogate viruses in efforts to develop treatments and vaccines for HCV.

Scientists' efforts to better understand HCV and to develop new drugs for treatment of hepatitis C have been stymied by two overwhelming technical deficiencies: first, the nonexistence of a high permissive cell line that supports replication of the virus and second, the absence of a permissive animal species other than chimpanzees, which are endangered and therefore available on a limited basis.

Presently, those who are working on HCV treatment and prevention are employing an infectious chimeric virus of sindbis and HCV and/or an infectious clone of pestiviruses as surrogate virus models in HCV drug discovery efforts, due to the above technical difficulties of working with HCV. Alternatively, they are using isolated proteins or RNA segments of HCV for biochemical and structural studies. This approach precludes functional studies of virus replication and its inhibition.

GBV-B is a hepatotropic flavivirus that has a unique phylogenetic relationship to human HCV and strong potential to serve as a surrogate virus in drug discovery efforts related to hepatitis C antiviral drug development. GBV-B causes acute hepatitis in experimentally infected tamarins (Simons et al., 1995; Schlauder et al., 1995; Karayiannis et al., 1989) and can serve as a surrogate virus for HCV in drug discovery efforts (due to technical difficulties in working with HCV). GBV-B virus is much closer in sequence and biological properties than the above-described models. It will be easier to make biologically relevant chimeras between HCV and GBV-B than by using more distantly related viruses. GBV-B is hepatotropic (as is HCV), whereas the viruses used in these competing technologies are not. In view of the above, an infectious clone of GBV-B would be useful to those working on HCV treatment and prevention.

Unfortunately, the use of GBV-B as a surrogate or model for HCV has not been possible in the past, because no infectious molecular clone of GBV-B virus genome could be prepared. It is now known that this obstacle was encountered because the GBV-B genome was believed to be 259 nucleotides shorter than its actual length (Muerhoff et al., 1995; Simons et al., 1995). Others, previous to the inventors, had failed to realize that the 3' sequence of GBV-B was missing from the prior sequences. Without this 3' sequence, it is not possible to prepare an infectious GBV-B molecular clone.

SUMMARY OF THE INVENTION

As discussed above, an infectious molecular clone of GBV-B would be very useful for the development of HCV preventative and therapeutic treatments. The construction of an infectious molecular clone of this virus will require the newly determined 3' sequence to be included in order for the clone to be viable. The inventors have elucidated the previously unrecognized 3' terminal sequence of GBV-B (SEQ ID NO:1). This sequence has been reproducibly recovered from tamarin serum containing GBV-B RNA, in RT-PCR protocols using several different primer sets, and as a fusion with previously reported 5' GBV-B sequences.

The newly identified 3' sequence is not included in published reports of the GBV-B sequence, nor described in patents relating to the original identification of the viral sequence (see U.S. Pat. No. 5,807,670 and references therein).

The invention has utility in that the inclusion of the sequence will be necessary for construction of an infectious molecular GBV-B clone. Such clones clearly have the potential to be constructed as chimeras including relevant hepatitis C virus sequences in lieu of the homologous GBV-B sequence, providing unique tools for drug discovery efforts. A full-length molecular clone of GBV-was constructed, as described in later sections of this specification.

GBV-B can be used as a model for HCV, and the GBV-B genome can be used as the acceptor molecule in the construction of chimeric viral RNAs containing sequences of both HCV and GBV-B. Such studies will allow one to investigate the mechanisms for the different biological properties of these viruses and to discover and investigate potential inhibitors of specific HCV activities (e.g., proteinase) required for HCV replication. However, all this work is dependent upon construction of an infectious clone of GBV-B, which is itself dependent on the incorporation of the correct 3' terminal nucleotide sequence within this clone. GBV-B has unique advantages over HCV in terms of its ability to replicate and cause liver disease in tamarins, which present fewer restrictions to research than chimpanzees, the only nonhuman primate species known to be permissive for HCV.

An infectious molecular clone of GBV-B is expected to have utility in liver-specific gene expression or in gene therapy. This application might be enhanced by the inclusion of HCV genomic sequence in the form of a GBV-B/HCV chimera. Further, an infectious GBV-B/HCV chimera expressing HCV envelope proteins can have utility as a vaccine immunogen for hepatitis C.

A full-length cDNA copy of the GBV-B genome was constructed to contain the newly identified 3' terminal sequences. RNA transcribed from this cDNA copy of the genome would be infectious when inoculated into the liver of a GBV-B permissive tamarin, giving rise to rescued GBV-B virus particles. A chimeric molecule would then be constructed from this infectious GBV-B clone in which the HCV NS3 proteinase or proteinase/helicase sequence (or other relevant HCV sequences of interest in drug discovery efforts) would be placed in frame in lieu of the homologous GBV-B sequence, and this chimeric cDNA would be used to generate infectious GBV-B/HCV chimeric viruses by intrahepatic inoculation of synthetic RNA in tamarins. Published studies indicate that the GBV-B and HCV proteinases have closely related substrate recognition and cleavage properties, making such chimeras highly likely to be viable. These newly generated chimeric GBV-B/HCV viruses could be used in preclinical testing of candidate HCV NS3 proteinase inhibitors.

Therefore, the present invention encompasses an isolated polynucleotide encoding a 3' sequence of the GBV-B genome. The polynucleotide may include the sequence identified as SEQ ID NO:1. It is contemplated that the polynucleotide may be a DNA molecule or it can be an RNA molecule. It is further contemplated that expression constructs may contain a polynucleotide that has a stretch of contiguous nucleotides from SEQ ID NO:1 and/or SEQ ID NO:2, for example, lengths of 50, 100, 150, 250, 500, 1000, 5000, as well as the entire length of SEQ ID NO:1 or 2, are considered appropriate. Such polynucleotides may also be contained in other constructs of the invention or be used in the methods of the invention. Polynucleotides employing sequences from SEQ ID NO:1 may alternatively contain sequences from SEQ ID NO:2 in the constructs and methods of the present invention.

The invention is also understood as covering a viral expression construct that includes a polynucleotide encoding a 3' sequence of the GBV-B genome. This expression construct is further understood to contain the sequence identified as SEQ ID NO:1. The present invention contemplates the expression construct as a plasmid or as a virus. Furthermore, the expression construct can express GBV-B sequences; alternatively it may express sequences from a chimeric GBV-B/HCV virus.

The identification and isolation of a 3' sequence of GBV-B additionally provides a method of producing a virus, particularly a full-length virus, by introducing into a host cell a viral expression construct containing a polynucleotide encoding a 3' sequence of GBV-B and by culturing the host cell under conditions permitting production of a virus from the construct. This method can be practiced using a prokaryotic cell as a host cell, or by using a eukaryotic cell as a host cell. Furthermore, the eukaryotic cell can be located within an animal.

A method of producing virus according to the claimed invention can also be employed using a polynucleotide that contains synthetic RNA and/or synthetic DNA. Moreover, a step can be added to the method by also isolating any virus produced from the host cell. The virus can then be purified to homogeneity.

In further embodiments, the present invention encompasses an oligonucleotide between about 10 and about 259 consecutive bases of SEQ ID NO:1. This oligonucleotide is contemplated to be about 15 bases in length, about 20 bases in length, about 25 bases in length, about 30 bases in length, about 35 bases in length, about 50 bases in length, about 100 bases in length, about 150 bases in length, about 200 bases in length, or about 259 bases in length.

Additional examples of the claimed invention include a method for identifying a compound active against a viral infection by providing a virus expressed from a viral construct containing a 3' sequence of a GBV-B virus, by contacting the virus with a candidate substance; and by comparing the infectious ability of the virus in the presence of the candidate substance with the infectious ability of the virus in a similar system in the absence of the candidate substance. It is contemplated that the invention can be practiced using GBV-B virus or a GBV-B/HCV chimera.

The present invention can also be understood to provide a compound active against a viral infection identified by providing a virus expressed from a viral construct containing a 3' sequence of a GBV-B virus; contacting the virus with a candidate substance; and comparing the infectious ability of the virus in the presence of the candidate substance with the infectious ability of the virus in a similar system in the absence of the candidate substance. In some embodiments an active compound is identified using a GBV-B virus, while in other embodiments an active compound is identified using a GBV-B/HCV chimera.

In various embodiments of the invention, a GBV-B polynucleotide may encode a GBV-B/HCV chimera that includes at least part of a 5' NTR sequence derived from a HCV 5' NTR. The 5' NTR may comprise at least one domain derived from the 5' NTR of HCV. In certain embodiments, the GVB-B/HCV chimera may include at least domain III of the 5' NTR derived from the 5' NTR of HCV. In yet other embodiments the infectious GBV-B clone may comprise domain III of the 5' NTR of HCV, which may or may not include one or more structural or non-structural genes of HCV also incorporated into the chimeric virus. The portions of the 5' NTR of the GVB-B/HCV chimeras will generally be replaced by analogous sequences from the 5' NTR of HCV. It will be understood that the portions or parts of the 5' NTR of GBV-B that may be replaced include all or part of domain I (including sub-region Ia and Ib of GBV-B), domain II, domain III, domain IV, or any combination thereof. Any combination of 5' NTR domains of GBV-B may be replaced with an analogous region of HCV. In certain embodiments, the replacement of a GBV-B region may be accompanied by the deletion of the 5' NTR GBV-B domain Ib region. In addition, any one, two, or three of the 5' NTR domains of GBV-B may be replaced in any combination with analogous sequences from HCV.

In further embodiments of the invention, a polynucleotide encoding a GBV-B/HCV chimera including a 5' NTR domain III sequence derived from a HCV 5' NTR may be propagated in vivo, in particular, in the liver of an appropriate host.

Various other embodiments may include isolated polynucleotides comprising a chimeric GBV-B genome, wherein at least part, but not all of a 5' NTR sequence is derived from a HCV 5' NTR. The polynucleotides may be synthetic RNA, RNA, DNA or the like.

Some embodiments include one or more virus, one or more hepatotropic virus, and/or one or more viral expression constructs comprising a chimeric GBV-B polynucleotides including at least a part of the 5' NTR sequence is derived from a HCV 5' NTR.

Methods of producing a chimeric GBV-B virus encoding at least part of a 5' NTR sequence derived from a HCV 5' NTR sequence comprising introducing into a host cell a viral expression construct comprising a chimeric GBV-B polynucleotide encoding at least part of a 5' NTR sequence derived from a HCV 5' NTR sequence and culturing said host cell under conditions permitting production of a virus from said construct are contemplated. The method may use a host cell that is a eukaryotic cell and the host cell a may in an animal. The method may further include the step of isolating virus from said host cell and in particular purify the virus to homogeneity.

In addition, methods for identifying a compound active against a viral infection comprising are contemplated. The methods may include providing a virus expressed from a viral construct comprising at least part of a 5' NTR derived from a HCV 5' NTR, as described herein; contacting said virus with a candidate substance; and comparing the infectious ability of the virus in the presence of said candidate substance with the infectious ability of the virus in a similar system in the absence of said candidate substance. Each of the embodiments may use or include any of the 5' NTR chimeras described herein.

Other embodiments of the invention may include a compound active against a viral infection identified according to the method described above.

As used herein the specification, "a" or "an" may mean one or more. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3B, top panel, shows the SDS-PAGE gel on which the products of translation were separated. FIG. 3B, bottom panel, are the results of the PhosphorImager analysis. Mock=no RNA transcript in the translation mix; and m=size markers.

FIG. 7. Shows the sequence differences between chimeric viral RNAs recovered from animals T16444 and T16451, and the parental synthetic III$^{HC}$ RNA.

DESCRIPTION OF ILLUSTRATIVE EMBODIMENTS

A. GVB-B Virus

Figure 1:
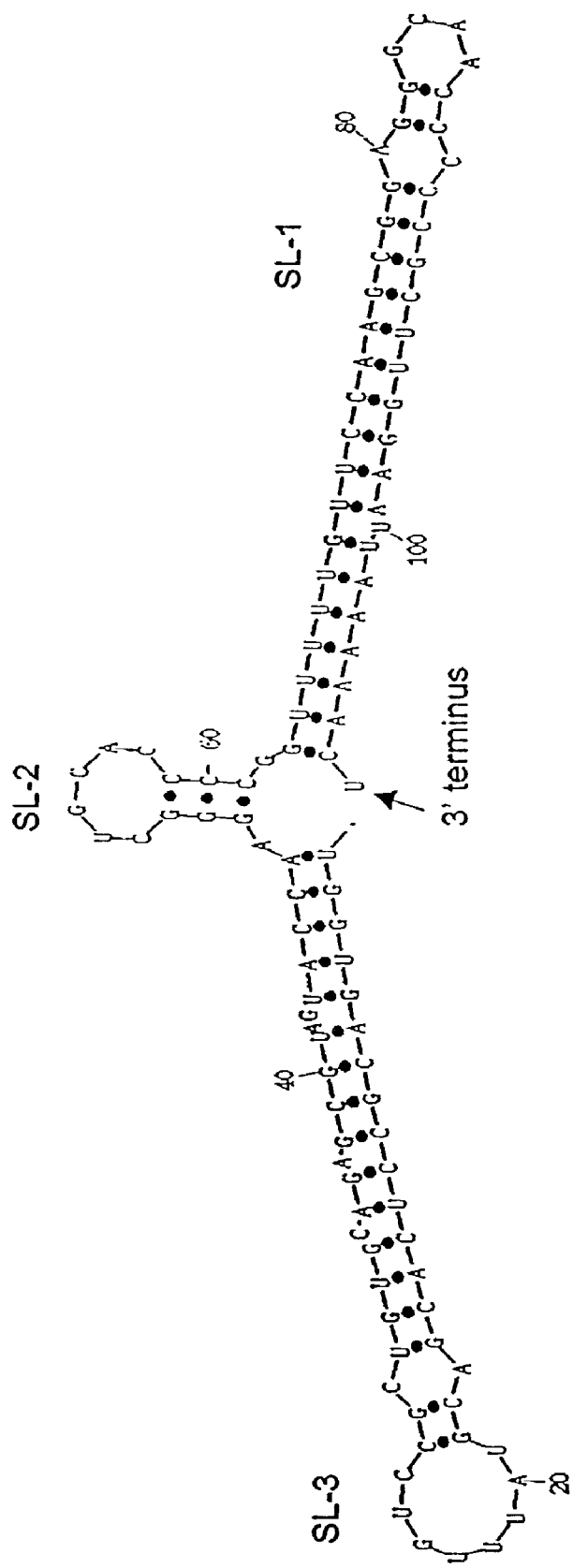
FIG. 1. Predicted secondary RNA structure at the 3' end of the novel 3' GBV-B sequence. The structure shown is that predicted for the 3' terminal 108 nucleotides of the GBV-B genomic RNA by the MFOLD 3.0 computer program of Zucker and Turner, and has an initial free energy of −48 kcal/mole. The predicted structure contains 3 stem-loops, numbered from the 3' end of the genome and labeled SL-1, SL-2, and SL-3. The structure of SL-1 is highly probable, given its terminal position within the genome. Alternative foldings of SL-2 and SL-3 are possible.

The GBV-B genome structure is very similar to hepatitis C and these viruses share approximately 25% nucleotide identity (Simons et al., 1995; Muerhoff et al., 1995). As indicated above, this makes GBV-B more closely related to HCV than any other known virus. GBV-B genomic RNA is about 9.5 kb in length (Muerhoff et al., 1995) with a structured 5' noncoding region that contains an IRES that shares many structural features with the HCV IRES (Honda et al., 1996; Rijnbrand et al., 1999). As in HCV, this IRES drives the cap-independent translation of a long open reading frame. The polyprotein expressed from this reading frame appears to be organized identically to that of HCV, and processed to generate proteins with functions similar to those of HCV (Muerhoff et al., 1995). In fact, the major serine proteinases of these viruses (NS3) have been shown to have similar cleavage specificities (Scarselli et al., 1997). Finally, like HCV and distinct from the pestiviruses, the genomic RNA of GBV-B has a poly(U) tract located near its 3' terminus (Simons et al., 1995; Muerhoff et al., 1995). In addition, unreported sequences located at the extreme 3' end of the genome have been identified. This work indicates that the GBV-B RNA, like that of HCV (HCV (Tanaka et al; 1995; Kolykhalov et al., 1996), terminates in a lengthy run of heterogeneous bases (310 nts in GBV-B) possessing a readily apparent secondary structure B. Nucleic Acids The present invention provides a nucleic acid sequence encoding a 3' sequence of the GBV-B genome (SEQ ID NO:1).

It should be clear that the present invention is not limited to the specific nucleic acids disclosed herein. As discussed below, a "3' sequence of the GBV-B genome" may contain a variety of different bases and yet still be functionally indistinguishable from the sequences disclosed herein. Such functionally indistinguishable sequences are likely to maintain the basic structure depicted in FIGS. 1 and 2, which may be used to guide the prediction of viable nucleotide substitutions.

1. Polynucleotides Encoding the 3' Sequence of the GBV-V Genome

A 3' sequence of the GBV-B genome disclosed in SEQ ID NO:1 is one aspect of the present invention. Nucleic acids according to the present invention may encode the 3' sequence of the GBV-B genome set forth in SEQ ID NO:1, the entire GBV-B genome, or any other fragment of a 3' sequence of the GBV-B genome set forth herein. The nucleic acid may be derived from genomic RNA as cDNA, i.e., cloned directly from the genome of GBV-B. cDNA may also be assembled from synthetic oligonucleotide segments.

It also is contemplated that a 3' sequence of the GBV-B genome may be represented by natural variants that have slightly different nucleic acid sequences but, nonetheless, maintain the same general structure (see FIGS. 1 and 2) and perform the same function in RNA replication.

As used in this application, the term "a nucleic acid encoding a 3' sequence of the GBV-B genome" refers to a nucleic acid molecule that may be isolated free of total viral nucleic acid. In preferred embodiments, the invention concerns nucleic acid sequences essentially as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. The term "as set forth in SEQ ID NO:1" means that the nucleic acid sequence substantially corresponds to a portion of SEQ ID NO:1. It is contemplated that the techniques and methods described in this disclosure may apply to any of the sequences contained herein, including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 will be sequences that are "as set forth in SEQ ID NO:1." Sequences that are essentially the same as those set forth in SEQ ID NO:1 may also be functionally defined as sequences that are capable of hybridizing to a nucleic acid segment containing the complement of SEQ ID NO:1 under standard conditions.

The nucleic acid segments and polynucleotides of the present invention include those encoding biologically functional equivalent 3' sequences of the GBV-B genome. Changes designed by man may be introduced through the application of site-directed mutagenesis techniques or may be introduced randomly and screened later for the desired function, as described below.

3' sequence of the GBV-B genome sequences also are provided. Each of the foregoing is included within all aspects of the following description. The present invention concerns cDNA segments reverse transcribed from GBV-B genomic RNA (referred to as "DNA"). As used herein, the term "polynucleotide" refers to an RNA or DNA molecule that may be isolated free of other RNA or DNA of a particular species.

"Isolated substantially away from other coding sequences" means that the 3' sequence of the GBV-B genome forms the significant part of the RNA or DNA segment and that the segment does not contain large portions of naturally-occurring coding RNA or DNA, such as large fragments or other functional genes or cDNA noncoding regions. Of course, this refers to the polynucleotide as originally isolated, and does not exclude genes or coding regions later added to the it by the hand of man.

In certain other embodiments, the invention concerns isolated DNA segments (cDNA segments reverse transcribed from GVB-B genomic RNA) and recombinant vectors that include within their sequence a nucleic acid sequence essentially as set forth in SEQ ID NO:1. The term "essentially as set forth in SEQ ID NO:1" is used in the same sense as described above.

It also will be understood that nucleic acid sequences may include additional residues, such as additional 5' or 3' sequences, and still be essentially as set forth in one of the sequences disclosed herein, so long as the sequence meets the criteria set forth above, including the maintenance of biological activity. The addition of terminal sequences particularly applies to nucleic acid sequences that may, for example, include additional various non-coding sequences flanking either of the 5' or 3' portions of the coding region, which are known to occur within viral genomes.

Sequences that are essentially the same as those set forth in SEQ ID NO:1 also may be functionally defined as sequences that are capable of hybridizing to a nucleic acid segment containing the complement of SEQ ID NO:1 under relatively stringent conditions. Suitable relatively stringent hybridization conditions will be well known to those of skill in the art.

The nucleic acid segments of the present invention, regardless of the length of the coding sequence itself, may be combined with other RNA or DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a short contiguous stretch identical to or complementary to SEQ ID NO:1, such as about 15–24 or about 25–34 nucleotides and that are up to about 259 nucleotides being preferred in certain cases. Other stretches of contiguous sequence that may be identical or complementary to any of the sequences disclosed herein, including the SEQ ID NOS. include the following ranges of nucleotides: 50–9,399, 100–9,000, 150–8,000, 200–7,000, 250–6,000, 300–5,000, 350–4,000, 400–3,000, 450–2,000, 500–1000. RNA and DNA segments with total lengths of about 1,000, about 500, about 200, about 100 and about 50 base pairs in length (including all intermediate lengths) are also contemplated to be useful.

In a non-limiting example, one or more nucleic acid constructs may be prepared that include a contiguous stretch of nucleotides identical to or complementary to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. Such a stretch of nucleotides, or a nucleic acid construct, may be about, or at least about, 3, about 4, about 5, about 6, about 7, about 8,, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39 about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 618, about 650, about 700, about 750, about 1,000, about 2,000, about 3,000, about 4,000, about 5,000, about 6,000, about 7,000, about 8,000, about 9,000, about 9,100, about 9,200, about 9,300, about 9,399, about 9,400, about 9,500, about 9,600, about 9,700, about 9,800, about 9,900, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art.

It will be readily understood that "intermediate lengths," in these contexts means any length between the quoted ranges, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, etc.; 100, 101, 102, 103, etc.; 150, 151, 152, 153, etc.; including all integers through the 200–500; 500–1,000; 1,000–2,000; ranges, up to and including sequences of about 1,001, 1,250, 1,500, and the like.

The various probes and primers designed around the disclosed nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 20-mer, the probes correspond to bases 1 to 20, 2 to 21, 3 to 22 . . . and so on. For a 30-mer, the probes correspond to bases 1 to 30, 2 to 31, 3 to 32 . . . and so on. For a 35-mer, the probes correspond to bases 1 to 35, 2 to 36, 3 to 37 . . . and so on.

2. Oligonucleotide Probes and Primers

Naturally, the present invention also encompasses RNA and DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO. 1 under relatively stringent conditions such as those described herein. Such sequences may encode the entire 3' sequence of the GBV-B genome or functional or non-functional fragments thereof Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225 or more base pairs will be used, although others are contemplated. Longer polynucleotides encoding 250, 500, 1000, 1212, 1500, 2000, 2500, 3000 or 3431 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated and thus will generally be a method of choice depending on the desired results.

In other embodiments, hybridization may be achieved under conditions of, for example, 50 mM Tris-HCl (pH 8.3), 75 mM KCl, 3 nM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

One method of using probes and primers of the present invention is in the search for other viral sequences related to GBV-B or, more particularly, homologs of the GBV-B sequence. By varying the stringency of hybridization, and the region of the probe, different degrees of homology may be discovered.

Another way of exploiting probes and primers of the present invention is in site-directed, or site-specific, mutagenesis. The technique provides a ready ability to prepare and test sequence variants, incorporating one or more of the foregoing considerations, by introducing one or more nucleotide sequence changes into complementary DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement. There are newer and simpler site-directed mutagenesis techniques that can also be employed for this purpose. These include procedures marketed in kit form that are readily available to one of ordinary skill in the art.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

3. Antisense Constructs

In certain embodiments of the invention, the use of antisense constructs of the 3' sequence of the GBV-B genome is contemplated.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs could be used to block early steps in the replication of GBV-B and related viruses, by annealing to 3' terminal sequences and blocking their role in negative-strand initiation.

As stated above, "complementary" or "antisense" means polynucleotide sequences that are substantially complementary over their entire length and have very few base mismatches. For example, sequences of 15 bases in length may be termed complementary when they have complementary nucleotides at 13 or 14 positions. Naturally, sequences which are completely complementary will be sequences which are entirely complementary throughout their entire length and have no base mismatches. Other sequences with lower degrees of homology also are contemplated. For example, an antisense construct which has limited regions of high homology but also contains a non-homologous region (e.g., ribozyme; see below) could be designed. These molecules, though having less than 50% homology, would bind to target sequences under appropriate conditions.

4. Amplification and PCR™

The present invention utilizes amplification techniques in a number of its embodiments. Nucleic acids used as a template for amplification are isolated from cells contained in the biological sample, according to standard methodologies (Sambrook et al., 1989). The nucleic acid may be genomic DNA or RNA or fractionated or whole cell RNA. Where RNA is used, it may be desired to convert the RNA to a complementary DNA using reverse transcriptase (RT). In one embodiment, the RNA is genomic RNA and is used directly as the template for amplification. In others, genomic RNA is first converted to a complementary DNA sequence (cDNA) and this product is amplified according to protocols described below.

Pairs of primers that selectively hybridize to nucleic acids corresponding to GBV-B sequences are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals.

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two or more primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989.

Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. U.S. Pat. No. 4,883,750 describes a method similar to LCR for binding probe pairs to a target sequence.

Qbeta Replicase, described in PCT Application No. PCT/US87/00880, incorporated herein by reference, also may be used as still another amplification method in the present invention.

An isothermal amplification method, in which restriction endonucleases and ligases are used to achieve the amplification of target molecules that contain nucleotide 5'-[alpha-thio]-triphosphates in one strand of a restriction site also may be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences also can be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter/primer sequence to a target ssDNA followed by transcription of many RNA copies of the sequence. This scheme is not cyclic, i.e., new templates are not produced from the resultant RNA transcripts. Other amplification methods include "RACE" and "one-sided PCR" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, also may be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography that may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose or nylon, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5. Expression Constructs

In some embodiments of the present invention, an expression construct that encodes a 3' sequence of GBV-B is utilized. The term "expression construct" is meant to include any type of genetic construct containing a nucleic acid coding for a gene product in which part or all of the nucleic acid encoding sequence is capable of being transcribed. The transcript may be translated into a protein, but it need not be. Expression includes both transcription of a gene and translation of mRNA into a gene product. Expression may also include only transcription of the nucleic acid encoding a gene of interest.

In some constructs, the nucleic acid encoding a gene product is under transcriptional control of promoter and/or enhancer. The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies have shown that promoters are composed of discrete functional modules, each consisting of approximately 7–20 bp of nucleic acids, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of nucleic acids with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

6. Host Cells and Permissive Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of the present invention, "host cell" refers to a prokaryotic or eukaryotic cell, and it includes any transformable organisms that is capable of replicating a vector or virus and/or expressing viral proteins. A host cell can, and has been, used as a recipient for vectors, including viral vectors. A host cell may be "transfected" or "transformed," which refers to a process by which exogenous nucleic acid is transferred or introduced into the host cell. A transformed cell includes the primary subject cell and its progeny. A "permissive cell" refers to a cell that supports the replication of a given virus and consequently undergoes cell lysis. In the context of the present invention, such a virus would include HCV, GBV-B, or other hepatitis viruses. In a "nonpermissive cell," productive infection does not result, but the cell may become stably transformed. In some embodiments, methods employ permissive cells that are a cell line derived from liver cells (liver cell line).

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5.alpha., JM109, and KC8, as well as a number of commercially available bacterial hosts such as SURE.RTM. Competent Cells and SOLOPACK™ Gold Cells (STRATAGENE.RTM., La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector or virus or virus particle may be used in conjunction with either a eukaryotic or prokaryotic host cell, particularly one that is permissive for replication or expression of the vector. It is contemplated that the present invention includes vectors composed of viral sequences, viruses, and viral particles in the methods of the present invention, and that they may be used interchangeably in these methods, depending on their utility.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

7. Pharmaceutical Compositions

The present invention encompasses the use of a 3' sequence of GBV-B in the production of or use as a vaccine to combat HCV infection. Compositions of the present invention comprise an effective amount of GBV-B clone as a therapeutic dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains GVB-B nucleic acid sequences as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A GBV-B clone of the present invention can be formulated into a composition in a neutral or salt form. Pharmaceutically acceptable salts include the acid addition salts (formed with the free amino groups of the protein) and are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like also can be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

C. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Elucidation of a 3' Sequence of the GBV-B Genome

The inventors elucidated the previously unrecognized 3' terminal sequence of GBV-B (SEQ ID NO 1). This sequence was reproducibly recovered from tamarin serum containing GBV-B RNA, in RT-PCR nucleic acid amplification procedures using several different primer sets, and as a fusion with previously reported 5' GBV-B sequences.

There is information in the published literature reporting the putative sequences of the 5' and 3' termini of the GBV-B genome. The nucleic acid sequences of these termini were reportedly determined by ligating the ends of the viral RNA together, amplifying the sequence in the region of the resulting junction by reverse-transcription polymerase chain reaction (RT-PCR), and sequencing of the cDNA amplification product across the junction. However, the inventors believed these results required confirmation. Of particular concern was the fact that the 3' terminus appeared to be shorter than the equivalent region of other viruses in the family Flaviviridae (especially within the genus *Hepacivirus*) and that the reported 3' sequence lacked a defined RNA hairpin structure such as those present in these related viruses. Additional novel sequences at the 3' end of the GBV-B genome were investigated using a serum sample collected from a tamarin that was experimentally infected with virus. Amplification was used to determine the sequence of the 3' end.

First, serum (50 µL) known to contain GBV-B RNA by RT-PCR assay was extracted with Trizol, and the RNA was washed and dried. A synthetic oligonucleotide was then ligated to the 3' end of the viral RNA. The oligonucleotide, AATTCGGCCCTGCAGGCCACAACAGTC, which was phosphorylated at the 5' end and chemically blocked at the 3' end, was ligated to the RNA essentially using the method described by Kolykhalov et al. (Behrens et al., 1996). The RNA was initially dissolved in DMSO and the following additions were made: Tris-Cl, pH 7.5 (10 mM), $MgCl_2$ (10 mM), DTT (5 mM), hexamine cobalt chloride (1 mM), 10 pmol oligo and 8 U T4 ligase. The final concentration of DMSO was 30% in a final volume of 10 µL. The ligation reaction was incubated for 4 or 20 hours at 19° C. 1 µL of the ligation reaction was used directly to make cDNA, using a primer complementary to the ligated oligonucleotide and the Superscript 2 system, in a final volume of 15 µL. 1 µL of cDNA was amplified using the Advantage cDNA system (Clontech) and two additional oligonucleotide primers. These primers included one that was complementary to the ligated oligonucleotide (i.e., "negative sense") and a positive-sense primer located near the 3' end of the reported GBV-B sequence. A product approximately 290 bases in length was obtained, and this was gel purified and directly sequenced. Sequencing was done in both directions using the oligonucleotide primers employed for the amplification; 259 bases that had not been previously reported were identified as fused to the sequence that had been previously described as the 3' terminus of the viral genome.

Figure 2:
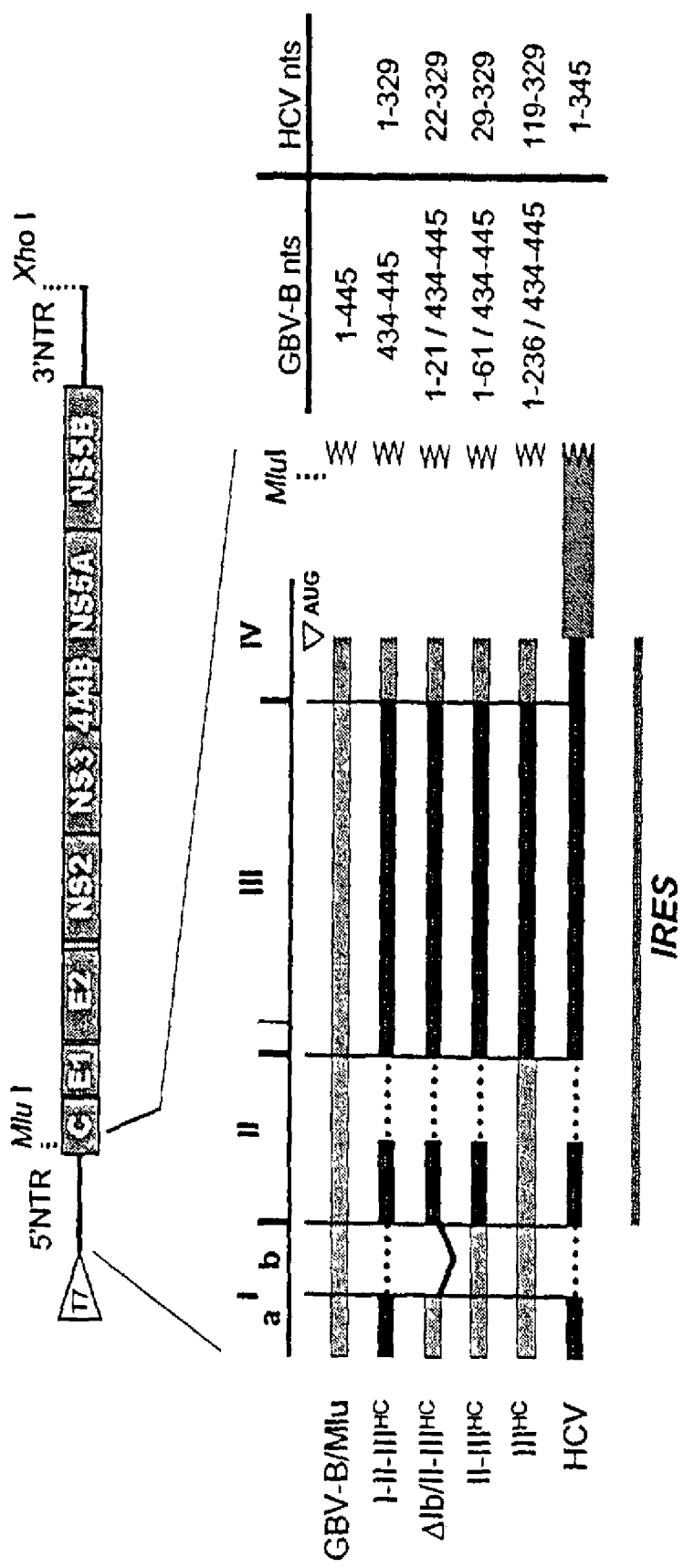
FIG. 2. Illustration of the organization of exemplary chimeric cDNAs containing HCV 5' nontranslated (5' NTR) RNA sequences within the background of a modified (MluI restriction-site containing) GBV-B genetic background.

To ensure that this novel 3' sequence from viral RNA could be reproducibly amplified, an additional 10 µL of infected tamarin serum was extracted using Trizol. cDNA was prepared by reverse transcription using an oligonucleotide primer complementary to the penultimate 3' 25 bases of the novel sequence. Amplification was then done by PCR using the primer previously utilized for cDNA synthesis and a positive-sense primer mapping within the previously published GBV-B sequence. In the initial studies, although a product was readily detected, DNA sequencing showed that this product was missing all of the sequence distal to the poly-U tract. Carrying out the cDNA synthesis in the presence of DMSO circumvented this problem. A cDNA product of approximately 290 bases was obtained. This was sequenced and shown to consist of the 5' primer, 20 bases of the published GBV-B sequence, and 259 bases of the novel sequence obtained in the preceding studies and containing the sequence of the 3' primer. The sequence of the 3' end of GBV-B is shown in SEQ ID NO:1 (FIG. 1). The possible secondary RNA structure for this region is shown in FIG. 2, as predicted by a computer-based RNA folding program. The presence of a predicted hairpin structure at the extreme 3' end of this novel sequence is consistent with its location at the 3' terminus of the viral RNA.

The GBV-B cDNA (synthesis described above) was used as a template for PCR amplification of the 3' 1553 nucleotides (nts) of the GBV-B genome. This PCR amplification product was gel purified and cloned into plasmid DNA using the "Perfectly Blunt Cloning Kit" (Novagene).

Example 2

Construction of an Infectious GBV-B Clone

The elucidation of a 3' sequence of the GBV-B genome will allow those of skill in the art to construct and validate an infectious molecular clone of GBV-B. This will be done using the following procedures.

A full-length cDNA copy of the GBV-B genome containing the newly identified 3' terminal sequences was constructed. RNA transcribed from this cDNA copy of the genome will be infectious when inoculated into the liver of a GBV-B permissive tamarin, giving rise to rescued GBV-B virus particles.

A 1:1000 dilution of GBV-B infectious tamarin serum was obtained. This material was used as a source of viral RNA for the amplification of GBV-B nucleic acid sequences by reverse-transcription polymerase chain reaction. For amplification of previously reported segments of the GBV-B genome, 250 µL of the diluted serum was extracted with Trizol using the manufacturer's instructions. The final RNA pellet was dissolved in 10 µL of a 100 mM DTT buffer containing 5% RNasin. This material was converted into cDNA using Superscript 2 reverse transcriptase and oligonucleotide primers designed to be complementary to the reported GBV-B RNA sequence and to contain unique restriction sites. This cDNA was amplified using the Advantage cDNA kit (Clontech) employing the cDNA primer (negative sensiv as the downstream primer and a similar positive-sense upstream primer, again containing a unique restriction site. The published sequence of GBV-B allowed for the selection of primers in convenient areas of the genome containing unique restriction sites. Using this general strategy, the inventors amplified segments of the reported GBV-B genome representing: (1) nucleotides (nts) 1–1988, using an upstream primer containing a T7 RNA polymerase promoter and a BamH1 site upstream of nt 1, and a downstream primer containing a unique EcoIR1 site (nt 1978); (2) nts 1968–5337, using a downstream primer containing a unique Cla1 site at position 5o27; (3) nts 5317–7837, using a downstream primer containing a Sal1 site at nt 7847; and, (4) nts 7837–9143, using a downstream primer containing an added Xho1 site. It was found necessary to use different PCR conditions for each primer set.

The RT-PCR products generated in these reactions were cloned into plasmid DNA after gel purification, using the "Perfectly Blunt Cloning Kit" (Novagene). Ten bacterial colonies from each of the four RT-PCR products were analyzed for insert size by restriction endonuclease digestion using EcoR1, the sites for this enzyme being located on either side of the insert in the resulting plasmids. For three of the RT-PCR amplicons, 9 of 10 colonies contained plasmids with the correct size insert. The EcoR1-Cla1 amplicon generated only 1/10 colonies with a correct size insert. Thus, 30 additional colonies were examined, yielding two more clones with insert of the correct size. For each of these plasmids, simple restriction patterns were obtained using two restriction enzymes. As these appeared to be correct, the plasmid DNAs were subjected to sequencing using an ABI automatic sequencer.

Example 3

Nucleotide Sequence of the Cloned GBV-B cDNA

The 5' region of the cloned sequence revealed a relatively long nontranslated region corresponding to the published sequence of the GBV-B 5' NTR, which includes an IRES. This region was followed by a long open reading frame. Near the 3' end of the genome a poly-U tract was identified; however, this was shorter than the published 3' homopolymeric poly-U region. The sequence from these clones was compared with those in the GenBank database (Accession U22304, "Hepatitis GB virus B polypeptide complete genome"). Twenty-two nucleotide differences were identified, of which 14 gave rise to amino acid changes (Table 1). In order to determine whether these changes were genuine or RT-PCR artifacts, which could have been introduced due to the very small amount of material from which these sequences were amplified, segments of the genome containing these changes were reamplified using a serum sample from an independently infected tamarin. Of the 14 changes noted in the original cDNA clones, 12 were not present in these newly amplified sequences and thus were probably RT-PCR artifacts (Table 2.). A particularly interesting difference from the published GenBank sequence, however, which was present in both the original clones as well as a repeat amplification, was a two-nucleotide substitution that obliterated the Sal1 site present in the published sequence.

TABLE 1

Differences in the amino acid sequences of GBV-B cDNA clones and the GBV-B sequence reported by Simons et al. (1995).

| GBV-B Protein | AMINO ACID Δ FROM ABBOTT SEQUENCE | RT-PCR Products from Tamarin 12024 (PCR Reaction #) |
|---|---|---|
| Core | $G_{99} \rightarrow S$ | G (38.1a) |
| E1 | $V_{395} \rightarrow I$ | V (40.2a) |
| E2 | $D_{703} \rightarrow N$ | D (42.3a) |
| E2 | $P_{706} \rightarrow Q$ | H (42.3a) |
| E2 | $A_{728} \rightarrow V$ | A (42.3a) |
| NS2 | $L_{791} \rightarrow F$ | F (42.3a) |
| NS2 | $T_{804} \rightarrow A$ | A (42.3a) |
| NS5A | $L_{1990} \rightarrow M$ | L (46.5a) |
| NS5A | $I_{2082} \rightarrow T$ | I (46.5a) |
| NS5A | $S_{2174} \rightarrow P$ | (not done) |
| NS5A | $G_{2228} \rightarrow E$ | E (48.6a) |
| NS5A | $T_{2233} \rightarrow S$ | T (48.6a) |
| NS5A | $A_{2236} \rightarrow V$ | A (48.6a) |
| NS5B | $V_{2833} \rightarrow I$ | V (50.7a) |

Example 4

Construction of a Full-Length GBV-B cDNA Clone

The four GBV-B cDNA inserts described above were cloned into Bluescript ks+ using unique restriction sites. Since the unique Sal1 site that was reported to be present in the published GBV-B sequence (nt position 7847) was absent in these cDNA clones, this restriction site was created by engineering two silent nucleotide changes using the "Quick Change" mutagenesis system (Stratagene). Although the most 5' clones (nucleotides 1–7847) could be readily constructed, attempts to add the remaining 3' clones were unsuccessful due to rearrangements and deletions. This problem was overcome by use of pACNR1180, a plasmid that had been used to construct an infectious clone of yellow fever virus. Finally, the most 3' 771 nucleotides of GBV-B were excised from the plasmid containing the novel, previously unreported 3' sequence, and inserted into the truncated assembled GBV-B cDNA construct to complete the 3' end. The 3' terminus of this full-length cDNA was then subjected to DNA sequencing to confirm its integrity. Extensive restriction digests indicated that this construct had the characteristics of a full-length c DNA copy of GBV-B virus. Because there is not yet an understanding of which cultured cells (if any) might be permissive for GBV-B replication, the infectivity of the synthetic GBV-B RNA will be assessed by injecting the RNA directly into the liver of a susceptible tamarin.

Alternatively, an infectious full-length clone can be produced by the following protocol. A plasmid will be made containing a cassette including the 5' and 3' ends of the virus flanked by appropriate restriction sites. These constructs have been shown to efficiently translate reporter genes, with transcription taking place via a T7 promoter placed immediately upstream of the 5'NTR (e.g., see Rijnbrand et al., 1999). The major portion of the GBV-B genome would then be amplified by long range RT-PCR. This method is now well established for hepatitis C virus and other flaviviruses (Teller et al., 1996), and it has been used successfully also to amplify rhinovirus RNA. Briefly this technique uses "Superscript" reverse transcriptase to synthesize cDNA and a mixture of "KlenTaq 1", and "DeepVent" polymerases to amplify this cDNA. Primers that can be used will contain restriction sites to allow cloning of the RT-PCR products into the cassette vector. After being transformed into suitable competent bacteria, extensive restriction analysis will enable us to determine which clones contain inserts that are of full length and which have a high probability of being correct. Apparent full-length clones will be analyzed further by coupled transcription-translation using the Promega "TnT" system, with the addition of microsomal membranes to allow the cleavage of the structural proteins by cellular signalase enzymes. Clones which appear correct by restriction analysis and which produce GBV-B proteins, in particular the protein coded for by the extreme 3' end of the genome, NS5B, will be selected, and RNA will be transcribed from these clones using the Ambion MegaScript system. "Correct" looking clones (>10) can be injected directly into a tamarin liver at several sites. A successful infection will be determined as described below. If a positive signal is detected the entire genome will be amplified and sequenced to determine which plasmid the virus originated from.

Example 5

Rescue of Infectious GVB-B

Infectious GBV-B will be rescued from synthetic genome-length RNA following its injection into the liver of tamarins (*Saquinus* sp.). In past studies, HAV from synthetic RNA in owl monkeys has been recovered (*Aotus trivirgatus*) (Shaffer et al., 1995), and more recently, the recovery of virus from a chimpanzee injected intrahepatically with RNA transcribed from a full-length genotype 1b HCV cDNA clone was reported (Beard et al., 1999).

RNA will be prepared for these studies using the T7 MegaScript kit (Ambion) and a total of 10 μg of plasmid DNA as template. An aliquot of the reaction products will be utilized to ensure the integrity of the RNA by electrophoresis in agarose-formaldehyde gels. The remainder of the transcription reaction mix will be frozen at −80° C. until its injection, without further purification, into the liver of a tamarin. Because of the small size of the tamarin, the RNA will be injected under direct visualization following a limited incision and exposure of the liver. Under similar conditions, in other primate species, RT-PCR-detectable viral RNA or cDNA has not been detected in serum samples collected within days of this procedure in the absence of viral replication (Kolykhalov et al., 1997; Yanagi et al., 1998; Beard et al., 1999). Thus, the appearance of RNA in serum collected subsequently from these tamarins will be strong evidence for the replication competence of the synthetic RNA. Serum will be collected weekly for six weeks, then every other week for an additional 6 weeks from inoculated animals. In addition to RT-PCR for detection of viral RNA (see FIG. 2B), alanine aminotransferase (ALT) levels will be measured as an indicator of liver injury and to assess liver histology in punch biopsies taken at the time of ALT elevation. Maximum viremia and an acute phase ALT response is expected to occur around 14–28 days post-inoculation of infectious RNA (Simons et al., 1995; Schlauder et al., 1995; Karayiannis et al., 1989). Transfections will be considered to have failed to give rise to infectious virus if RNA is not detected in the serum within 12 weeks of inoculation. Successfully infected animals will be followed with twice weekly bleeds until resolution of the viremia, or for 6 months, whichever is longest.

Example 6

Construction of GBV-B/HCV Chimeras

The GBV-B genome can be used as the acceptor molecule in the construction of chimeric viral RNAs containing sequences of both HCV and GBV-B. Such constructs will allow one to investigate the mechanisms for the different biological properties of these viruses and to discover and investigate potential inhibitors of specific HCV activities (e.g., proteinase) required for HCV replication. Different classes of chimeric viruses are contemplated. These include: (a) replacement of the GBV-B IRES with that of HCV; and (b) replacement of the NS3 major serine proteinase and helicase, and (c) the replacement of the NS5B RNA-dependent RNA polymerase with the homologous proteins of HCV.

The chimeric constructs described in the following sections will be made by PCR mutagenesis, using high fidelity polymerases and oligonucleotide primers designed to include the specific fusions of GBV-B and HCV sequences (Landt et al., 1990). First round PCR reactions will create the desired fusion, and generate a new "primer" to be used in a second PCR reaction spanning the region to a convenient unique restriction site. PCR cycles will be kept to the minimum number necessary for successful amplification, and all segments of viral sequence that are amplified by PCR will be subjected to DNA sequencing to exclude the presence of unwanted PCR-introduced errors. Sequencing will be accomplished at UTMB's core Recombinant DNA Laboratory. Amplified segments will be kept to the minimum by the exchange of cloned cDNA segments spanning convenient restriction sites in subgenomic clones, and where necessary PCR artifacts can be corrected by site-directed mutagenesis (QuickChange mutagenesis kit, Stratagene).

A number of viable positive-strand RNA virus chimeras have been constructed previously in which IRES elements have been swapped between different viruses. Most of these chimeras have involved the exchange of IRES elements between picornaviruses. Others have been successful in constructing viable poliovirus chimeras containing the HCV IRES in place of the native poliovirus IRES (Zhao et al., 1999; Lu and Wimmer, 1996). A similar rhinovirus 14 chimera containing the HCV IRES has been constructed, although its replication phenotype is not as robust as the poliovirus chimera described by Lu and Wimmer (Lu and Wimmer, 1996). More importantly, Frolov et al. (Frolov et al., 1998) recently reported chimeric flaviviruses in which the HCV IRES was inserted into the genetic background of a pestivirus, bovine viral diarrhea virus (BVDV) in lieu of the homologous BVDV sequence. Although these viable chimeric polioviruses and pestiviruses replicate in cell cultures, they are poor surrogates for HCV in animal models as neither virus is hepatotropic or causes liver disease. Importantly, Frolov et al. (Frolov et al., 1998) demonstrated quite convincingly that the requirement for cis-acting replication signals at the 5' terminus of the pestivirus genome was limited to a short tetranucleotide sequence. This requirement presumably reflects the need for the complement of this sequence at the 3' end of the negative strand during initiation of positive-strand RNA synthesis. The work of Frolov et al. shows that the IRES of BVDV does not contain necessary replication signals, or that if these are present within the BVDV IRES they can be complemented with similar signals in either the HCV or encephalomyocarditis virus (EMCV, a picornavirus) IRES sequence. Since GBV-B and HCV are more closely related to each other than BVDV and HCV, these studies provide strong support for the viability of chimeras containing the HCV IRES in the background of GBV-B.

Construction of a viable IRES chimera will be enhanced by studies that have documented the sequence requirements and secondary structures of the IRES elements of both HCV and GBV-B (see Lemon and Honda, 1997; Honda et al., 1996; Rijnbrand et al., 1999). To a considerable extent, the work of Frolov et al. (Frolov et al., 1998) was guided by studies of the HCV IRES structure. More recently, these studies have been extended to include a detailed mutational analysis of the GBV-B IRES. The results of these studies indicate that the functional IRES of GBV-B extends from the 5' end of structural domain II (nt 62) to the initiator AUG codon (nt 446). This segment of the full-length GBV-B clone will be replaced with HCV sequence extending from 5' end of the analogous domain II within the HCV IRES (nt 42) to the initiator codon at the 5' end of the HCV open reading frame (nt 341) to construct the candidate chimera, "GB/C:IRES". The source of HCV cDNA for these studies will be the infectious HCV clone, pCV-H77C, which contains the sequence of the genotype 1a Hutchinson strain virus (Yanagi et al., 1998), whose infectivity in a chimpanzee following intrahepatic inoculation with synthetic RNA transcribed from pCV-H77C has been confirmed.

This GB/C:IRES construct will retain two upstream hairpins within the GBV-B sequence (stem-loops Ia and Ib), and it is thus analogous to the viable "BVDV+HCVdel B2B3H1" chimera of Frolov et al (Frolov et al., 1998). A second chimera can be constructed in which the entire HCV 5' nontranslated RNA will be inserted in lieu of nts 62–446 of the GBV-B genome ("GB/C:5'NTR"). This construct will add to the inserted HCV sequence the most 5' stem-loop from HCV (stem-loop T). A similar insertion was shown to substantially increase the replication capacity of BVDV+HCVdel B2B3H1 by Frolov et al. (Frolov et al., 1998), providing a replication phenotype similar to wild-type BVDV in cell culture.

It is important to point out that there is strong evidence from multiple lines of investigation indicating that it will not be necessary to include coding sequence in these IRES chimeras. This is the case even though Reynolds et al. (Reynolds et al., 1995) have argued that the HCV IRES extends past the initiator codon, and into the core-coding region of that virus. Although Lu and Wimmer (Lu and Wimmer, 1996) found it necessary to include HCV core sequence to obtain a viable chimeric poliovirus, the BVDV chimeras reported by Frolov et al. (Frolov et al., 1998) did not contain any HCV coding sequence. This discrepancy may be explained by the observation that the only downstream requirement for full activity of both the GBV-B and HCV IRES elements is the presence of an unstructured RNA segment (Honda et al., 1996; Rijnbrand et al., 1999). Presumably, this facilitates interaction of the viral RNA with the 40S ribosome subunit in the early steps of cap-independent translation (Honda et al., 1996). The 5' GBV-B coding sequence fulfills this criterion (Rijnbrand et al., 1999).

Example 7

In Vitro Characterization of the Translational Activity of IRES Chimeras

The fidelity of the genome-length chimeric constructs will be confirmed by sequencing any DNA segments that have been subjected to PCR during the construction process, as well as confirming sequence at the junction sites. In addition, the translational activity of synthetic RNA derived from these constructs will be assessed and compared to the translational activity of the wild-type GBV-B and HCV RNAs. These studies will be carried out in a cell-free translation assay utilizing rabbit reticulocyte lysates (Rijnbrand et al, 1999). Synthetic RNA will be produced by runoff T7 RNA polymerase transcription using as template ClaI-digested plasmid DNA (BamHI digestion in the case of the genome HCV construct) (T7 Megascript kit, Ambion). $^3$H-UTP will be added to the reaction mix to allow for quantification of the RNA product. Reticulocyte lysates (Promega) will be programmed for translation by the addition of RNA (at least 50% full-length as determined by agarose gel electrophoresis) at 20, 40 and 80 µg/ml, and translation reactions will be supplemented with microsomal membranes (Promega). $^{35}$S-Methionine-labelled translation products will be separated by SDS-PAGE, and the quantity of E1 protein produced from each RNA determined by PhosphorImager analysis (Molecular Dynamics). Comparisons of the activity of the HCV IRES in the background of GBV-B and HCV will take into account differences in the methionine content of the E1 proteins of these viruses. Based on previous studies of both the GBV-B and HCV IRES elements (Honda et al., 1996; Rijnbrand et al., 1999), it is expected that these studies will confirm that the HCV IRES will retain nearly full activity when placed within the GBV-B background.

Example 8

In Vivo Characterization of IRES Chimeras

Synthetic RNAs produced from each of the two chimeric GBV-B/HCV constructs (GB/C:IRES and GB/C:5'NTR) will be tested for their ability to induce infection and cause liver disease in susceptible tamarins. These studies will be carried out as described in Example 2. GB/C:5'NTR may generate viremia and liver injury more closely resembling that observed with wild-type GBV-B infection (Frolov et al., 1998).

Example 9

Chimeric Flaviviruses Containing the HCV NS3 Serine Proteinase/Helicase within the GBV-B Background Chimeric flaviviruses containing the HCV NS3 serine proteinase/helicase within the GBV-B background are also contemplated within the present invention. The construction of chimeric flaviviruses containing specific heterologous functional polyprotein domains, however, poses a number of special problems. Unlike the situation with the IRES, where the relevant RNA segments appear to have a unique function restricted to cap-independent translation initiation and interact with host cell macromolecules, viral proteins often have multiple functions and may form specific macromolecular complexes with other viral proteins that are essential for virus replication (Lindenbach and Rice, 1999). Furthermore, such chimeric polyproteins must be amenable to efficient processing by the viral proteinases (NS2/NS3 or NS3). This requires knowledge of the proteinase cleavage specificities as well as specific sites of proteolytic cleavage. Although to date there have been no published studies of the processing of the GBV-B polyprotein, the relatively close relationship between GBV-B and HCV, about 30% overall amino acid identity within the polyprotein (Muerhoff et al., 1995), allows good computer predictions of the alignments of these proteins. The crystallographic structures of both the proteinase and helicase domains of the HCV NS3 protein have been solved (Yao et al., 1997). Thus, both linear alignments and models of the 3D structure of the NS3 proteins of these viruses can provide guidelines for designing specific chimeric fusions that are likely to preserve function.

Example 10

NS3 Proteinase-Domain Chimeras

In HCV, NS3 contains the major serine proteinase that is responsible for most cleavage events in the processing of the nonstructural proteins, i.e., those that occur at the NS3/4A, 4A/4B, 4B/5A and 5A/5B junctions. The active proteinase domain of HCV is located within the amino terminal third of the NS3 protein (residues 1–181), which shares 31% amino acid identity with the analogous segment of the GBV-B polyprotein (GBV-B vs HCV-BK) (Muerhoff et al., 1995). Importantly, the active site of this proteinase appears to be particularly well conserved in GBV-B. The GBV-B proteinase maintains the residues that are responsible for catalysis and zinc binding in the HCV enzyme (Muerhoff et al., 1995), and unlike the NS3 proteinases of some other flaviviruses preserves the Phe-154 residue that determines in part the $S_1$ specificity pocket of the enzyme and the preference of the HCV proteinase for substrates with a cysteine residue at the P1 position (Scarselli et al., 1997). Thus, it is not surprising that the relevant proteolytic cleavage sites within the GBV-B polyprotein that are predicted from alignments with the HCV polyprotein all possess a Cys residue at this position. Of greatest significance for the proposed studies, however, is the work of Scarselli et al. (Scarselli et al., 1997) who demonstrated that the GBV-B NS3 proteinase is able to effectively process the polyprotein of HCV in studies carried out in vitro. Using synthetic peptide substrates, these investigators demonstrated that the enzymatic activities of the GBV-B proteinase (residues 1–181) had kinetic parameters similar to the HCV proteinase on NS4A/4B and NS4B/4A substrates HCV. They did not possess reagents allowing a determination of whether the HCV proteinase is able to cleave a GBV-B substrate, but their results indicate that these viral proteinases share important functional properties.

Therefore, these similarities suggest that the HCV proteinase could function in lieu of the GBV-B proteinase if used to replace this segment of an infectious GBV-B clone. In addition, studies with sindbis/HCV chimeras have shown that the HCV proteinase can cleave within the framework of a sindbis polyprotein (Filocamo et al., 1997).

In considering the design of these NS3 proteinase chimeras, there are two additional important considerations. First, in HCV, the cleavage between NS2 and NS3 occurs in cis, as the result of a zinc-dependent metalloproteinase that spans the NS2/NS3 junction (Hijikata et al., 1993). As only the NS3 sequences will initially be exchanged, the viability of the resulting chimeras will be dependent upon preservation of the cis-active cleavage across a chimeric NS2/NS3 proteinase domain. The alignment of GBV-B and HCV sequences shows that residues in HCV that have been shown by Grakoui et al., 1993, to be essential for the NS2/NS3 cleavage are conserved in GBV-B (Muerhoff et al., 1995). Additional chimeras that will include the relevant carboxyl-terminal portion of NS2 can also be created.

A second important consideration is that the mature HCV NS3 proteinase functions as a noncovalent assembly of the NS3 proteinase domain and the amino terminal portion of NS4A, a proteinase accessory factor. The details of this association are well known, and have been studied at the crystallographic level (Kim et al., 1996). The N-terminal domain of the folded proteinase contains eight β strands, including one contributed directly by the NS4A peptide backbone. X-ray studies have shown that this array of β strands gives rise to a much more ordered N-terminus. Thus, the presence of the NS4A strand seems likely to contribute to the structure of the substrate-binding pocket. It is not known whether the NS3 proteinase of GBV-B also requires a similar interaction with NS4A of that virus for complete activity, or, if so, whether the NS4A of GBV-B could substitute for NS4A of HCV in forming the fully active NS3 proteinase of HCV. The predicted GBV-B NS4A molecule is 54 amino acid residues in length (Simons, et al., 1995; Muerhoff et al., 1995), just as in HCV. However, the level of amino acid homology between the NS4A molecules is not especially high, and the potential interaction with either NS3 molecule cannot be predicted from this sequence on the basis of available knowledge. To overcome this potential problem, chimeras will be created in which not only the NS3 proteinase domain of GBV-B is replaced, but also the relevant NS4A segment as well, with homologous segments of the HCV polyprotein. The interaction of the HCV NS3 and NS4A domains represents a unique target for antiviral drug design, and it would be beneficial to have this specific interaction present in any virus to be used as a surrogate for HCV in the evaluation of candidate antiviral inhibitors of HCV proteinase in vivo.

The NS3 proteinase chimeras that can be made include "GB/C:NS3$^P$", which will contain the sequence encoding the first 181 amino acid residues of the HCV NS3 molecule in lieu of that encoding the first 181 residues of GBV-B NS3, and "GB/C:NS3$^P$4A", which will include the same NS3 substitution as well as the HCV sequence encoding the amino-terminal segment of NS4A that forms the interaction with NS3. The precise NS4A sequence to be included in the latter chimera will be based on the modeling studies, which may also suggest more effective fusions of the NS3 proteinase domain of HCV with the downstream NS3 helicase domain of GBV-B. The source of HCV cDNA for these studies will be the infectious HCV clone, pCV-H77C, which contains the sequence of the genotype 1a Hutchinson strain virus (Yanagi et al., 1998).

Example 11

NS3 Helicase Domain Chimeras

Figure 5:
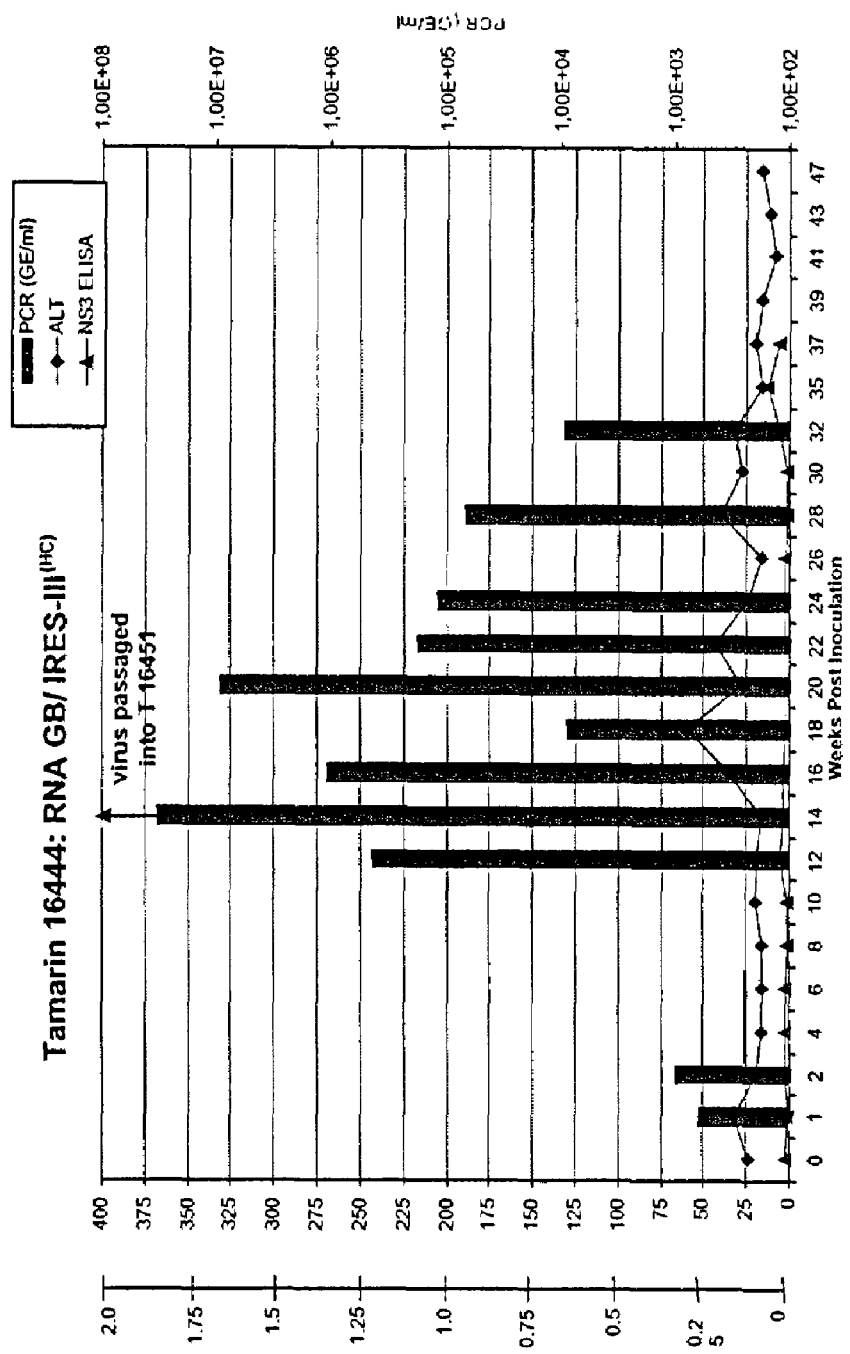
FIG. 5. Shows the replication of an exemplary III$^{HC}$ chimeric RNA following intrahepatic inoculation of synthetic RNA in a GBV-B naïve tamarin (S. mystax).
Figure 6:
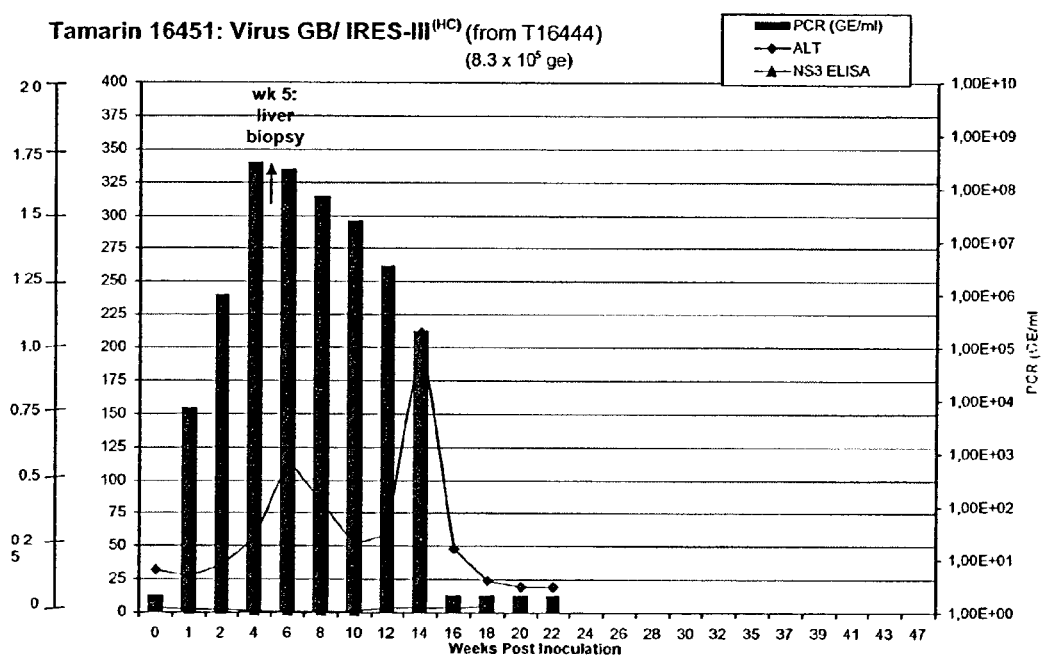
FIG. 6. Shows the replication of an exemplary III$^{HC}$ chimeric virus following intravenous inoculation of a GBV-B naïve tamarin (S. mystax) with virus present in the serum of T16444 14 weeks after it had been inoculated with synthetic RNA.

In addition to serine proteinase activity located within the amino-third of NS3, the downstream carboxy-terminal two-thirds of the molecule contains an RNA helicase activity. These two functional domains appear to be separated by a flexible spacer, within which the fusion of HCV proteinase or helicase domain sequences with GBV-B sequence will be placed. The exact role of the helicase in the HCV life-cycle is not known, but it is almost certainly required for dsRNA strand-separation during some phase of viral RNA synthesis. The helicase domains of GBV-B and HCV are remarkably well conserved, with some regions within the helicase showing as much as 55% amino acid identity (Muerhoff et al., 1995). The GBV-B helicase is more closely related to the HCV helicase than all other flaviviral NS3 helicases, and it preserves many residues found within the conserved helicase motifs of HCV. Thus the HCV NS3 helicase may be capable of functioning when placed within the polyprotein of GBV-B, and such a chimeric virus may be capable of replication. Residues 182–620 of the GBV-B NS3 molecule will be substituted with the analogous segment of HCV (FIG. 5, "GB/C:NS3$^{h}$"). A chimera will also be made in which the entire NS3 and amino terminal NS4 protein sequences of GBV-B is replaced with the homologous HCV sequences ("GB/C:NS3-4A"). The latter construct will thus represent a dual proteinase-helicase chimera. As with the proteinase chimeras, the HCV cDNA will be derived from pCV-H77C (Yanagi et al., 1998).

Example 12

In Vitro Characterization of NS3 and NS3-NS4A Chimera

Prior to being evaluated for infectivity in susceptible tamarins, RNAs produced in vitro from these clones will characterized in vitro. This evaluation will be restricted to a documentation of the proper processing of the expressed polyprotein (i.e., NS2/NS3 and NS3 proteinase functions), since there are no relevant assays that can determine whether the helicase or RNA-dependent RNA polymerase activities in these polyproteins are sufficient for virus replication. The proteolytic processing of the polyprotein is important, however, as it may be altered either by inclusion of the heterologous HCV NS3 proteinase in lieu of the natural GBV-B protease, or by a change in the folding of the polyprotein induced by inclusion of HCV sequence anywhere within the polyprotein. These studies will be carried out in cell-free coupled transcription/translation assays ("TnT" system, Promega) supplemented with microsomal membranes. Template DNAs will be digested with SalI, which restricts the cDNA within the NS5B coding region. $^{35}$S-methionine-labelled translation products will be separated by SDS-PAGE, and the mature NS3 protein identified by its apparent molecular mass. The NS3 and NS5B proteins will be identified by immunoblot analysis using rabbit antisera to the GBV-B NS3 and NS5B proteins. Generation of a mature ~68 kDa NS3 protein will provide proof of both the cis-active NS2/NS3 cleavage and the NS3-mediated cleavage of NS3/NS4A. Similarly, identification of a mature, processed NS5B molecule will provide further support for the activity of the NS3 proteinase. Controls for these studies will be the wild-type GBV-B polyprotein expressed in similar fashion from the full-length GBV-B clone. If necessary to more clearly demonstrate the processing of the nonstructural proteins in these constructs, subclones representing the nonstructural region of the chimeric sequences could be produced.

Example 13

In Vivo Characterization of NS3 and NS3-4A Chimeras

Synthetic RNAs produced from each of the chimeric GBV-B/HCV constructs described in the preceding section will be tested for their ability to induce infection and cause liver disease in susceptible tamarins. These studies will be carried out using the approach described above.

Example 14

Chimeric Flaviviruses Containing the HCV NS5B RNA Dependent RNA Replicase within the GBV-B Background The HCV NS5B molecule contains an RNA-dependent RNA polymerase that plays a central role in replication of the virus. Although this molecule represents a prime target for drug discovery efforts, it has proven difficult to express NS5B in a form that retains enzymatic activity specific for HCV RNA as a substrate. Thus, relatively little is known of the functional activity of the HCV replicase, including structure-function relationships of NS5B. Despite this, the NS5B proteins of GBV-B and HCV appear to be functionally closely related, as they share as much as 43% amino acid identity (Muerhoff et al., 1995). A more important question may be whether an RNA dependent RNA polymerase can act on foreign substrates. However, published work has shown that in vitro purified HCV polymerase has very little specificity for its template, using hepatitis C or globin message with equal fidelity (Behrens et al., 1996; Al et al., 1998). This finding is very similar to that obtained with picornaviral polymerases, where it has been known for many years that in vitro the enzyme exhibits very little specificity. It has always been considered highly likely that this situation would not pertain in vivo where it was thought that the interaction of viral or cellular factors with the 3' end of the genome would generate template specificity. However, recent reports have shown that the removal of the entire 3' untranslated sequence (leaving, however, the poly(A) region present) from both the poliovirus and rhinovirus genome does not completely abrogate the infectivity of the virus (Todd et al., 1997). Furthermore, virus, which was recovered after the initial transfections, was shown to have recovered much of the infectivity of the original virus (Todd et al., 1997). The mechanism for this recovery of infectivity is at present unknown, but these results suggest that the HCV polymerase may be able to function to replicate infectious GBV-B/HCV NS5B chimeras.

Thus a chimeric genome-length virus can be created in which the NS5B coding sequence of HCV (amino acids 2422–3014, 593 residues) is inserted within the background of GBV-B in lieu of its native RNA-dependent RNA polymerase (amino acids 2274–2864, 591 residues). This chimeric virus would be valuable for animal studies of candidate antiviral inhibitors of HCV RNA synthesis.

This NS5B chimera would be evaluated to determine that there was proper proteolytic processing of the polyprotein. This would be accomplished by expression of the chimeric polyprotein in a coupled translation-transcription reaction, followed by immunoblot analysis for the mature NS5B protein, as described for the NS3 and NS3–4A chimeras in the preceding section. If these results confirm that the GB/C:5B chimeric polyprotein is processed with release of NS5B, studies in tamarins would progress to determine whether synthetic RNA transcribed from the clone is infectious and capable of causing liver disease in intrahepatically inoculated animals. These studies would be carried out as described above.

A chimeric molecule can be constructed from an infectious GBV-B clone in which the HCV NS3 proteinase or proteinase/helicase sequence would be placed in frame in lieu of the homologous GBV-B sequence, and this chimeric cDNA would be used to generate infectious GBV-B/HCV chimeric viruses by intrahepatic inoculation of synthetic RNA in tamarins. Published studies indicate that the GBV-B and HCV proteinases have closely related substrate recognition and cleavage properties, likely making such chimeras viable and capable of initiating viral replication in appropriate cell types.

Example 15

Chimeric Viruses Containing HCV Structural Proteins within a GBV-B Genetic Background, and GBV-B Structural Proteins within an HCV Background It is well documented that the structural proteins of one flavivirus may in some cases be substituted for those from another member of the family. Such chimeric viruses have been recovered from viruses as distantly related to each other as dengue virus and tick-borne encephalitis virus (Pletnev et al., 1992). More recently, the prM and E proteins of Japanese encephalitis virus have been used to replace the equivalent proteins in a vaccine strain of yellow fever virus to produce a JE/YF chimera (Chambers et al., 1999). These observations suggest that chimeras in which the structural proteins of HCV have been used to replace the homologous proteins of GBV-B may well be viable and capable of replication. The isolation of a chimeric virus containing HCV structural proteins, but having the growth characteristics of GBV-B virus, could answer many fundamental questions concerning the structure and interaction of these proteins in HCV. They would also be useful in addressing the nature of the immune response to HCV structural proteins in infected primates (Farci et al., 1992). More to the point of this application, the availability of such chimeric viruses would allow studies of candidate HCV vaccines to be carried out in the tamarin model. This would be a major advance, because at present such studies are limited to chimpanzees (Choo et al., 1994).

The basis for the difference in the host ranges of HCV and GBV-B is completely unknown. Among many other possibilities, it is conceivable that the host range is dependent upon the availability of a specific receptor(s). If this were the case, host range might be dependent upon the envelope proteins that must interact with the putative cellular receptor. Thus, a chimeric virus containing the envelope proteins of HCV within the genetic background of GBV-B might be noninfectious in tamarins (but potentially infectious in chimpanzees). Thus, a finding that both structural protein chimeras are noninfectious in the tamarin, may require the construction of complementary chimeras in which the relevant GBV-B structural proteins will be inserted into the background of an infectious HCV clone. If inclusion of the GBV-B envelope proteins within the backbone of HCV confers on the resulting chimera the ability to replicate in tamarins, it will confirm an important role for the structural proteins in defining the different host ranges of these viruses. More importantly, the resulting virus would be an exceptionally valuable resource for future studies as it would contain all of the nonstructural replication elements, as well as the 5' and 3' nontranslated regions, of HCV. Such a virus would allow the tamarin model to be used to address many unresolved issues in HCV biology and pathogenesis.

Example 16

Construction and Evaluation of Structural Protein Chimeras

In designing structural protein chimeras, it is important to note that the two envelope proteins of HCV, E1 and E2, form noncovalent heterodimeric complexes that are likely to be important in the assembly of infectious virus particles. This is not known to be the case with the envelope proteins of GBV-B, but it is likely given similarities in the sizes and hydropathy profiles of these proteins (Simons et al., 1995; Muerhoff et al., 1995). Accordingly, the E1 and E2 proteins will be replaced as a unit, and chimeras containing only one of these proteins from the heterologous virus will generally not be produced. First, a chimera will be created where the E1 and E2 regions of GBV-B virus are replaced with those of HCV, "GB/C:E1–2". The source of HCV cDNA for these constructions will be pCV-H77C (Yanagi et al., 1998). A chimera will also be made in which the core protein, in addition to the envelope proteins, is replaced with the homologous proteins of HCV ("GB/C:Co-E2"). Additional chimeras will be made to determine whether tamarins can be infected with chimeras containing the GBV-B structural proteins within the genetic background of HCV. These will include "C/GB:E1–2" and "C/GB:Co-E2". The backbone for these chimeras will be pCV-H77C, the infectious genotype 1a cDNA clone developed in the Purcell laboratory at NIAID (Yanagi et al., 1998).

The specific amino acid sequences of GBV-B to be replaced with the homologous segments of HCV have been determined by alignments of the GBV-B and HCV sequences, coupled with the location of signalase cleavage sites predicted to be present within the amino terminal third of the GBV-B polyprotein using the computer algorithm of Von Heijne. These predicted signalase cleavages lie between residues 156/157 (core/E1), aa 348–349 (E1/E2) and 732/733 (E2/NS2) in the GBV-B sequence. Thus, the chimera GB/C:E1–2 will contain sequence encoding HCV aa 192–809 in lieu of that encoding aa 157–732 in GBV-B, while the insertion in the GB/C:Co-E2 chimera will extend from the initiator AUG codon (aa 1) to residue 809 in HCV, and will be spliced into GBV-B in lieu of the segment encoding aa 1–732 in the GBV-B clone. The complementary chimeras to be constructed within the background of HCV will involve exchanges of the same segments of the genomes.

Example 17

Characterization of Structural Protein Chimeras

Prior to being evaluated for infectivity in tamarins, the processing of these chimeric polyproteins will be examined in coupled transcription/translation reactions supplemented with microsomal membranes, as described in the preceding sections for the proteinase and other proposed chimeras. If these results confirm that the polyprotein is processed as expected, with production of glycosylated E1 and E2 proteins from each of the chimeras (and seen in similar studies with HCV proteins), studies would proceed in tamarins as previously described. The results of these studies may provide novel information on the basis of the host range differences that exist between HCV and GBV-B. If these results suggest that the envelope proteins play a critical role in determining host range, additional studies could be carried out with these chimeras in chimpanzees (which are permissive for HCV but apparently not for GBV-B).

Example 18

Further Characterization of Rescued Chimeric Viruses

Where infection with chimeric viruses is induced in animals that are injected within the liver with synthetic RNA, this virus will be passaged in GBV-B naïve tamarins to further characterize the nature of the infection induced by the chimera. This will be accomplished by taking a pool of the 3 highest titer GBV-B RNA-containing serum specimens from the animal that was successfully transfected with RNA, and inoculating 1 mL of a 1:100 dilution of this pool intravenously into two susceptible animals. These animals will be monitored for infection and liver disease. These animals will be followed until resolution of the viremia and appearance of antibodies detectable in immunoblots with GST-NS3 protein expressed in E. coli, or for at least 6 months should an animal sustain a chronic infection. RT-PCR amplification of chimeric segments of the genome may be employed to determine whether the altered phenotype results from mutations within the heterologous portion of the genome.

Example 19

Use of GBV-B as Model for HCV

GBV-B and/or GBV-B/HCV chimeras can be used as a model for HCV. Such studies will allow one to investigate the mechanisms for the different biological properties of these viruses and to discover and investigate potential inhibitors of specific HCV activities (e.g., proteinase) required for HCV replication.

Example 20

Use of GBV-B/HCV Chimeras to Test Candidate HCV NS3 Proteinase Inhibitors or Other Inhibitors of HCV GBV-B/HCV viruses can be used in preclinical testing of candidate HCV NS3 proteinase inhibitors or other inhibitors of HCV.

1. Candidate Substances

As used herein the term "candidate substance" refers to any molecule that is capable of modulating HCV NS3 proteinase activity or any other activity related to HCV infection. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known modulators of HCV NS3 proteinase activity. The active compounds may include fragments or parts of naturally-occurring compounds or may be only found as active combinations of known compounds that are otherwise inactive. However, prior to testing of such compounds in humans or animal models, it will be necessary to test a variety of candidates to determine which ones have potential.

Accordingly, the active compounds may include fragments or parts of naturally-occurring compounds or may be found as active combinations of known compounds that are otherwise inactive. As such, the present invention provides screening assays to identify agents that are capable of inhibiting proteinase activity in a cell infected with chimeric GBV-B/HCV viruses containing the HCV proteinase. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of proteinases or from structural studies of the HCV proteinase.

The candidate screening assays are simple to set up and perform. Thus, in assaying for a candidate substance, after obtaining a chimeric GBV-B/HCV virus with infectious properties, a candidate substance can be incubated with cells infected with the virus, under conditions that would allow measurable changes in infection by the virus to occur. In this fashion, one can measure the ability of the candidate substance to prevent or inhibit viral replication, in relationship to the replication ability of the virus in the absence of the candidate substance. In this fashion, the ability of the candidate inhibitory substance to reduce, abolish, or otherwise diminish viral infection may be determined.

"Effective amounts" in certain circumstances are those amounts effective to reproducibly reduce infection by the virus in comparison to the normal infection level. Compounds that achieve significant appropriate changes in activity will be used. Candidate compounds can be administered by any of a wide variety of routes, such as intravenously, intraperitoneally, intramuscularly, orally, or any other route typically employed.

It will, of course, be understood that all the screening methods of the present invention are useful in themselves notwithstanding the fact that effective candidates may not be found. The invention provides methods of screening for such candidates, not solely methods of finding them.

2. In Vitro Assays

In one particular embodiment, the invention encompasses in vitro screening of candidate substances. Using a cell line that can propagate GBV-B in culture, in vitro screening can be used such that GBV-B or HCV virus production or some indicator of viremia is monitored in the presence of candidate compounds. A comparison between the absence and presence of the candidate can identify compounds with possible preventative and therapeutic value.

3. In Vivo Assays

The present invention also encompasses the use of various animal models to test for the ability of candidate substances to inhibit infection by HCV. This form of testing may be done in tamarins.

The assays previously described could be extended to whole animal studies in which the chimeric virus could be used to infect a GBV-B permissive primate, such as a tamarin. One would then look for suppression of viral replication in the animal, and a possible impact on liver disease related to replication of the infectious chimeric virus. The advantage of this in vivo assay over present available assays utilizing HCV infection in chimpanzees is the reduced cost and greater availability of GBV-B permissive nonhuman primate species.

Treatment of animals with test compounds will involve the administration of the compound, in an appropriate form, to the animal. Administration will be by any route that could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, intraperitoneal injection, and oral administration.

Determining the effectiveness of a compound in vivo may involve a variety of different criteria. Such criteria include, but are not limited to, survival, reduction of rate of infection, arrest or slowing of infection, elimination of infection, increased activity level, improvement in liver function, and improved food intake.

Example 21

Use of Infectious GBV-B/HCV Chimeras as Vaccines

Infectious GBV-B/HCV chimeras expressing HCV envelope proteins will have utility as a vaccine immunogen for hepatitis C. Such clones clearly have the potential to be constructed as chimeras including relevant hepatitis C virus sequences in lieu of the homologous GBV-B sequence, providing unique tools for drug discovery efforts.

Chimeric viruses containing the envelope proteins of hepatitis C virus (as described in the attached) would confer the antigenic characteristics of hepatitis C virus on the chimera. These chimeras may have the ability to replicate in chimpanzees (and thus humans) by virtue of the fact that the chimeric envelope is now able to interact with the human hepatocyte cell surface, a necessary first step in virus replication. Therefore, the chimeric virus, while able to infect and replicate in humans, may not cause much or any disease-the reasoning here is that the genetic backbone of the chimera that encodes the nonstructural proteins of GBV-B has not evolved for replication in human cells and thus may not replicate well. Thus, the chimera may have limited replication ability, cause no disease, but still elicit immunity to the surface envelope proteins of HCV and thus have potential as a hepatitis C vaccine. These chimeras can be tested for their ability to promote immunity to HCV through an immune response.

Example 22

Construction of a GBV-B Infectious Clone

A genome-length cDNA copy of the complete GB virus B (GBV-B) genome sequence, including the novel 3' terminal sequence, was assembled from fragments amplified by reverse transcription-polymerase chain reaction (RT-PCR) from viral RNA present in a 0.2 µl aliquot of infectious serum (GB agent pool mystrax 666, August 1993) supplied by Dr. Jens Bukh of the National Institutes of Health. The serum sample was diluted with 100 µl of fetal calf serum and extracted using the Trizol system (GIBCO/BRL). The pellet was dissolved in 10 mM dithiothreotol containing 20 u/mL RNasin (Promega). The selection of primers for cDNA synthesis and PCR amplification was based on the published sequence of GBV-B (Simons et al., 1995). RT/PCR was carried out using Superscript Reverse Transcriptase (GIBCO/BRL) and the Advantage cDNA PCR Kit (Clontech). Four subgenomic regions were amplified covering the entire published GBV-B genome sequence. A fifth subgenomic region included the novel 3' terminal sequence that was identified in our laboratory. The oligonucleotide primer sets (listed 5'→3') used for amplification of the individual regions included:

```
Primer 1: CGGGATCCCGTAATACGACTCACTATAGACCACAAACACTCCAGTTTG  (SEQ ID NO:3)
Primer 2: GTGGAATTCACAGCGTCATA                              (SEQ ID NO:4)
```

(Places a T7 RNA polymerase promoter sequence immediately upstream of the GBV-B sequence; the amplified segment extends from the 5' terminus of the viral genome to the unique EcoRI site at position 1978.)

```
Primer 3:   TGTGAATTCCACTCTCCTACC    (SEQ ID NO:5)
Primer 4:   TTATCGATTGCAGCAACCATG    (SEQ ID NO:6)
```

Overlapping EcoRI site at position 1978 and the unique ClaI site at 5327.)

```
                                                            (SEQ ID NO:7)
Primer 5:  CATGGTTGCTGCAATCGATAAGCTGAAGAGTACAATAAC (SEQ ID NO:8)
Primer 6:  GACAACAGACGCTTGACACG
```

(Overlapping the Cla I site at 5327 and a unique Sal I site at 7847 in the published sequence: however, the Sal I site was not present in the amplified GBV-B sequence, and was thus introduced into the cDNA using the QuikChange Site-directed Mutagenesis Kit (Stratagene).)

```
Primer 7: CTGTCATGGGAGATGCGTAC                              (SEQ ID NO:9)
Primer 8: CGAGCTCGAGCACATCGCGGGGTCGTTAAGCCCGGGGTCTCC        (SEQ ID NO:10)
```

(Overlapping the Sal I site at 7847 and the published 3' end of the genome.)

```
Primer 9:
GACAACAGACGCTTGACACG                                        (SEQ ID NO:11)

Primer 10:
CCGACTCGAGAATTCGGCCCTGCAGGCCACAACAGT (SEQ ID NO:12)

CTCGCGAGTTTTTAATTCCAAGCGGGGGTTGCCCTC

CGCTTGGAACAAAAACCGGGGTGCAGCCCTTGGTAC
```

(Overlaps product of primers 7 and 8 and extends to the novel 3' terminal sequence; includes an Xho I site at the 3' terminus of the GBV-B sequence to aid subsequent manipulations.)

RT-PCR products were gel-purified using the QIAquick Gel Extraction Kit (Qiagen) and ligated into a plasmid vector with the PstBlue-1 Perfectly Blunt Cloning Kit (Novagene). Bacterial colonies were screened for plasmid DNAs with the correct insert size. Those harboring an insert of the approximate correct size were subjected to diagnostic restriction analysis. cDNA inserts generating the appropriate restriction patterns were sequenced in both directions using an ABI DNA sequencer, and those with sequences closest to the published GBV-B sequence (Simons et al., 1995) were selected for subsequent assembly into the full-length clone.

The cloned overlapping cDNA fragments were assembled into the pACNR1180 plasmid using the unique restriction sites noted in the primer descriptions. The final, fully assembled plasmid bearing a 9.4 kb cDNA GBV-B insertion was subjected to DNA sequencing to confirm the validity of the construction and the absence of any mutations or errors in the sequence that may have been introduced during the assembly process. The sequence of the GBV-B infectious cDNA is shown in SEQ ID NO:2.

Plasmid DNA containing the GBV-B cDNA was purified by isopycnic centrifugation on a CsCl gradient and isolated by ethanol precipitation. The plasmid DNA was linearized at the 3' terminus of the cDNA insert by digestion with Xho I. Two μg of the linearized DNA was used as template in an in vitro transcription reaction using the Ambion T7 MEGAscript Kit according to the manufacturer's instructions. The integrity of the resultant synthetic RNA product was confirmed by nondenaturing agarose gel electrophoresis.

Approximately 60 μg of RNA transcribed from the GBV-B cDNA clone was diluted in phosphate buffered saline and injected under direct visualization at laparotomy into the liver of a healthy tamarin without a prior history of GBV-B infection (*Saguinus oedipus*). Serum samples were collected from the animal weekly beginning at 2 weeks post-inoculation and tested for the presence of GBV-B RNA by real-time quantitative RT-PCR (TaqMan assay). Results are shown in the following table.

| Week Postinoculation | Genome equivalents/ml |
| --- | --- |
| 0 | 0 |
| 2 | $8.3 \times 10^3$ |
| 3 | $6.6 \times 10^5$ |
| 4 | $4.6 \times 10^8$ |

The presence of high and increasing titers of viral RNA in the serum of this animal between 2–4 weeks postinoculation confirms the infectivity of the full-length cDNA clone containing the novel 3' terminal sequence. The presence of viremia demonstrated that viral replication had ensued following the delivery of the synthetic viral RNA to hepatocytes.

Example 23

Construction of a Chimeric Virus Containing the Domain III of the 5' NTR of HCV (IRES) within the Genetic Background of GBV-B.

1. Construction of Plasmids Containing Chimeric cDNAs.

As described herein, a genome-length molecular clone of GBV-B was assembled from a series of overlapping cDNA fragments produced by RT-PCR from viral RNA isolated in a GBV-B-infected tamarin serum. This clone incorporates the novel GBV-B 3' NTR sequence, as described herein. The cDNA has been placed downstream of a T7 RNA polymerase promoter in the context of the bacterial vector pACNR1180. To facilitate further cloning steps, a C→T substitution was introduced at nucleotide (nt) position 496 of the GBV-B cDNA, so that a unique MluI restriction site was generated in the core-coding sequence without modifying the amino acid sequence. The resulting plasmid containing the full-length GBV-B cDNA with the engineered MluI site at nt position 491 will be referred to as pGBV-B/Mlu. Chimeric GBV-B/HCV 5'NTRs were generated by substituting domains of the GBV-B 5'NTR by HCV counterparts using a gene fusion PCR strategy (Landt et al., 1990) and HCV sequences derived from Hutchinson strain of genotype 1a, Genbank accession numbers AF011751 (SEQ ID NO:13), AF011752, and AF011753, each of which is incorporated herein by reference (Inchauspe et al., 1991). The invention is not limited to a particular strain of HCV and sequences found in other HCV sequences may also be used, such as Genbank accession numbers AF009606, M67463, AF290978, AF387806, AF271632, M62321, AF387807, AF387805, AF387808, D10749, AF511948, AF177040, AF177038, AF177039, AF177037, AF511949,or M32084, each of which is incorporated herein by reference. Chimeric 5'NTRs were amplified using overlapping PCR fragments spanning the desired HCV region framed by appropriate GBV-B regions, so that the BamHI restriction site located upstream of the T7 promoter sequence and the MluI restriction site (nt 491) were used to substitute the parent GBV-B fragment within the molecular infectious clone. The sequence of all PCR-amplified fragments within the resulting, chimeric pGB/I-II-III$^{HC}$, pGB/ΔIb/II-III$^{HC}$, pGB/II-III$^{HC}$, and pGB/III$^{HC}$ plasmids (FIG. 2) were confirmed.

2. In Vitro and Ex Vivo Analysis of Translation Efficiency of Chimeric IRES Elements.

To assess the translational efficiencies of RNAs transcribed from the plasmids shown in FIG. 2, some of which contain chimeric IRES viral sequences, translation initiation activities were determined in vitro in rabbit reticulocyte lysates and ex vivo in primary tamarin hepatocytes. To facilitate quantitation ex vivo, the MluI-XhoI fragment (nts 491–9398), spanning almost the entire GBV-B coding sequence and the 3' NTR of the cDNA in pGBV-B/Mlu, was replaced by a fragment encoding Renilla luciferase (RLuc) followed by the GBV-B 3' NTR. This substitution was carried out downstream of the chimeric sequences, generating plasmids pI-II-III$^{HC}$-Luc, pΔIb/II-III$^{HC}$-Luc, pII-III$^{HC}$-Luc, and pIII$^{HC}$-Luc that were used in translation studies.

Figure 3:
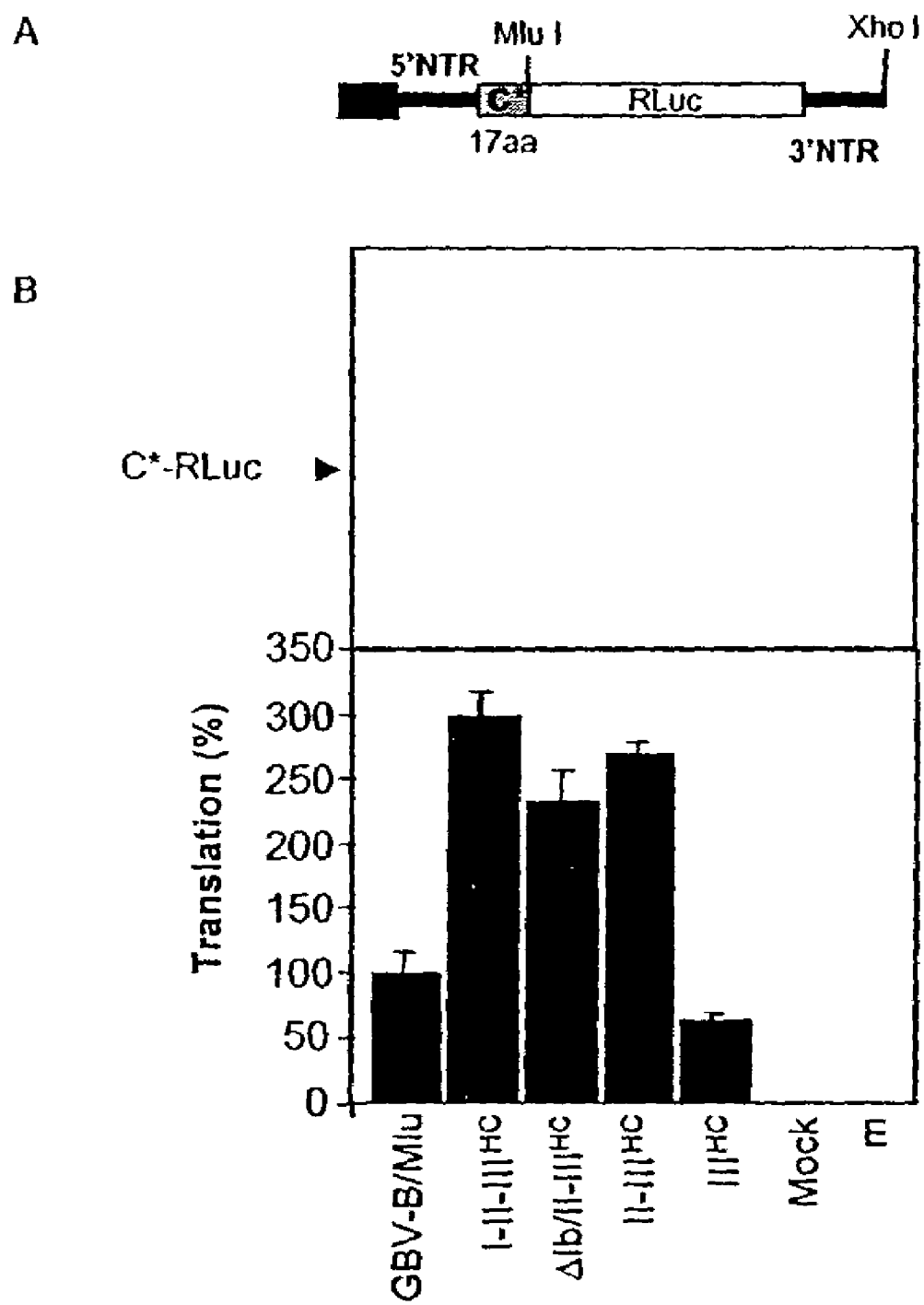
FIGS. 3A and 3B. In vitro translation of RLuc reporter transcripts (shown schematically in FIG. 3A) in which the initiation of translation of RLuc is dependent upon the upstream viral or chimeric IRES.

These plasmids were linearized at the Xho I restriction site and used as templates for in vitro transcription using T7 RNA polymerase (Megascript kit, Ambion). In vitro translations were performed in Flexi Rabbit Reticulocyte lysates as described by the supplier (Promega) with 125 mM KCl in the presence of $^{35}$S-Methionine. The RNA transcript concentration was 12.5 ng/μl, well below the saturation point. Translation products were analyzed by 8% SDS-PAGE and quantitated by PhosphorImager analysis (Molecular Dynamics). Exemplary results are shown in FIG. 3.

Reporter RNAs representing I-II-III$^{HC}$, ΔIb/II-III$^{HC}$, and II-III$^{HC}$, all of which contain the complete HCV IRES element, translated with about 2.5-fold higher efficiency as compared to GBV-B/Mlu RNA which contains the intact GBV-B IRES (FIG. 2). The translational activity observed for III$^{HC}$ was similar to that observed for the GBV-B/Mlu RNA. This is remarkable as this RNA contains a chimeric IRES in which upstream and downstream sequences flanking domain III of the HCV IRES are derived from the GBV-B IRES. These data suggest that the fusion of HCV and GBV-B 5'NTR sequences did not adversely affect translational activity of the internal ribosome entry site (IRES) when assayed in the cell-free translation system.

To assess the translational activity of these chimeric reporter RNA transcripts in living tamarin cells, in vitro transcribed RNA was mixed with the lipid-based compound DMRIE (Life Technologies) and transfected into primary tamarin hepatocytes (*S. oedipus*) that were prepared as described previously (Beames et al., 2000, incorporated herein by reference). As an internal control, an RNA transcript encoding firefly luciferase (FLuc) under translational control of the EMCV IRES was cotransfected at 1:19th the abundance of the RLuc reporter constructs.

Figure 4:
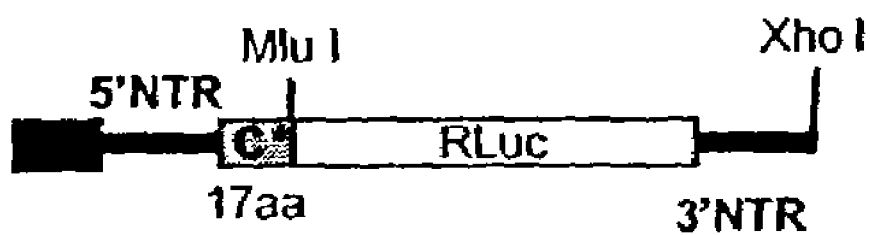
FIG. 4. Shows the translational activity of RLuc reporter transcripts (normalized to FLuc control transcript) in examples of transfected primary tamarin hepatocytes.
Figure 4:
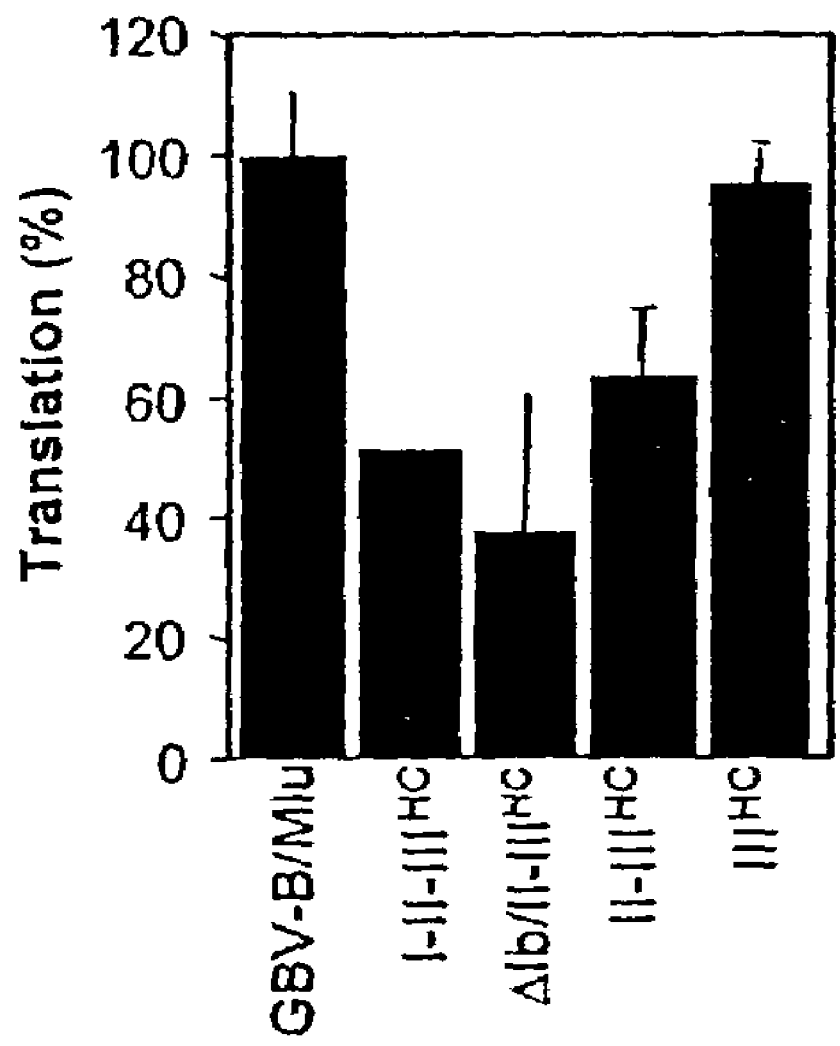

Translational activity was quantitated by determining the levels of luciferase activity 24 hours following transfection (FIG. 4). In this system, which may represent more closely the conditions present during GBV-B infection of the tamarin, the translational activity of each of the RNA transcripts containing the complete HCV IRES was lower than that observed with the GBV-B/MluI control. Thus, the GBV-B IRES may be more active in tamarin cells (the normal host species for GBV-B) than the HCV IRES. However, the chimeric transcript $III^{HC}$ which contains domain III of the HCV IRES in lieu of its GBV-B counterpart had translational activity comparable to that of GBV-B/MluI.

Although the data shown in FIG. 3 and FIG. 4 indicate that there may be variation in the relative activities of these chimeric RNAs in different translation systems (in tamarin hepatocyte cultures and in a cell free translation system prepared from rabbit reticulocytes), these results may indicate that each of the chimeric IRES elements in these RNAs retains substantial translation-initiation activity.

Example 24

Infectivity of Chimeric Viral cDNAs Containing HCV 5'NTR Sequences within the Genetic Background of GBV-B.

1. Inoculation of Synthetic RNA into GBV-B Susceptible Tamarins.

After linearization of the plasmid DNAs shown in FIG. 2 by digestion with XhoI, genome-length RNA transcripts containing the chimeric 5' NTR sequences were transcribed from the plasmids using the T7 MegaScript kit (Ambion). An aliquot of the reaction products was tested by agarose gel electrophoresis to ensure RNA integrity and to approximate the quantity of RNA. The remaining RNA was frozen at −80° C. until inoculation, without further purification, into the liver of susceptible tamarins. Individual animals (*S. mystax*) received a dose of approximately 100–200 μg of RNA transcribed from only one of the plasmids shown in FIG. 2. The RNAs were inoculated into the liver under direct visualization following exposure by laparotomy. Inoculated animals were followed as described in the preceding sections of this document, with periodic testing of serum ALT, antibody to the NS3 protein of GBV-B, GBV-B genome, and with liver biopsy to assess pathologic changes in the liver. All tamarins were housed at the Southwest Regional Primate Research Center at the Southwest Foundation for Biomedical Research. Animals were cared for by members of the Department of Laboratory Animal Medicine at the Southwest Foundation for Biomedical Research in accordance with the Guide for the Care and Use of laboratory Animals. All protocols were approved by the Institutional Animal Care and Use Committee.

The primary indicator of successful infection was detection of sustained viremia in samples of serum collected over a period of weeks. Viremia was monitored by detection of GBV-B RNA using a sensitive and specific real-time RT-PCR assay. RNA was isolated from virus present in tamarin serum using the QiaAmp viral RNA extraction kit (Qiagen) and amplified in a one-step RT-PCR reaction utilizing TaqMan EZ core reagents (Perkin Elmer). First-strand cDNA synthesis was carried out using the primer NS5ARPp (5'-GAAGGAGGGAGGTTTGAAGGA-3', position 6949–6969)(SEQ ID NO:14). The cDNA product was quantified in a 5' exonuclease PCR (TaqMan) assay using a primer-probe combination that recognized sequences in the GBV-B NS5A gene. The primers NS5ARPp and NS5AFPp (5'-CCAGTTCCGGGCAAGAACT-3', position 6844–6862)(SEQ ID NO:15) and probe (nts 6913–6938) were obtained from Fisher and Perkin Elmer, respectively. A synthetic RNA derived from the infectious clone was used as the standard for quantitation of the RNA.

There was no evidence for replication of the I-II-$III^{HC}$, II-$III^{HC}$, and ΔIb/II-$III^{HC}$ chimeras following their inoculation into the liver of individual GBV-B naïve tamarins during the 22-week follow up period, leading us to conclude that these chimeric RNAs are replication-incompetent. In contrast, RT-PCR suggested the possible presence of a low level of viral RNA in the serum of the animal injected with $III^{HC}$ chimera 1–2 weeks postinoculation, followed by disappearance of any sign of viremia. However, 12 weeks after inoculation with the $III^{HC}$ RNA, viremia reappeared in tamarin T16444, rapidly reaching a titer in excess of $10^7$ genome copies per ml, and subsequently persisting for 20 weeks (terminating 32 weeks following inoculation of the RNA) (FIG. 5). The course of the infection in this animal from week 12 on was similar to what is seen in infection of naïve animals with the wild-type infectious clone, with the exception that there was no detectable evidence of antibodies to the NS3 protein. The long delay to the appearance of the secondary viremia in this animal suggests a requirement for the accumulation of adaptive mutations that are compensatory to changes in the replication capacity of the RNA related to the presence of the chimeric 5'NTR sequence.

The results shown in FIG. 5 indicate the replication competence of the $III^{HC}$ chimeric RNA (see FIG. 2) following intrahepatic inoculation of synthetic RNA in a GBV-B naïve tamarin (*S. mystax*). The presence of the chimeric 5'NTR sequence was confirmed in the RNA replicating in this animal by RT-PCR amplification of RNA extracted from the serum, followed by direct DNA sequencing of the amplified cDNA.

To prove that inoculation of T16444 with synthetic $III^{HC}$ chimeric RNA had led to the rescue and replication of virus containing the chimeric 5'NTR sequence, serum collected 14 weeks after the inoculation of this animal with RNA was used to inoculate a second GBV-B naive animal (T16451) by intravenous injection. This is a stringent test for the presence of virus, since nonpackaged viral RNA that might be released from the liver into the serum would be expected to be highly degraded and no longer infectious. Only viral RNA packaged into viral particles would be expected to transmit the infection. This second animal rapidly developed evidence of GBV-B infection, with viremia detected as early as 1 week after infection, and with a peak viremia of greater than $10^8$ genome copies/ml by 4 weeks postinfection. The rapid appearance of the viremia and early robust replication of the virus in this second animal suggested that the chimeric virus had indeed undergone adaptation and that it no longer required a lengthy incubation period to induce viremia.

These results confirm that the synthetic chimeric III$^{HC}$ RNA replicated and produced infectious virus particles, capable of transmitting the infection to a second animal. Liver biopsy in this animal confirmed the presence of hepatic inflammation, while serial determinations of serum ALT activities demonstrated the typical profile of acute liver injury that normally accompanies wild-type GBV-B or HCV infections. The demonstration of hepatitis in association with infection with the chimeric III$^{HC}$ virus enhances its potential utility as a surrogate virus for evaluation of antiviral agents directed against the IRES or RNA replication signals residing within domain III of the HCV 5'NTR.

Example 25

Sequence Analysis of Recovered Chimeric IIIHC Virus

The lengthy delay prior to the appearance of high level viremia in T16444 coupled with the early robust replication of virus collected late in the course of infection in T16444 in a second animal suggests that the chimeric III$^{HC}$ virus had undergone adaptation to the presence of the chimeric 5'NTR. To determine the nature of the mutations contributing to this adaptation, viral RNA from both animals was amplified by RT-PCR and subjected to sequencing and comparison with the parent synthetic III$^{HC}$ RNA.

Viral RNA was isolated from serum obtained at week 14 from tamarin T16444, and week 4 or 8 from T16451 using Qiamp Viral RNA extraction kit (Qiagen). Random or GBV-B specific primers were used to prepare cDNA using MMLV reverse transcriptase from the Advantage RT-for-PCR kit (Clontech). PCR amplification of 1–2 kb fragments was carried out using the Advantage 2 PCR enzyme system (Clontech) utilizing GBV-B specific primers. Amplimers were purified through a silica gel membrane (QiaQuick PCR purification kit, Qiagen) and subjected to direct sequencing on an ABI 373XL instrument. The 3' terminus of the viral genome was ligated to a 27-mer oligonucleotide as described in the previous section for parent GBV-B. This RNA was then subjected to reverse transcription using a primer complementary to the ligated primer, and the cDNA was subsequently amplified using the same 3' primer and a 5' primer specific for a sequence in the 3'NTR (nts 9092–9111). A semi-nested PCR was performed with an internal 5' primer (nts 9097–9114). The 5' terminus of the viral genome was subjected to reverse transcription using a 3' primer complementary to the domain III of the HCV 5'NTR sequence (nts 209–229 of the HCV cDNA). The resulting cDNA was ligated to the 27-mer oligonucleotide and amplified using a primer complementary to the ligated primer and the same 3' primer used for RT. A semi-nested PCR was then performed using an internal 3' primer (nts 137–156 of the HCV cDNA). Results are shown in FIG. 7.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,800,159
U.S. Pat. No. 4,883,750
U.S. Pat. No. 5,279,721
U.S. Pat. No. 5,807,670
EPA No. 320,308
EPA No. 329,822
GB Application No. 2,202,328
PCT/US87/00880
PCT/US89/01025
WO 88/10315
WO 89/06700
WO 90/07641
Al et al., *Virus Res.*, 53:141–149, 1998.
Alter et al., *Hepatology*, 26:625–655, 1997.
Beames et al., *J. Virol.*, 74:11764–11772, 2000.
Beard et al., *Hepatology*, 1999.
Behrens et al., *EMBO. J.*, 15:12–22, 1996.
Chambers et al., *J. Virol.*, 73:3095–3101, 1999.
Choo et al., *Proc. Natl. Acad. Sci. USA*, 91:1294–1298, 1994.
Consensus Development Panel. National Institutes of Health Consensus Development Conference Panel statement: Management of hepatitis C. *Hepatology*, 26:Supplement 1[3], 2S–10S, 1997.
Farci et al., *Science*, 258:135–140. 1992.
Farci et al., *J. Infectious Diseases*, 165:1006–1011, 1992.
Filocamo et al., *J. Virol*, 71 1417–27, 1997.
Frohman, *PCR Protocols: A Guide To Methods And Applications*, Academic Press, New York, 1990.
Frolov et al., *RNA*, 4:1418–1435, 1998.
Grakoui et al., *J. Virol.*, 67(5):2832–2843, 1993.
Grakoui et al., *J. Virol.*, 67(3):1385–95. 1993.
Hijikata et al., *J. Virol.*, 67:4665–4675, 1993.
Honda et al., *RNA*, 2:955–956, 1996.
Inchauspe et al., *Proc. Natl. Acad. Sci. USA*, 88:10292–10296, 1991.
Karayiannis et al., *Hepatology*, 9:186–192, 1989.
Kim et al., *Cell*, 87:343–355, 1996.
Kolykhalov et al., *Science*, 277:570–574, 1997.
Kolykhalov et al., *J. Virol.*, 70:3363–3371, 1996.
Landt et al., *Gene*, 96:125–128, 1990.
Lemon and Honda, *Seminars in Virology*, 8:274–288, 1997.
Lindenbach and Rice, *J. Virol.*, 73:4611–4621, 1999.
Lu and Wimmer, *Proc., Natl., Acad., Sci., USA*, 93:1412–1417, 1996.
Muerhoff et al., *J. Virol.*, 69:5621–5630, 1995.
Neumann et al., *Science*, 282:103–107, 1998.
Pletnev et al., *Proc. Natl. Acad. Sci. USA*, 89:10532–10536, 1992.

Remington's Pharmaceutical Sciences, 15th Edition, pages 1035–1038 and 1570–1580.
Reynolds et al., *EMBO. J*, 14:6010–6020, 1995.
Rijnbrand et al., Mutational analysis of the GB virus B internal ribosome entry site. Submitted for publication, 1999.
Sambrook, et al., *Molecular Cloning, A Laboratory Manual*, 2nd ed., Cold Spring Harbor Laboratory, Cold Spring, Harbor, N.Y., 1989.
Scarselli et al., *J. Virol.*, 71 4985–4989, 1997.
Schlauder et al., *J. Med. Virol.*, 46:81–90, 1995.
Shaffer et al., *J. Virol.*, 69:600–6604, 1995.
Simons, et al., *Proc. Natl. Acad. Sci.*, 92:3401–3405, 1995.
Tanaka et al., *Biochem. Biophys. Res. Comm.*, 215:744–749, 1995.
Teller et al., *J. Clin. Micro.*, 34:3085–3091, 1996.
Todd et al., *J. Virol.*, 71:8868–74, 1997.
Yanagi et al., *Proc. Natl. Acad. Sci. USA*, 16:8738–8743, 1998.
Yao et al., *Nature Structural Biology*, 4: 463–467, 1997.
Zhao et al., *J. Virol.*, 73:1546–1554, 1999.

What is claimed is:

1. An isolated polynucleotide sequence of a chimeric GBV-B viral genome comprising a GBV-B/HCV chimera, wherein the GBV-B/HCV chimera comprises at least part a 5' NTR sequence derived from a HCV 5' NTR.

2. The isolated polynucleotide of claim 1, wherein domain III of the 5' NTR is derived from a HCV 5'NTR.

3. The isolated polynucleotide of claim 1, wherein domain Ib of GBV-B is deleted.

4. An isolated polynucleotide comprising a chimeric GBV-B genome, wherein at least part, but not all of a 5' NTR sequence is derived from a HCV 5' NTR.

5. The polynucleotide of claim 4, wherein at least domain I, II, III, or IV of the 5' NTR is derived from a HCV 5' NTR, but not all.

6. The polynucleotide of claim 4, wherein domain I of the 5' NTR is derived from a HCV 5'NTR.

7. The polynucleotide of claim 4, wherein domain II of the 5' NTR is derived from a HCV 5'NTR.

8. The polynucleotide of claim 4, wherein domain III of the 5' NTR is derived from a HCV5'NTR.

9. The polynucleotide of claim 8, wherein 5' NTR domain Ib of GBV-B is deleted.

10. The polynucleotide of claim 4, wherein domain IV of the 5' NTR is derived from a HCV 5'NTR.

11. The polynucleotide of claim 4, wherein domain I and domain II of the 5' NTR is derived from a HCV 5'NTR.

12. The polynucleotide of claim 4, wherein domain I and domain III of the 5' NTR is derived from a HCV 5'NTR.

13. The polynucleotide of claim 4, wherein domain I and domain IV of the 5' NTR is derived from a HCV 5'NTR.

14. The polynucleotide of claim 4, wherein domain II and domain III of the 5' NTR is derived from a HCV 5'NTR.

15. The polynucleotide of claim 4, wherein domain II and domain IV of the 5' NTR is derived from a HCV 5'NTR.

16. The polynucleotide of claim 4, wherein domain III and domain IV of the 5' NTR is derived from a HCV 5'NTR.

17. The polynucleotide of claim 4, wherein domain II, domain III and domain IV of the 5' NTR is derived from a HCV 5'NTR.

18. The polynucleotide of claim 17, wherein 5' NTR domain Ib of GBV-B is deleted.

19. A viral expression construct comprising a chimeric GBV-B polynucleotide, wherein at least a part of the 5' NTR sequence is derived from a HCV 5' NTR.

20. The viral expression construct of claim 19, wherein domain III of the 5' NTR is derived from a HCV 5' NTR.

21. The viral expression construct of claim 19, further comprising a deletion of the GBV-B 5' NTR domain Ib region.

22. The viral expression construct of claim 19, wherein said construct is a plasmid.

23. The viral expression construct of claim 19, wherein said construct is a virus.

24. A hepatotropic virus comprising a chimeric GBV-B polynucleotide, wherein at least a part of the 5' NTR sequence is derived from a HCV 5' NTR.

25. The hepatotropic virus of claim 24, wherein domain III of the 5' NTR is derived from a HCV 5' NTR.

26. The hepatotropic virus of claim 24, further comprising a deletion of the GBV-B 5' NTR domain Ib region.

27. The hepatotropic virus of claim 25, wherein the virus propagates in vivo.

* * * * *

UNITED STATES PATENT AND TRADEMARK OFFICE
CERTIFICATE OF CORRECTION

PATENT NO. : 7,141,405 B2
APPLICATION NO. : 10/189359
DATED : November 28, 2006
INVENTOR(S) : Martin et al.

It is certified that error appears in the above-identified patent and that said Letters Patent is hereby corrected as shown below:

In claim 1, column 89, line 50, after "least part", insert --of--therefor.

Signed and Sealed this

Twentieth Day of March, 2007

JON W. DUDAS
*Director of the United States Patent and Trademark Office*